(12) United States Patent
Parham et al.

(10) Patent No.: US 9,422,287 B2
(45) Date of Patent: Aug. 23, 2016

(54) BRIDGED TRIARYLAMINES AND -PHOSPHINES AS MATERIALS FOR ELECTRONIC DEVICES

(75) Inventors: Amir Hossain Parham, Frankfurt am Main (DE); Christof Pflumm, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 527 days.

(21) Appl. No.: 13/640,860

(22) PCT Filed: Mar. 16, 2011

(86) PCT No.: PCT/EP2011/001295
§ 371 (c)(1),
(2), (4) Date: Oct. 12, 2012

(87) PCT Pub. No.: WO2011/128017
PCT Pub. Date: Oct. 20, 2011

(65) Prior Publication Data
US 2013/0026422 A1    Jan. 31, 2013

(30) Foreign Application Priority Data
Apr. 14, 2010   (DE) .......................... 10 2010 014 933

(51) Int. Cl.
| | | |
|---|---|---|
| H01L 51/50 | (2006.01) | |
| C07D 471/22 | (2006.01) | |
| C07D 471/06 | (2006.01) | |
| C07D 471/10 | (2006.01) | |
| C07D 471/16 | (2006.01) | |
| C07D 471/20 | (2006.01) | |
| C07D 498/06 | (2006.01) | |
| C07D 498/16 | (2006.01) | |
| C07D 498/22 | (2006.01) | |
| C07D 513/06 | (2006.01) | |
| C07D 513/16 | (2006.01) | |
| C07D 513/22 | (2006.01) | |
| H05B 33/20 | (2006.01) | |
| H01L 51/00 | (2006.01) | |

(52) U.S. Cl.
CPC ............ *C07D 471/22* (2013.01); *C07D 471/06* (2013.01); *C07D 471/10* (2013.01); *C07D 471/16* (2013.01); *C07D 471/20* (2013.01); *C07D 498/06* (2013.01); *C07D 498/16* (2013.01); *C07D 498/22* (2013.01); *C07D 513/06* (2013.01); *C07D 513/16* (2013.01); *C07D 513/22* (2013.01); *H01L 51/0072* (2013.01); *H01L 51/5048* (2013.01); *H05B 33/20* (2013.01); *H01L 51/004* (2013.01); *H01L 51/0008* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | |
|---|---|---|
| 2006/0063027 A1 | 3/2006 | Vestweber et al. |
| 2008/0220285 A1 | 9/2008 | Vestweber et al. |
| 2009/0165848 A1* | 7/2009 | Yoon et al. .................... 136/256 |
| 2010/0051928 A1 | 3/2010 | Fukuzaki |
| 2011/0266533 A1 | 11/2011 | Buesing et al. |

FOREIGN PATENT DOCUMENTS

| | | | |
|---|---|---|---|
| CN | 1756824 A | 4/2006 | |
| CN | 102272966 A | 12/2011 | |
| JP | 2008-227088 | * 9/2008 | ............. H01L 51/05 |
| WO | WO-2006/033563 A1 | 3/2006 | |
| WO | WO-2006/122630 A1 | 11/2006 | |
| WO | WO-2007/064104 A1 | 6/2007 | |
| WO | WO-2010/083871 A1 | 7/2010 | |

OTHER PUBLICATIONS

STN Columbus on the Web Session, pp. 3-5.(results 1-4) 1989.
Caplus Database, Accession No. XP002637992, 4 pages, 2011.
International Search Report for PCT/EP2011/001295 mailed Jun. 1, 2011.

* cited by examiner

*Primary Examiner* — Gregory Clark
(74) *Attorney, Agent, or Firm* — Drinker Biddle & Reath LLP

(57) ABSTRACT

The present invention relates to a compound according to formula (I), to the use thereof in an electronic device and to an electronic device which comprises one or more compounds according to formula (I).

26 Claims, No Drawings

BRIDGED TRIARYLAMINES AND -PHOSPHINES AS MATERIALS FOR ELECTRONIC DEVICES

RELATED APPLICATIONS

This application is a national stage application (under 35 U.S,C. §371) of PCT/EP2011/001295, filed Mar. 16, 2011, which claims benefit of German Patent Application No. 10 2010 014 933.0, filed Apr. 14, 2010.

The present invention relates to a compound of the formula (I) and to the use thereof in an electronic device, and to an electronic device which comprises one or more compounds of the formula (I).

The general structure of organic electroluminescent devices is described, for example, in U.S. Pat. Nos. 4,539,507, 5,151,629, EP 0676461 and WO 1998/27136.

Hole-transport and -injection materials which are known from the prior art are, inter alia, arylamine compounds. Materials of this type based on indenofluorenes are disclosed, for example, in WO 2006/100896 and WO 2006/122630.

However, the known hole-transporting materials frequently have low electron stability, which reduces the lifetime of electronic devices comprising these compounds.

Furthermore, improvements are desirable with respect to the efficiency of fluorescent organic electroluminescent devices and the lifetime, especially in the case of blue-fluorescent devices.

Carbazole derivatives, for example bis(carbazolyl)biphenyl, are frequently used as matrix materials in accordance with the prior art. There is still a demand here for alternative materials which preferably have a high glass-transition temperature and cause an extended lifetime of the electronic devices.

Furthermore, ketones (WO 2004/093207), phosphine oxides and sulfones (WO 2005/003253) are used as matrix materials for phosphorescent emitters. Low operating voltages and long lifetimes are achieved, in particular, with ketones. There is still a need for improvement here, in particular with respect to the efficiency and compatibility with metal complexes which contain ketoketonate ligands, for example acetylacetonate.

Furthermore, metal complexes, for example BAlq or bis[2-(2-benzothiazolyl)phenolate]zinc(II), are used as matrix materials for phosphorescent emitters. There is a need for improvement here, in particular with respect to the operating voltage and chemical stability. Purely organic compounds are frequently more stable than the metal complexes. Thus, some of the metal complexes are sensitive to hydrolysis, which makes handling thereof more difficult.

Also of interest is the provision of alternative materials as matrix components of mixed-matrix systems. A mixed-matrix system in the sense of this application is taken to mean a system in which two or more different matrix compounds are used as emitting layer mixed together with one (or more) dopant compounds. These systems are of particular interest as constituents of phosphorescent organic electroluminescent devices. For more detailed information, reference is made to the application WO 2010/108579. Compounds known from the prior art which may be mentioned as matrix components in mixed-matrix systems are, inter alia, CBP (biscarbazolylbiphenyl) and TCTA (triscarbazolyltriphenylamine). However, there continues to be a demand for alternative compounds for use as matrix components in mixed-matrix systems. In particular, there is a demand for compounds which cause an improvement in the operating voltage and lifetime of the electronic devices.

Overall, there is a demand in the area of functional materials for electronic devices for alternative materials which have novel, more preferably improved properties.

The applications WO 2006/033563 and WO 2007/031165 disclose, inter alia, triarylamine derivatives in which the individual aryl groups are bridged to one another. The compounds are employed as hole-transport materials and/or as emitting materials in electronic devices. The application WO 2010/083871 discloses compounds in which aryl groups are condensed onto a piperidine ring. The compounds are employed as hole-transport materials and/or as emitting materials in electronic devices.

However, there continues to be a need for improvement with respect to the lifetime, efficiency and operating voltage of the devices. In addition, it is advantageous for the compounds to have high thermal stability and a high glass-transition temperature and to be sublimable without decomposition.

The present invention relates to compounds of the formula (I), which exhibit advantageous properties on use in electronic devices, preferably organic electroluminescent devices. The compounds are preferably used as hole-transport or hole-injection materials, as matrix materials for phosphorescent emitters or as emitter materials.

The invention thus relates to a compound of the formula (I)

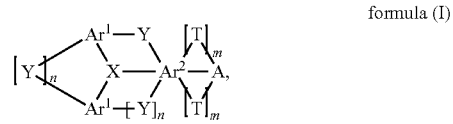

formula (I)

where the following applies to the symbols and indices occurring:

X is N, P or P=O;

Y is on each occurrence, identically or differently, $C(R^1)_2$, C=O, C=$NR^1$, O, S, SO, $SO_2$, $PR^1$, $POR^1$, NAr, $NR^1$ or a single bond;

T is on each occurrence, identically or differently, $C(R^1)_2$, C=O, C=$NR^1$, O, S, SO, $SO_2$, $PR^1$, $POR^1$, NAr, $NR^1$ or a single bond;

A is equal to $Ar^3$ or equal to $X(Ar^4)_2$, where the bond to a group T starts from the aromatic or heteroaromatic ring of the group $Ar^3$ or $Ar^4$, and the two groups $Ar^4$ of a group $X(Ar^4)_2$ may be connected to one another via a group T;

Ar, $Ar^1$, $Ar^2$, $Ar^3$, $Ar^4$ are selected on each occurrence, identically or differently, from an aryl or heteroaryl group having 5 to 30 aromatic ring atoms, which may be substituted by one or more radicals $R^2$;

$R^1$, $R^2$ is on each occurrence, identically or differently, H, D, F, Cl, Br, I, CHO, $NAr_2$, $N(R^3)_2$, C(=O)$R^3$, P(=O)$(R^3)_2$, S(=O)$R^3$, S(=O)$_2R^3$, $CR^3$=$C(R^3)_2$, CN, $NO_2$, $Si(R^3)_3$, $B(OR^3)_2$, $OSO_2R^3$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by —$R^3$C=$CR^3$—, —C≡C—, $Si(R^3)_2$, $Ge(R^3)_2$, $Sn(R^3)_2$, C=O, C=S, C=Se, C=$NR^3$, P(=O)($R^3$), SO, $SO_2$, $NR^3$, —O—, —S—, —COO— or —$CONR^3$— and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 60 aromatic ring atoms, which may in each case be substituted by one or more radicals $R^3$, or a combination of these systems, where two or more radicals $R^1$ and $R^2$ may be linked to one another and may form a ring or ring system;

$R^3$ is on each occurrence, identically or differently, H, D, F, Cl, Br, I, CHO, $NAr_2$, $N(R^4)_2$, $C(=O)R^4$, $P(=O)(R^4)_2$, $S(=O)R^4$, $S(=O)_2R^4$, $CR^4=C(R^4)_2$, CN, $NO_2$, $Si(R^4)_3$, $B(OR^4)_2$, $OSO_2R^4$, OH, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^4$, where one or more non-adjacent $CH_2$ groups may be replaced by —$R^4C=CR^4$—, —C≡C—, $Si(R^4)_2$, $Ge(R^4)_2$, $Sn(R^4)_2$, C=O, C=S, C=Se, C=$NR^4$, $P(=O)$ $(R^4)$, SO, $SO_2$, $NR^4$, —O—, —S—, —COO— or —$CONR^4$— and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^4$, or an aryloxy or heteroaryloxy group having 5 to 60 aromatic ring atoms, which may in each case be substituted by one or more radicals $R^4$, or a combination of these systems, where two or more radicals $R^3$ may be linked to one another and may form a ring or ring system;

$R^4$ is on each occurrence, identically or differently, H, D, F or an aliphatic, aromatic and/or heteroaromatic organic radical having 1 to 20 C atoms, in which, in addition, one or more H atoms may be replaced by F; two or more identical or different substituents $R^4$ here may also be linked to one another and form a ring or ring system;

n is on each occurrence, independently of one another, 0 or 1, with the proviso that the sum of all values for n is greater than or equal to 1;

m is on each occurrence, independently of one another, 0 or 1, with the proviso that the sum of all values for m is greater than or equal to 1;

where furthermore the proviso applies that at least one group Y which represents a single bond must be present.

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aromatic ring system in the sense of this invention contains 6 to 60 C atoms in the ring system. A heteroaromatic ring system in the sense of this invention contains 5 to 60 aromatic ring atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl group or by a silyl group.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

An aromatic or heteroaromatic ring system having 5-60 aromatic ring atoms, which may also in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals $R^1$ and $R^2$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, 1-butoxy, s-butoxy, tbutoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

It is preferred in accordance with the invention for one or more groups selected from Ar, $Ar^1$, $Ar^2$, $Ar^3$ and $Ar^4$ to represent on each occurrence, identically or differently, an aryl group having 6 to 14 aromatic ring atoms or a heteroaryl group having 5 to 14 aromatic ring atoms, each of which may be substituted by one or more radicals $R^2$. It is particularly preferred for one or more groups selected from Ar, $Ar^1$, $Ar^2$, $Ar^3$ and $Ar^4$ to represent on each occurrence, identically or differently, an aryl group having 6 to 10 aromatic ring atoms or a heteroaryl group having 5 to 10 aromatic ring atoms, each of which may be substituted by one or more radicals $R^2$.

In a preferred embodiment of the invention, the group $Ar^2$ represents a group of the following formula (II), where the dashed lines symbolise the bond to the groups X and A, and Z is on each occurrence, identically or differently, $CR^2$ or N or is equal to C if the group X or A is bonded to this Z:

formula (II)

In a particularly preferred embodiment of the invention, the groups X and A are bonded in the 1,4- or 1,3-position, so that $Ar^2$ represents a group of the following formulae (III) or (IV), where Z is as defined above:

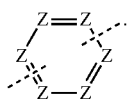

formula (III)

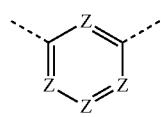

formula (IV)

It is very particularly preferred here for $Ar^2$ to represent a group of the formula (IV).

In a preferred embodiment of the invention, the groups Ar, $Ar^1$, $Ar^3$ and $Ar^4$ in compounds of the formula (I) are on each occurrence, identically or differently, phenyl, naphthyl, pyridyl, pyrimidyl, pyrazinyl, pyridazyl or triazinyl, particularly preferably phenyl, pyridyl, naphthyl or triazinyl.

It is furthermore preferred for X in the compounds according to the invention to be equal to N.

In a preferred embodiment of the compounds according to the invention, Y is on each occurrence, identically or differently, $C(R^1)_2$, S, O, C=O, $NR^1$ or a single bond, and particularly preferably $C(R^1)_2$ or a single bond, where, as stated above, at least one group Y which represents a single bond is present.

In a further preferred embodiment of the invention, T is selected on each occurrence, identically or differently, from $C(R^1)_2$, S, O, C=O and $NR^1$ if A represents a group $Ar^3$, and T is selected on each occurrence, identically or differently, from $C(R^1)_2$, S, O, C=O, $NR^1$ and a single bond if A represents a group $X(Ar^4)_2$.

T is particularly preferably equal to $C(R^1)_2$ if A represents a group $Ar^3$, and T is equal to $C(R^1)_2$ or a single bond if A represents a group $X(Ar^4)_2$.

It is preferred in accordance with the invention for the sum of the values of the indices n and m together to be equal to 2 or 3, i.e. for 2 or 3 groups Y and T to be present in the compounds according to the invention.

It is preferred in accordance with the invention for the sum of the values of n to be equal to one.

The formulae (I-1) to (I-4) represent preferred embodiments of the compounds according to the invention

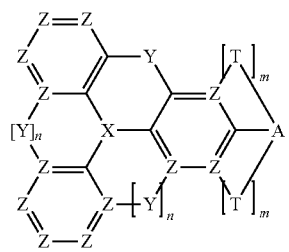

formula (I-1)

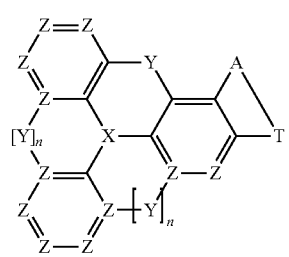

formula (I-2)

formula (I-3)

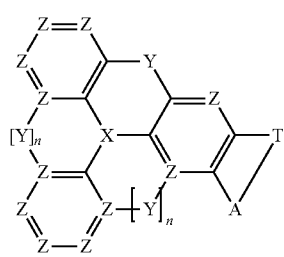

formula (I-4)

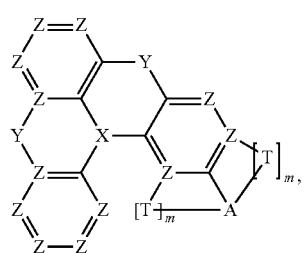

where the symbols and indices occurring are as defined above, and Z is on each occurrence, identically or differently, $CR^2$ or N or is equal to C if a group Y or T is bonded to this Z.

Formulae (I-5) to (I-14) represent further preferred embodiments of the compounds according to the invention formula (I-5)

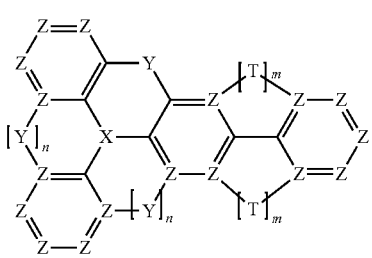

formula (I-6)

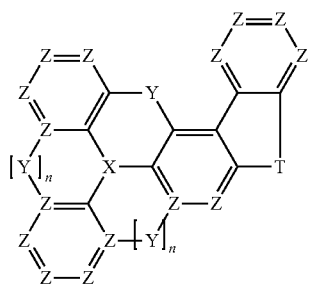

formula (I-7)

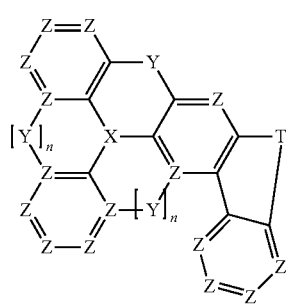

formula (I-8)

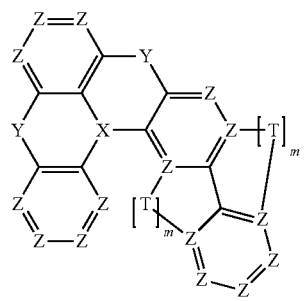

formula (I-9)

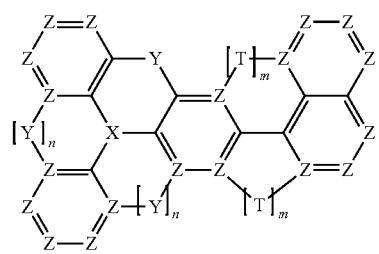

formula (I-10)

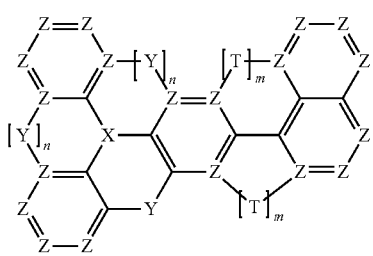

formula (I-11)

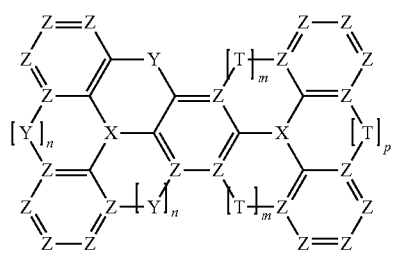

formula (I-12)

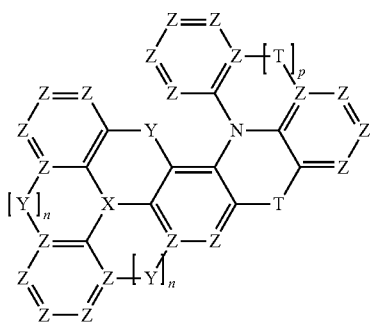

-continued

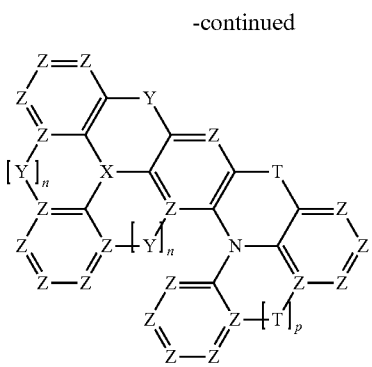

formula (I-13)

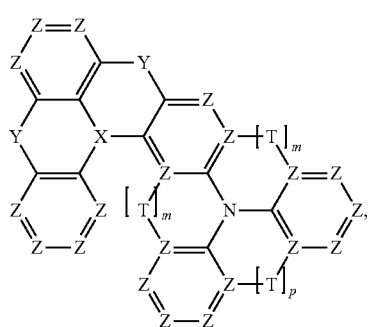

formula (I-14)

For compounds of one of the formulae (I-5) to (I-14), the symbols and indices occurring are defined as indicated above, and the following furthermore applies:

Z is on each occurrence, identically or differently, $CR^2$ or N if no group Y or T is bonded to the group Z and is on each occurrence C if a group Y or T is bonded to the group Z; and p is equal to 0 or 1.

In a preferred embodiment of the invention, 0, 1, 2 or 3 groups Z per formula (I-5) to (I-14) are equal to N and the remaining groups Z are equal to C or $CR^2$.

It is particularly preferred for no group Z to be equal to N, i.e. for Z to be on each occurrence $CR^2$ if no group Y or T is bonded to the group Z and to be on each occurrence C if a group Y or T is bonded to the group Z.

$R^1$ is furthermore preferably selected on each occurrence, identically or differently, from H, D, F, CN, $Si(R^3)_3$, NAr, $N(R^3)_2$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by —C≡C—, —$R^3$C=$CR^3$—, $Si(R^3)_2$, C=O, C=$NR^3$, $NR^3$, —O—, —S—, —COO— or —$CONR^3$—, or an aryl or heteroaryl group having 5 to 30 aromatic ring atoms, which may in each case be substituted by one or more radicals $R^3$.

$R^1$ is particularly preferably selected on each occurrence, identically or differently, from H, D, a straight-chain alkyl group having 1 to 8 carbon atoms, a branched alkyl group having 3 to 8 carbon atoms or an aryl group having 6 to 10 carbon atoms, where the said groups may each be substituted by one or more radicals $R^3$.

$R^1$ is very particularly preferably equal to H, D, methyl or phenyl.

The radical $R^2$ is preferably selected on each occurrence, identically or differently, from H, D, F, CN, $Si(R^3)_3$, NAr, $N(R^3)_2$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by —C≡C—, —$R^3$C=$CR^3$—, $Si(R^3)_2$, C=O, C=$NR^3$, $NR^3$, —O—, —S—, —COO— or —$CONR^3$—, or an aryl or heteroaryl group having 5 to 30 aromatic ring atoms, which may in each case be substituted by one or more radicals $R^3$.

The radical $R^3$ is preferably selected on each occurrence, identically or differently, from H, D, F, CN, $Si(R^4)_3$, NAr, $N(R^4)_2$ or a straight-chain alkyl or alkoxy group having 1 to 20 C atoms or a branched or cyclic alkyl or alkoxy group having 3 to 20 C atoms, each of which may be substituted by one or more radicals $R^4$, where one or more adjacent or non-adjacent $CH_2$ groups may be replaced by —C≡C—, —$R^4$C=$CR^4$—, $Si(R^4)_2$, C=O, C=$NR^4$, $NR^4$, —O—, —S—, COO— or —$CONR^4$—, or an aryl or heteroaryl group having 5 to 30 aromatic ring atoms, which may in each case be substituted by one or more radicals $R^4$.

The following formula (I-1a) represents a particularly preferred embodiment of the compounds according to the invention:

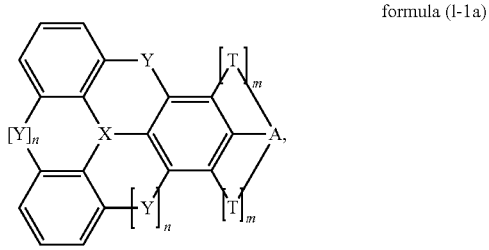

formula (I-1a)

where the symbols and indices occurring are as defined above, and the free positions on the aromatic rings are substituted by radicals $R^2$.

Very particularly preferred embodiments of the compounds according to the invention are the following formulae (I-1a-1) to (I-1a-55).

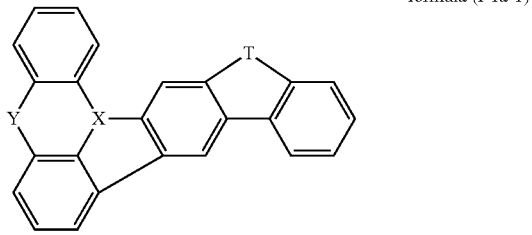

formula (I-1a-1)

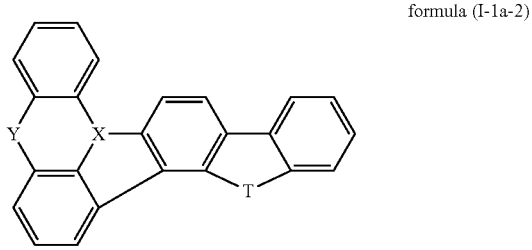

formula (I-1a-2)

formula (I-1a-3)
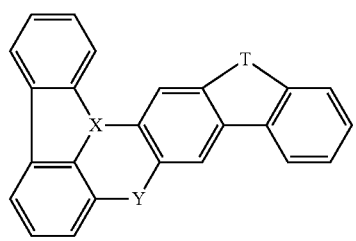
formula (I-1a-4)
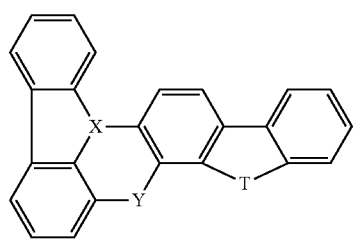
formula (I-1a-5)
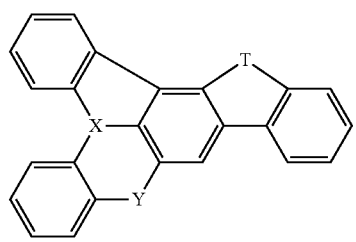
formula (I-1a-6)
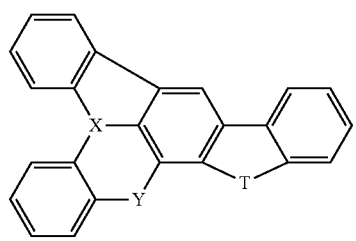
formula (I-1a-7)
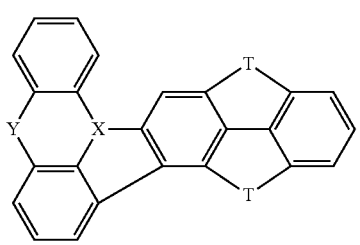
formula (I-1a-8)
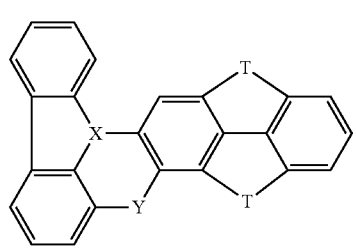
formula (I-1a-9)
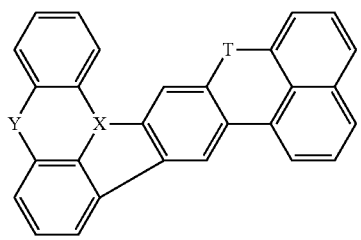
formula (I-1a-10)
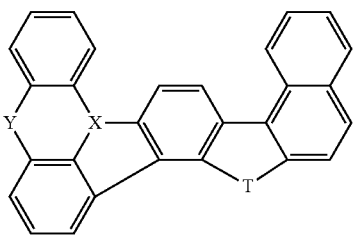
formula (I-1a-11)
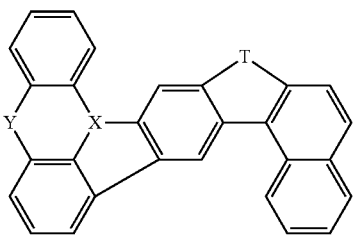
formula (I-1a-12)
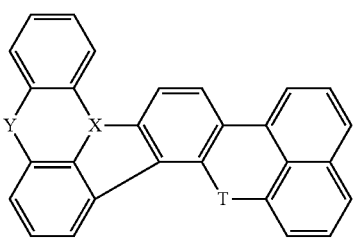
formula (I-1a-13)
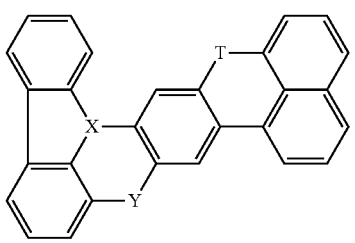
formula (I-1a-14)
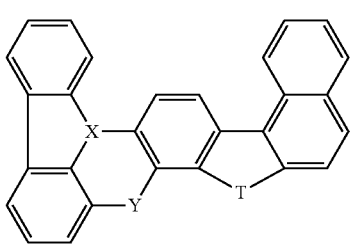

formula (I-1a-15)
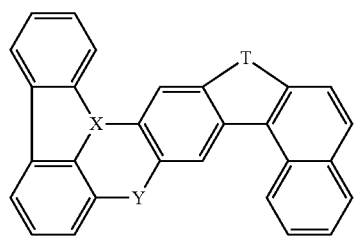
formula (I-1a-16)
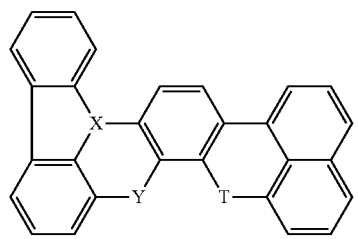
formula (I-1a-17)
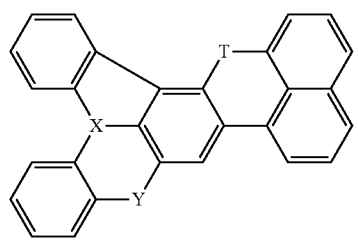
formula (I-1a-18)
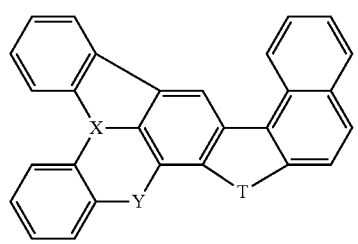
formula (I-1a-19)
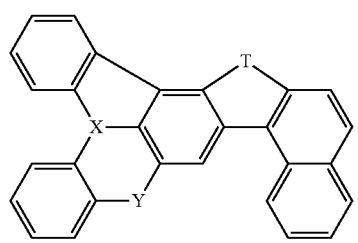
formula (I-1a-20)
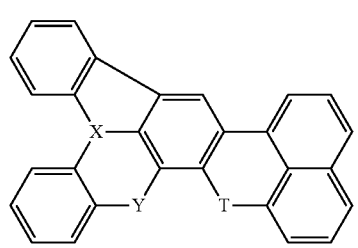
formula (I-1a-21)
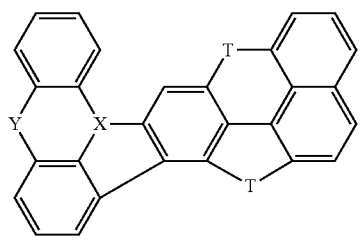
formula (I-1a-22)
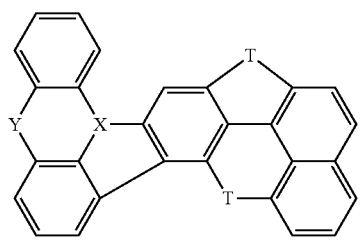
formula (I-1a-23)
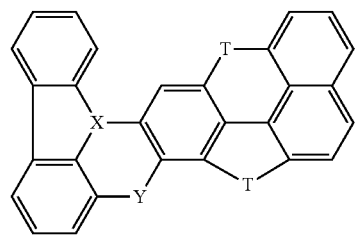
formula (I-1a-24)
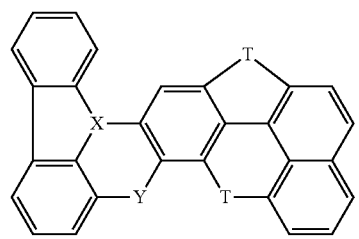
formula (I-1a-25)
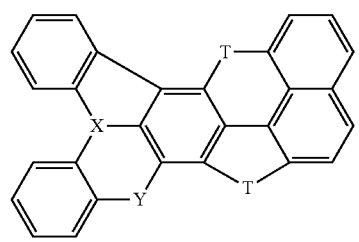
formula (I-1a-26)
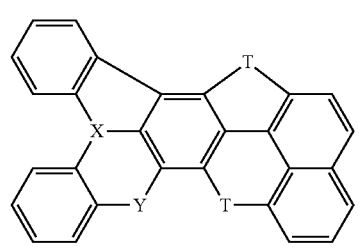

formula (I-1a-27)
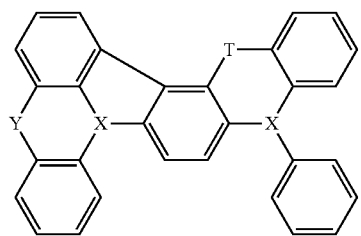
formula (I-1a-28)
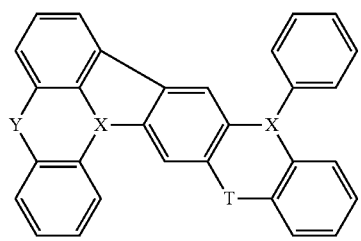
formula (I-1a-29)
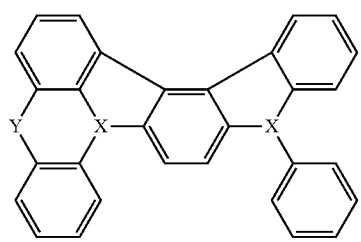
formula (I-1a-30)
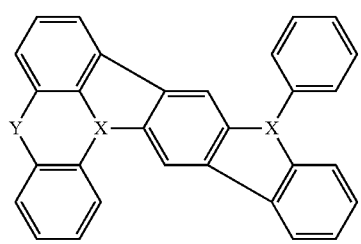
formula (I-1a-31)
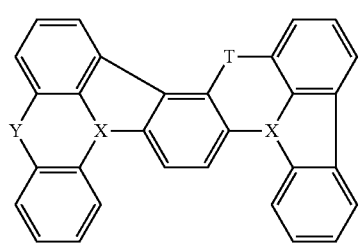
formula (I-1a-32)
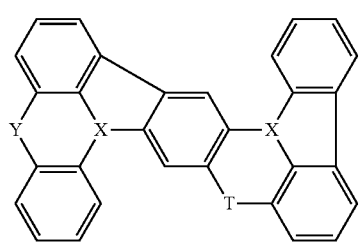
formula (I-1a-33)
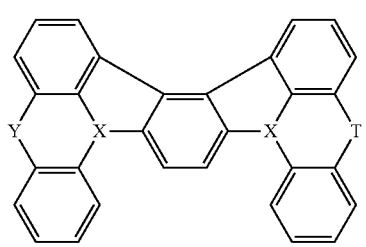
formula (I-1a-34)
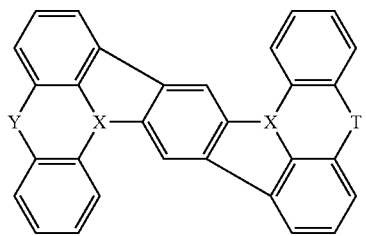
formula (I-1a-35)
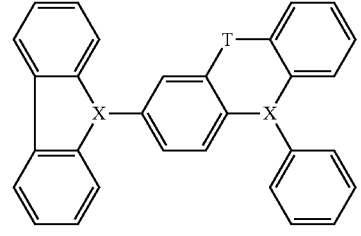
formula (I-1a-36)
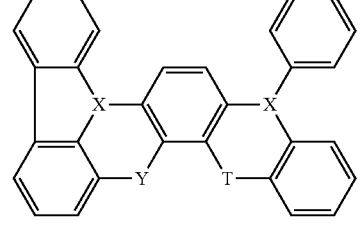
formula (I-1a-37)
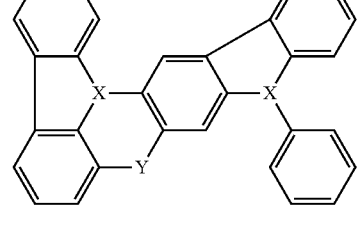
formula (I-1a-38)
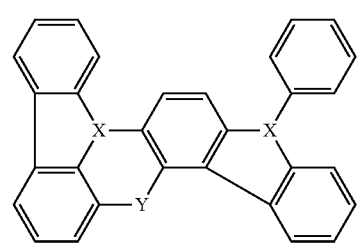

formula (I-1a-39)
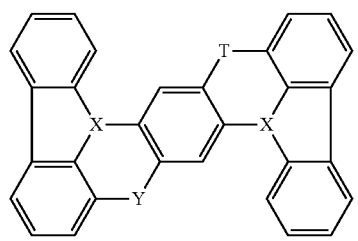
formula (I-1a-40)
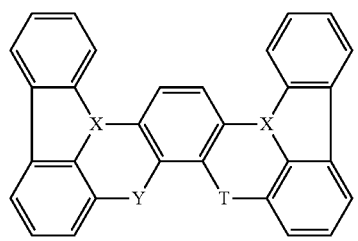
formula (I-1a-41)
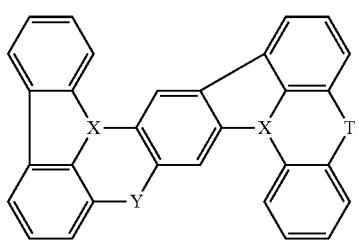
formula (I-1a-42)
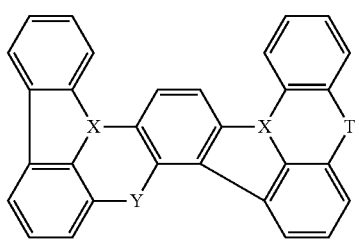
formula (I-1a-43)
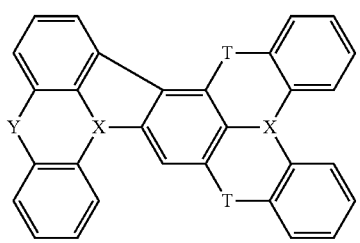
formula (I-1a-44)
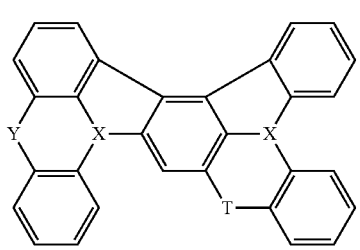
formula (I-1a-45)
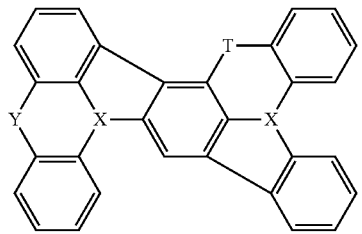
formula (I-1a-46)
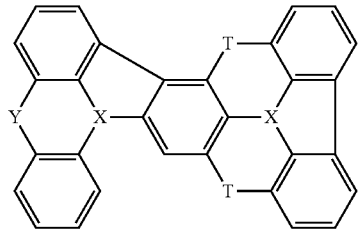
formula (I-1a-47)
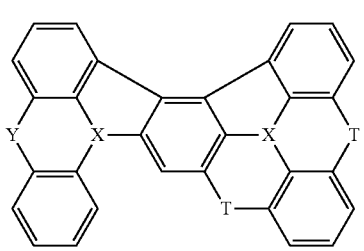
formula (I-1a-48)
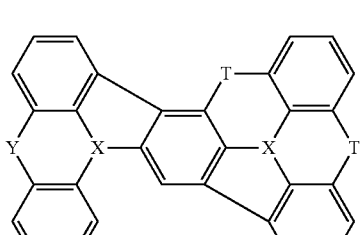
formula (I-1a-49)
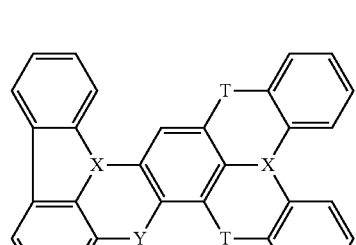
formula (I-1a-50)
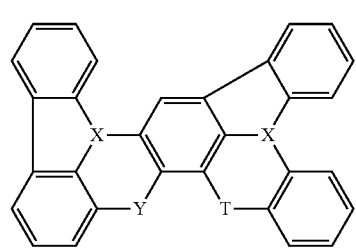

-continued

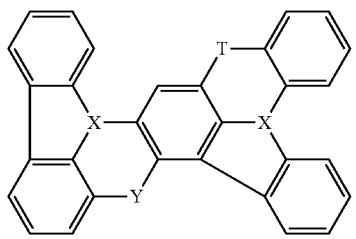

formula (I-1a-51)

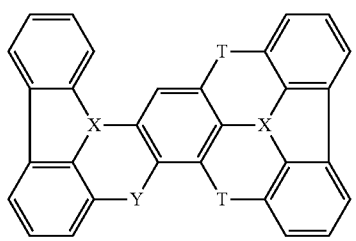

formula (I-1a-52)

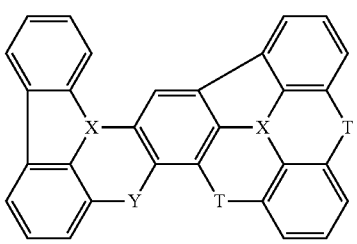

formula (I-1a-53)

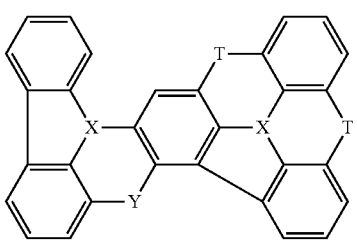

formula (I-1a-54)

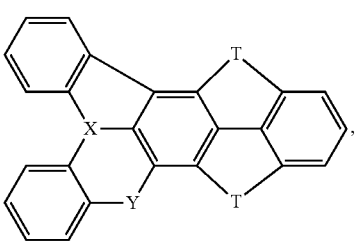

formula (I-1a-55)

where Y is equal to $C(R^1)_2$, S, O, C=O or $NR^1$, T is, identically or differently, $C(R^1)_2$, S, O, C=O or $NR^1$, X is selected on each occurrence, identically or differently, from N, P and P=O and is preferably N, and the free positions on the aromatic rings are substituted by radicals $R^2$, where $R^2$ is selected on each occurrence, identically or differently, from H, D, F, CN, $Si(R^3)_3$ or a straight-chain alkyl or alkoxy group having 1 to 20 C atoms or a branched or cyclic alkyl or alkoxy group having 3 to 20 C atoms, each of which may be substituted by one or more radicals $R^3$, where one or more adjacent or non-adjacent $CH_2$ groups may be replaced by —C≡C—, —$R^3$C=C$R^3$—, $Si(R^3)_2$, C=O, C=$NR^3$, $NR^3$, —O—, —S—, —COO— or —CON$R^3$—, or an aryl or heteroaryl group having 5 to 30 aromatic ring atoms, which may in each case be substituted by one or more radicals $R^3$.

The said preferred and particularly preferred embodiments can be combined with one another as desired in accordance with the invention.

It is particularly preferred in the compounds according to the invention for both X to be equal to N and for Y and T to be selected on each occurrence, identically or differently, from $C(R^1)_2$ and a single bond and also for Z to be equal to $CR^2$ or C.

Examples of preferred embodiments of the compounds according to the invention are the compounds shown below:

1

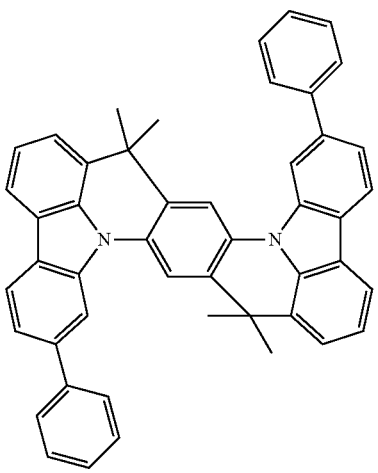

2

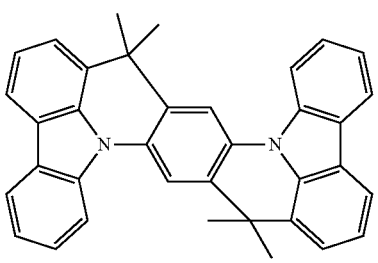

3

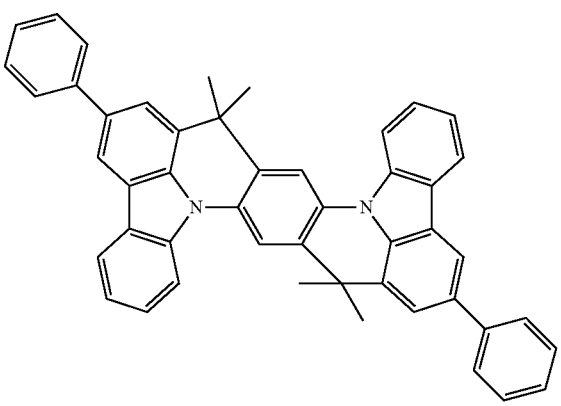

-continued
4
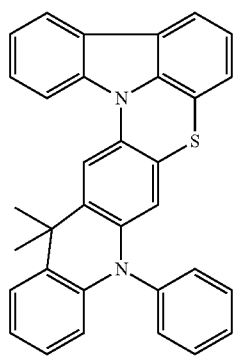
5
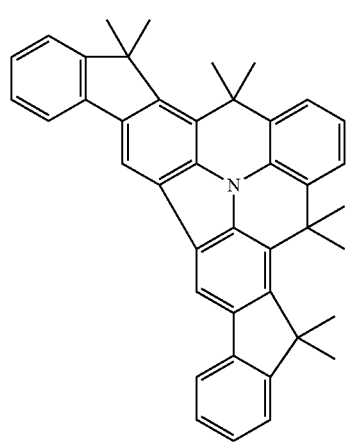
6
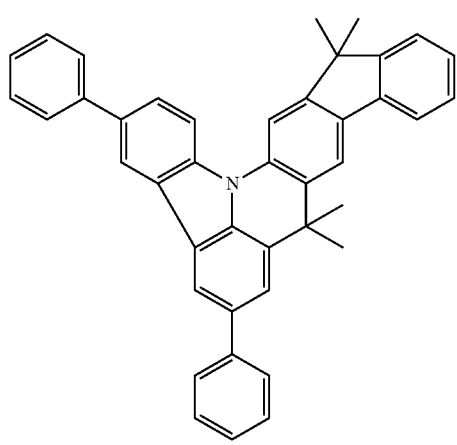
7
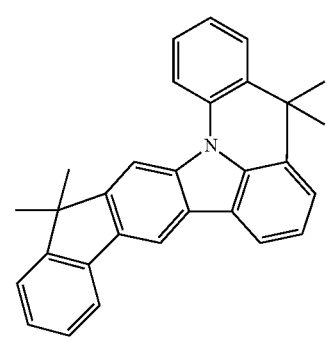
-continued
8
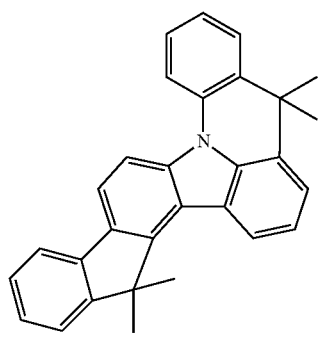
9
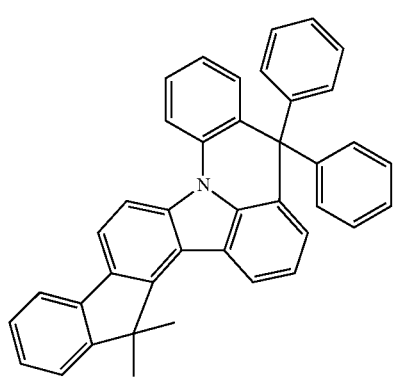
10
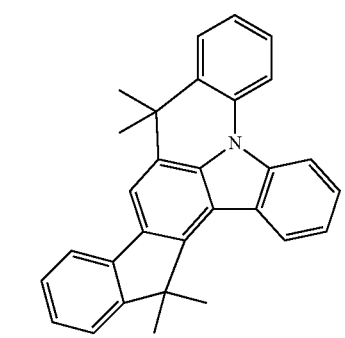
11
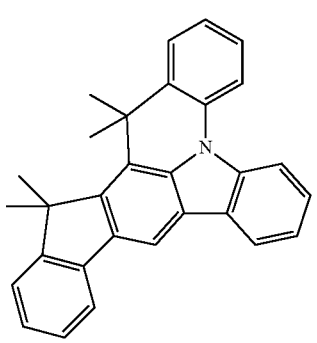

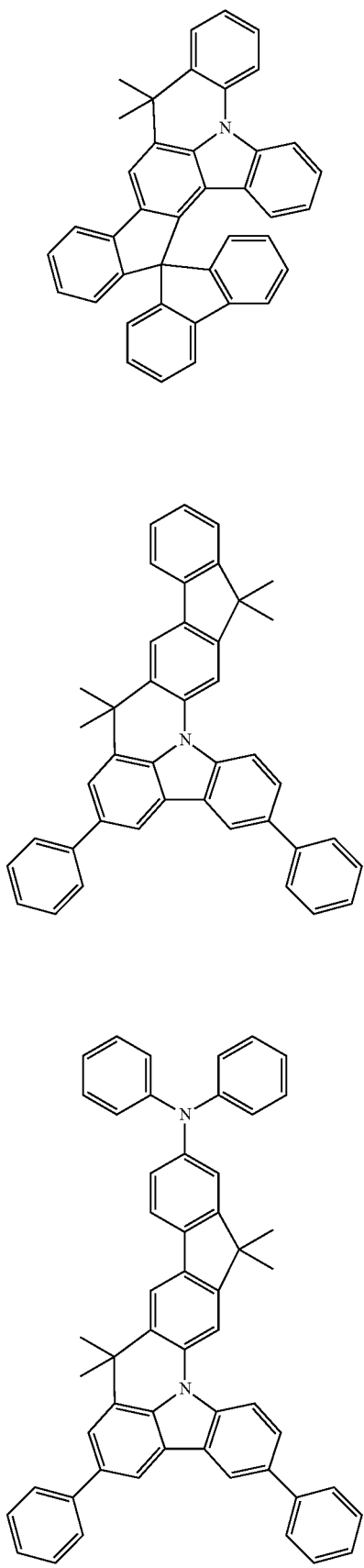
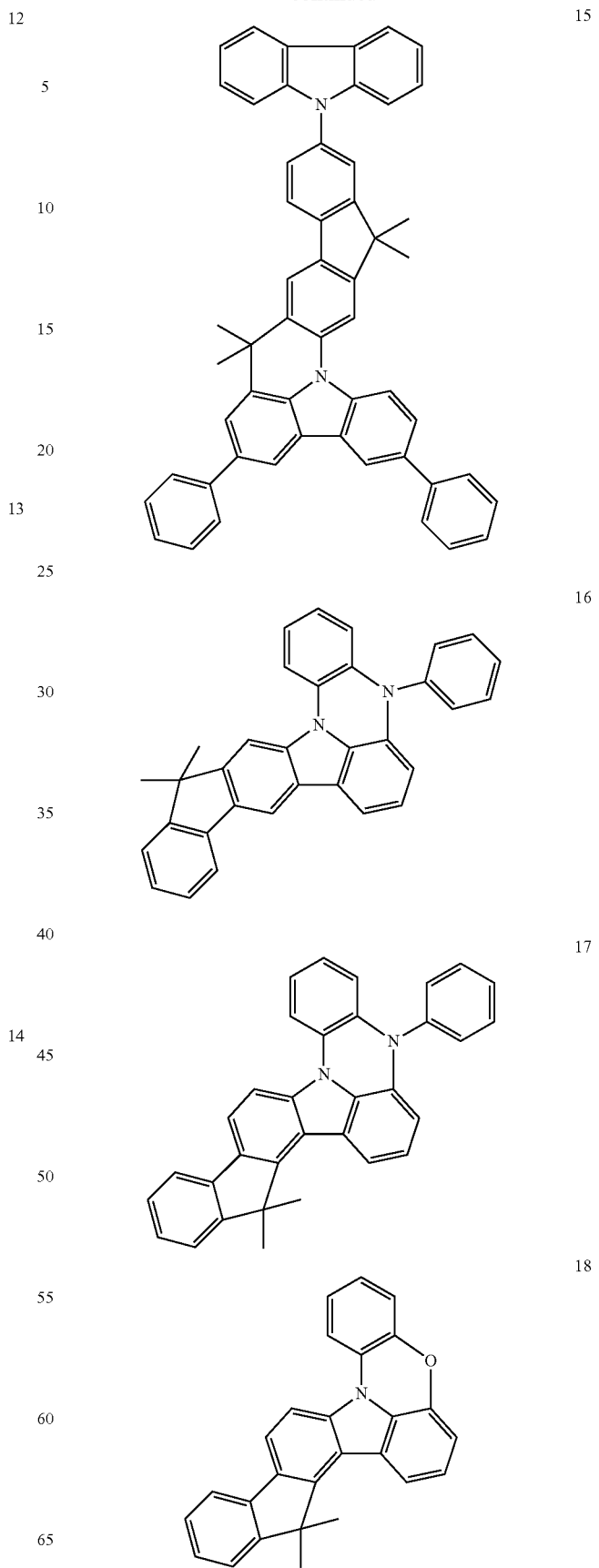

-continued
19
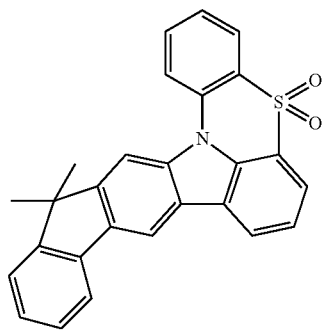
20
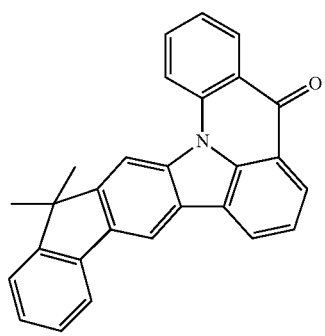
21
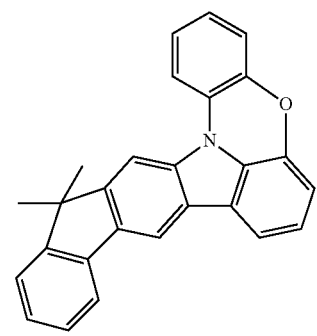
22
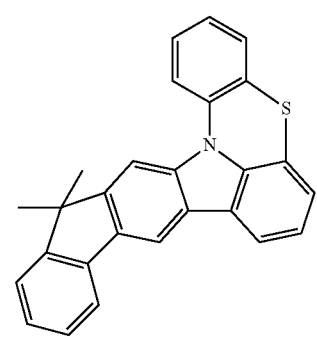
23
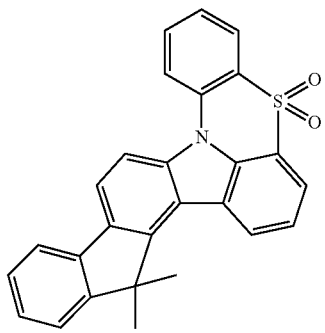
24
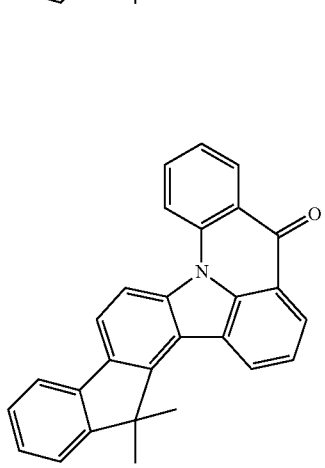
25
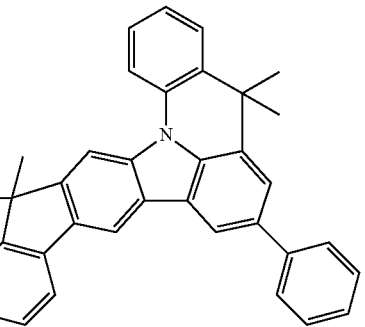
26
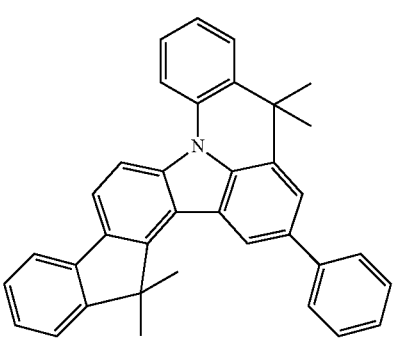

-continued
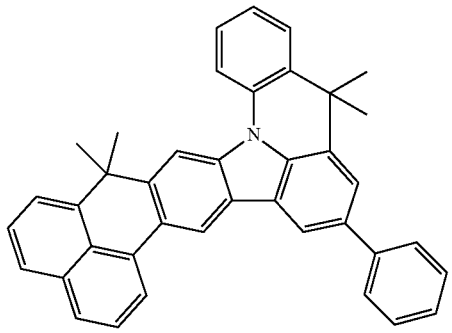
27
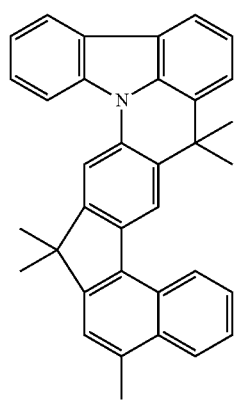
28
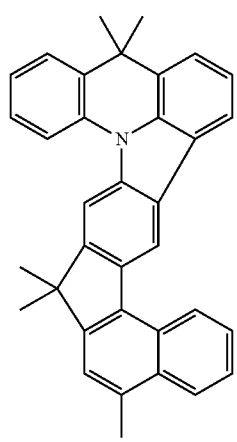
29
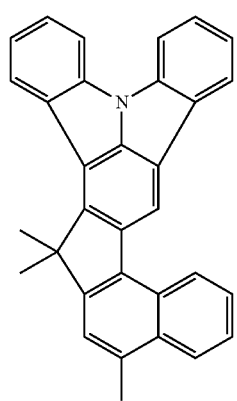
30
-continued
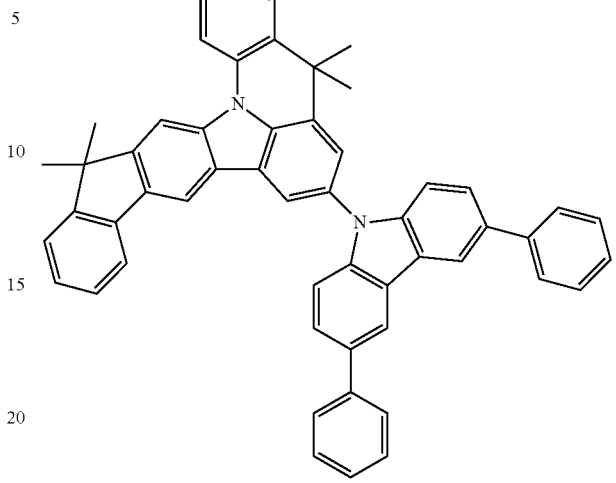
31
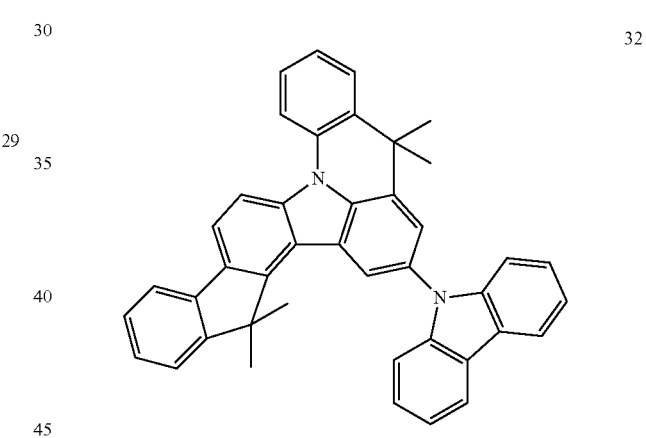
32
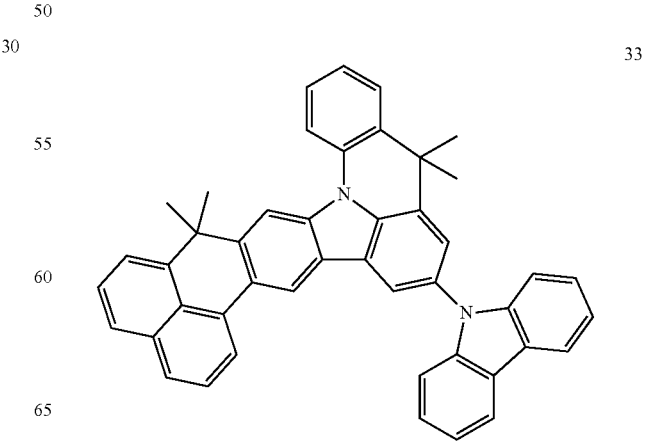
33

34
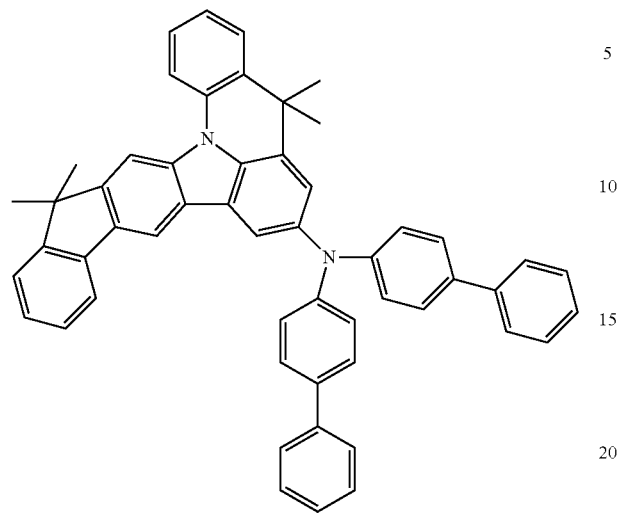
35
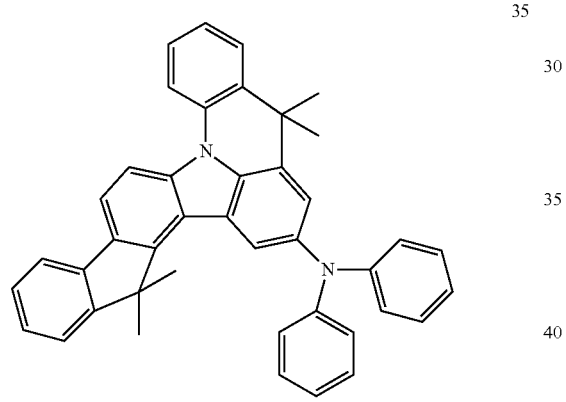
36
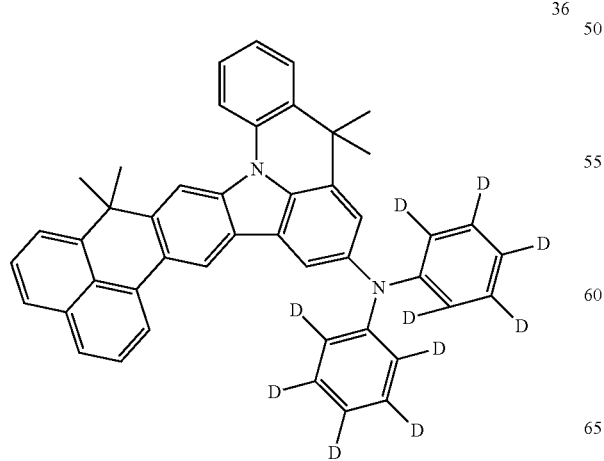
37
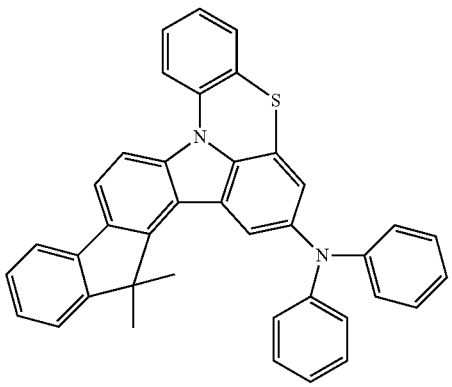
38
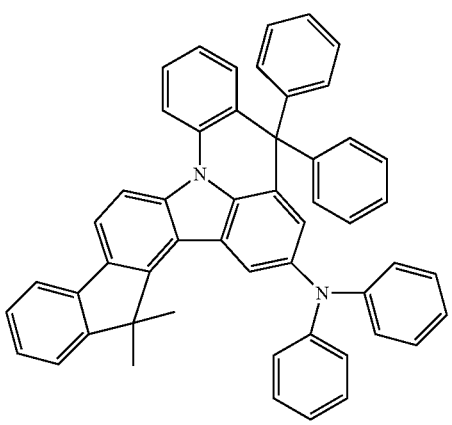
39
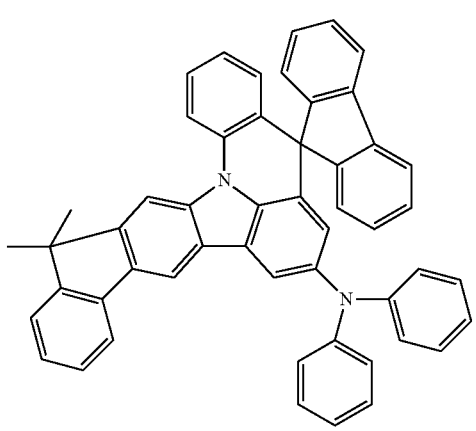

-continued
40
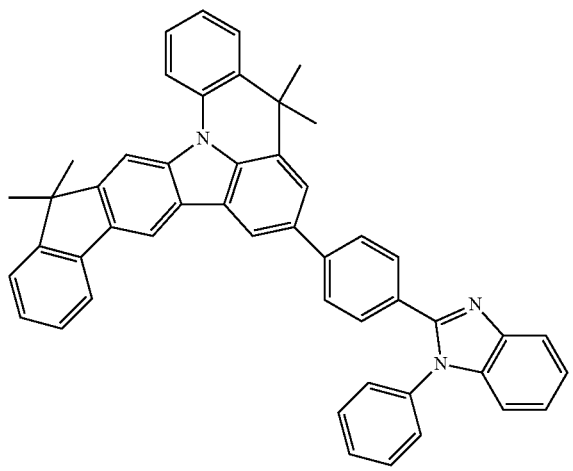
41
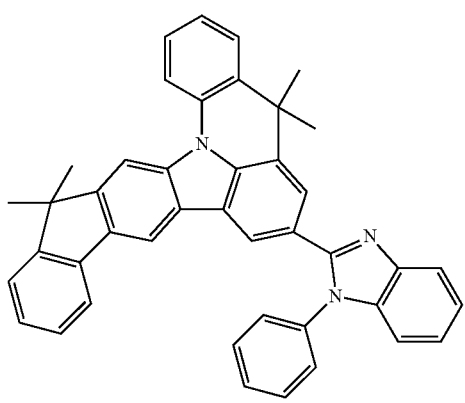
42
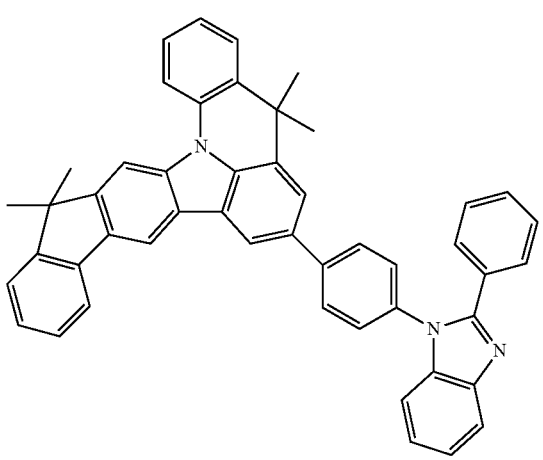
-continued
43
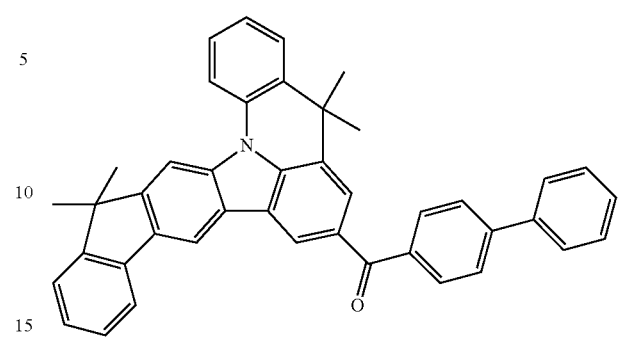
44
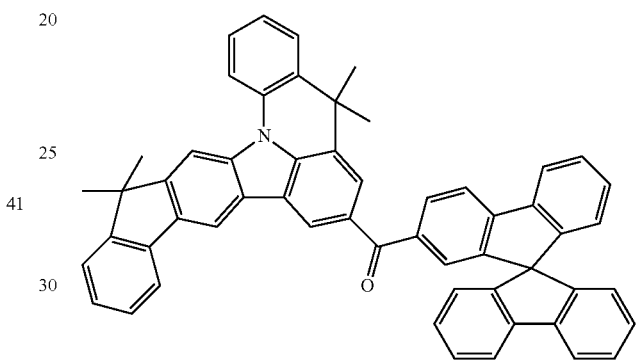
45
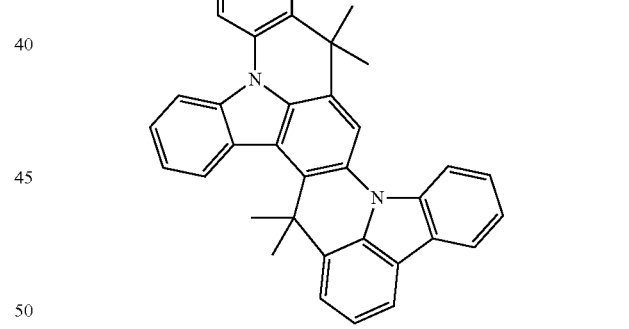
46
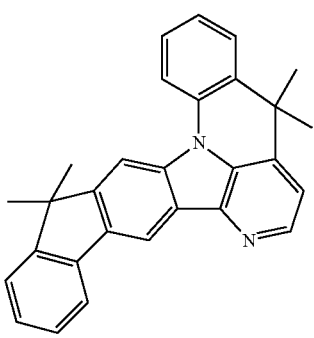

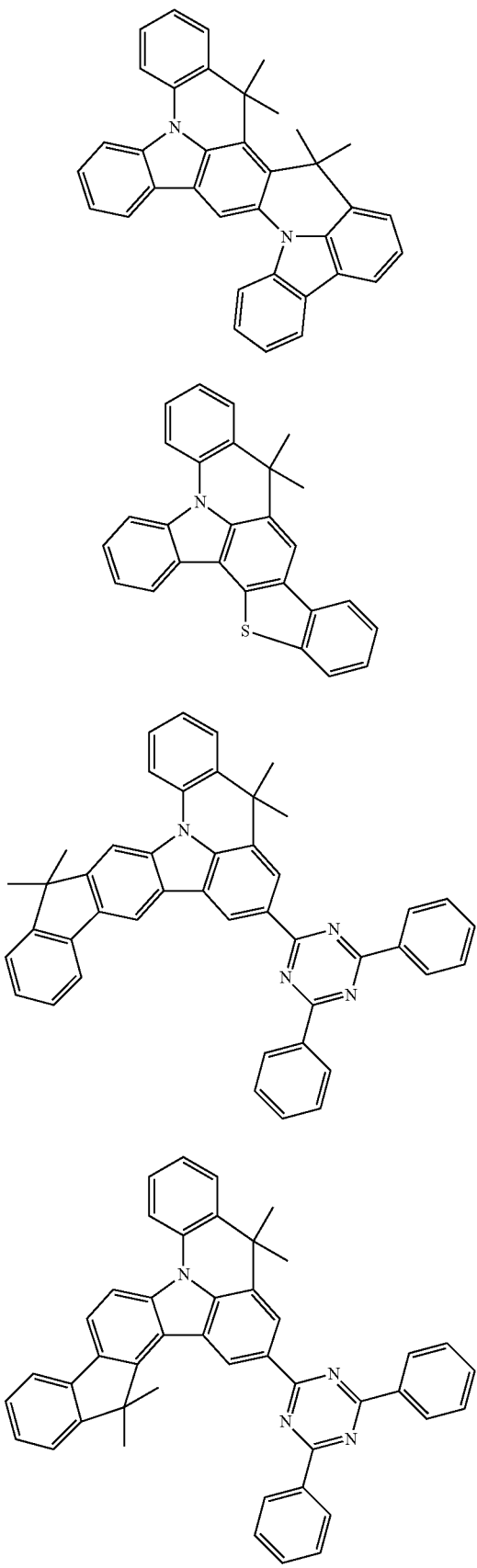
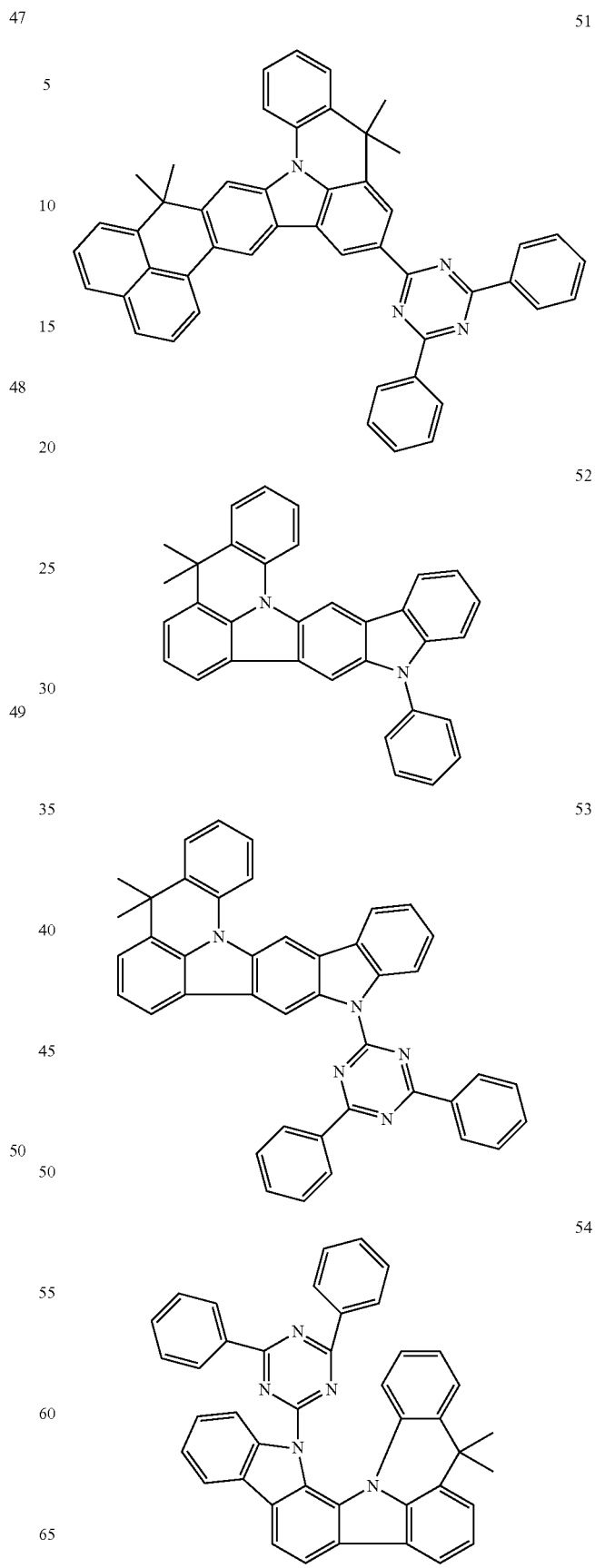

55
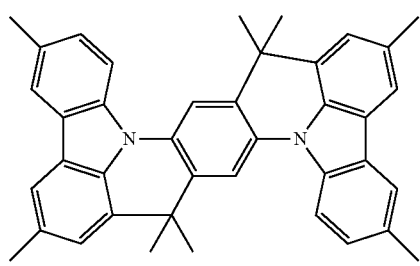
56
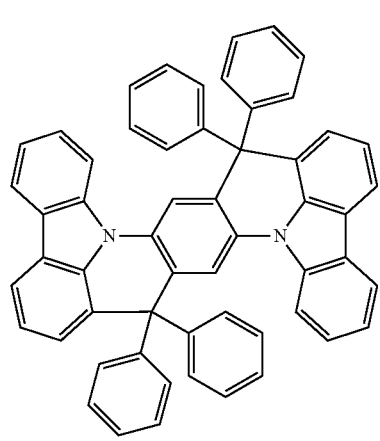
57
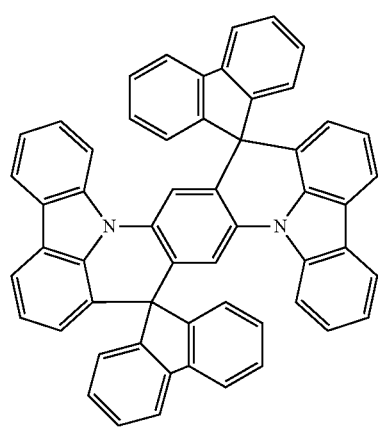
58
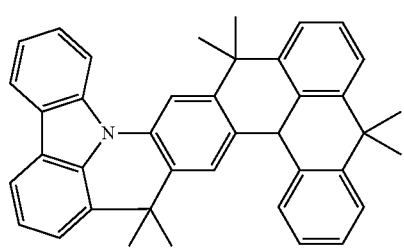
-continued
59
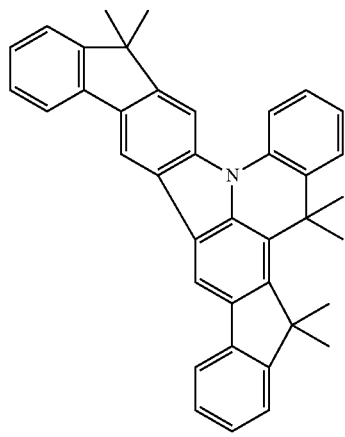
60
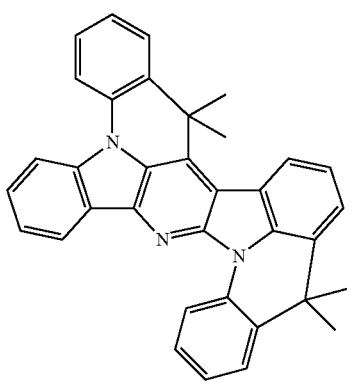
61
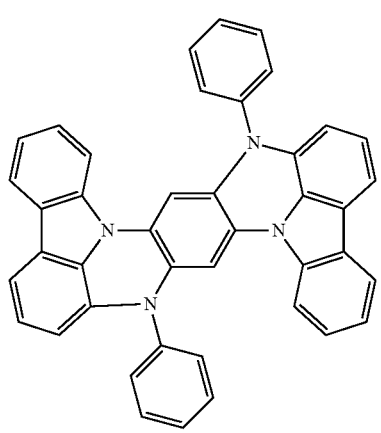
62
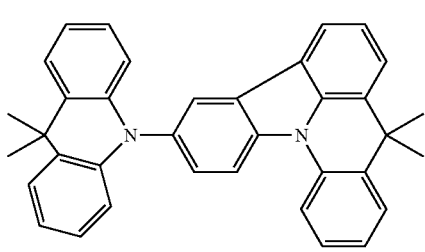

63
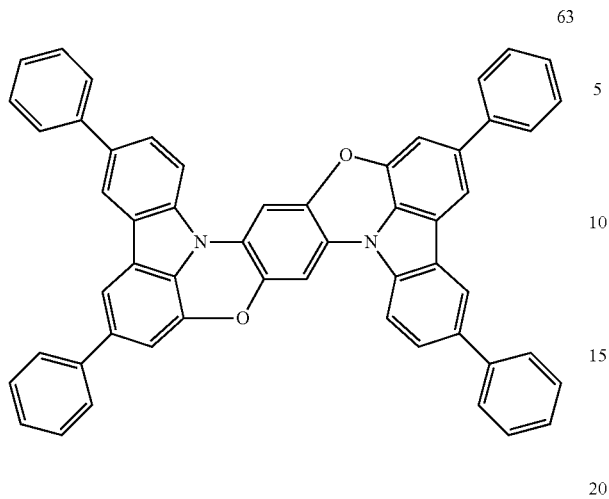
64
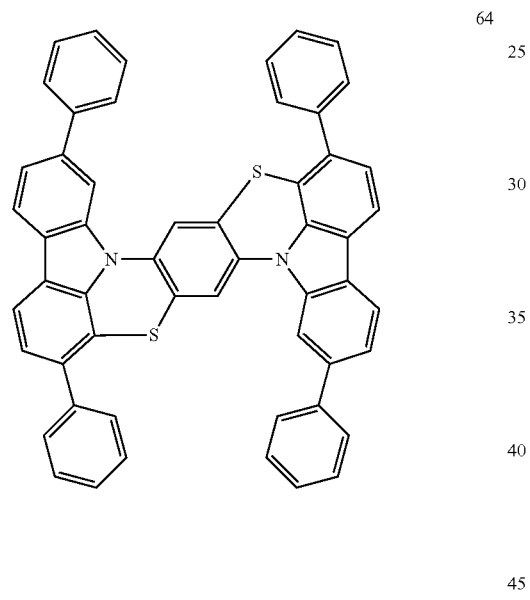
65
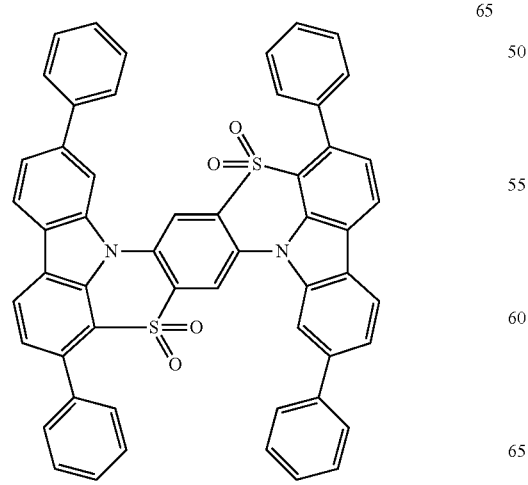
66
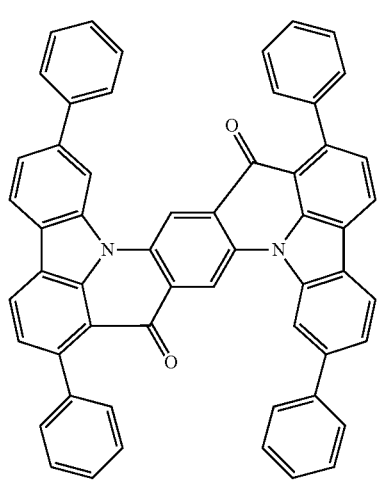
67
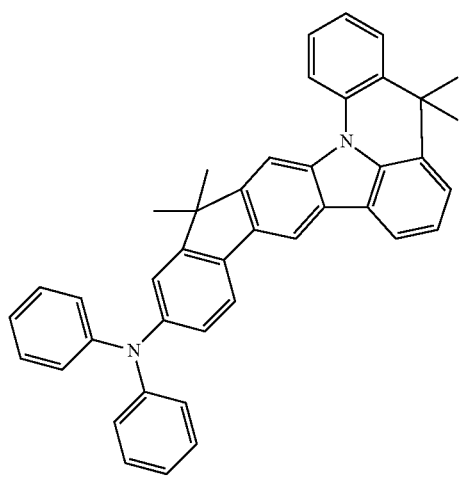
68
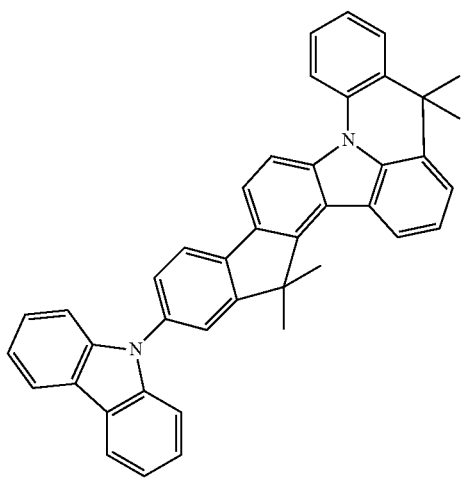

-continued
69
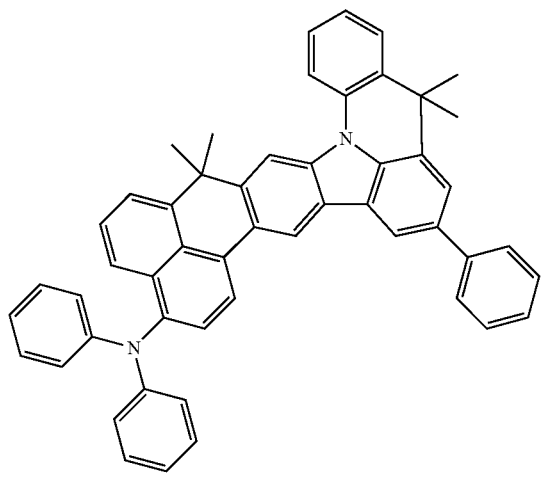
70
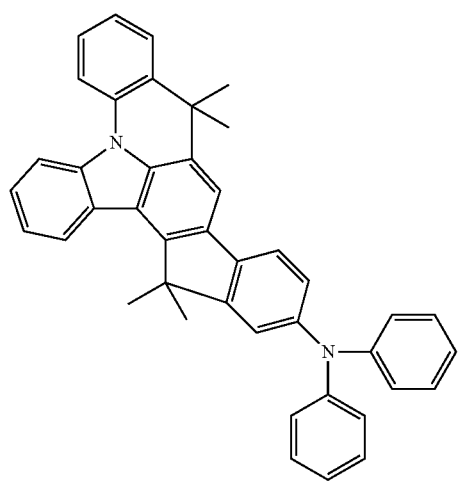
71
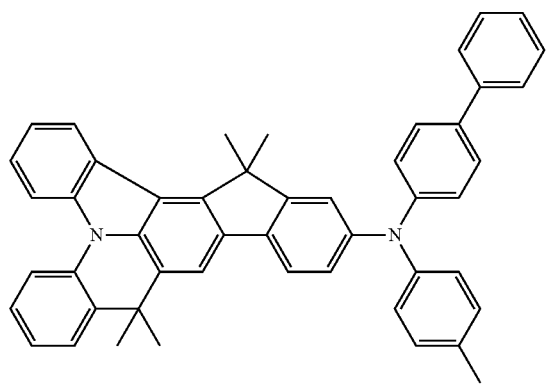
-continued
72
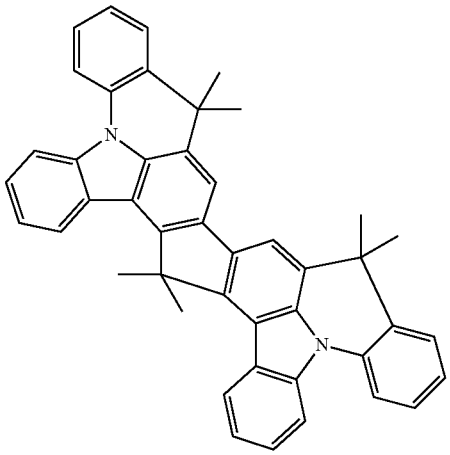
73
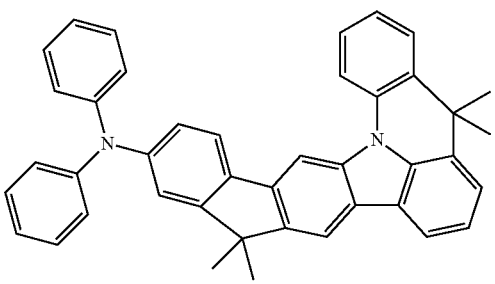
74
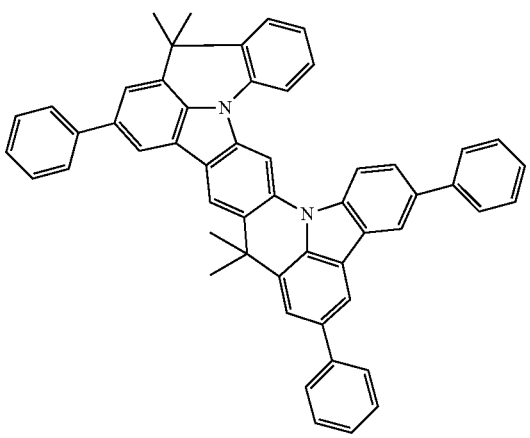
75
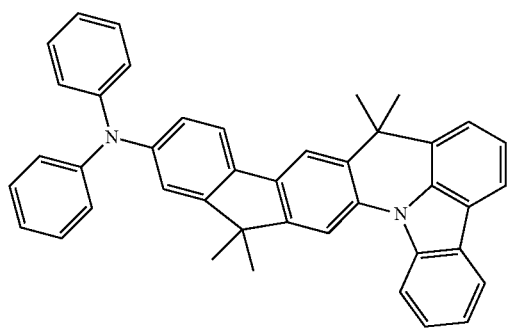

76
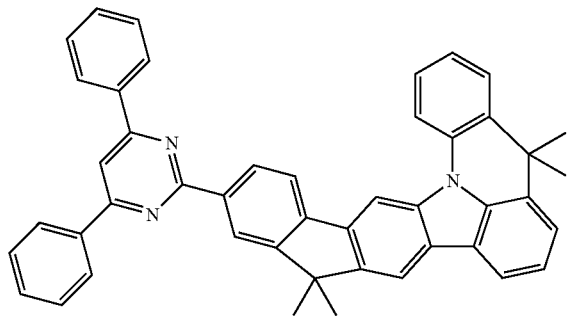
77
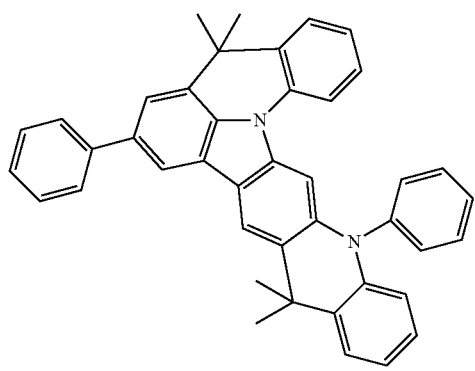
78
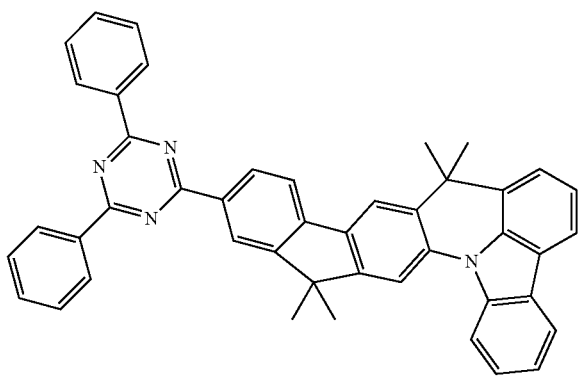
79
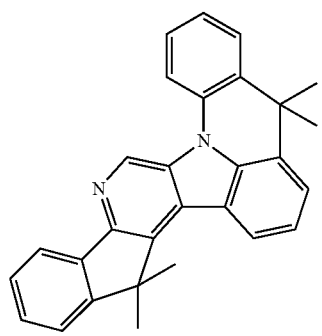
80
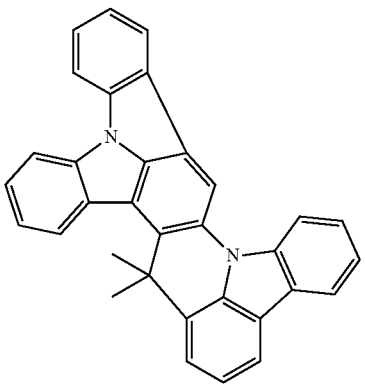
81
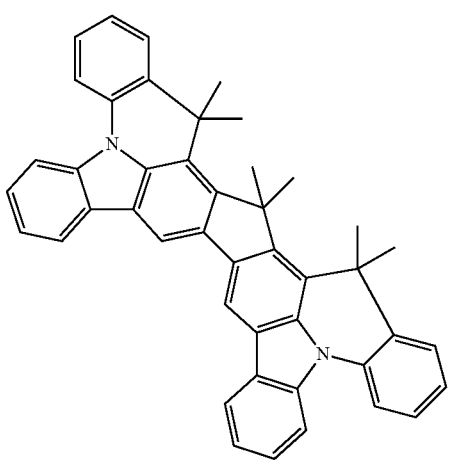
82
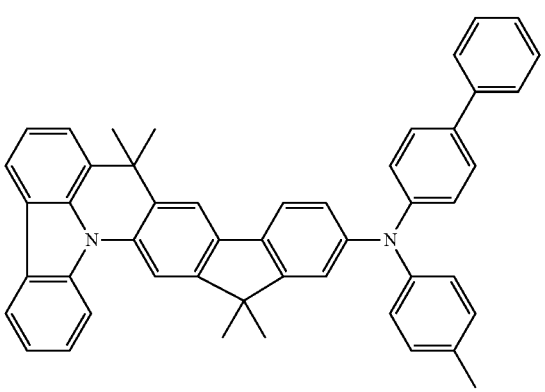
83
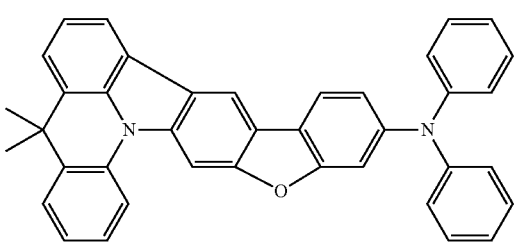

84
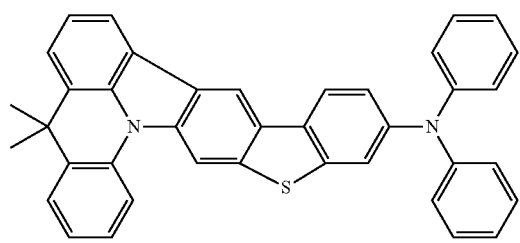
85
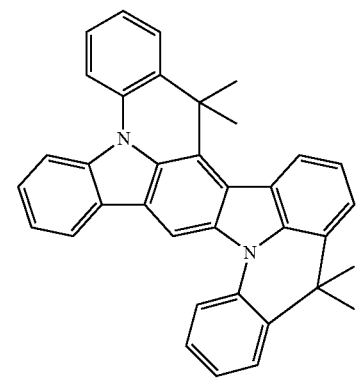
86
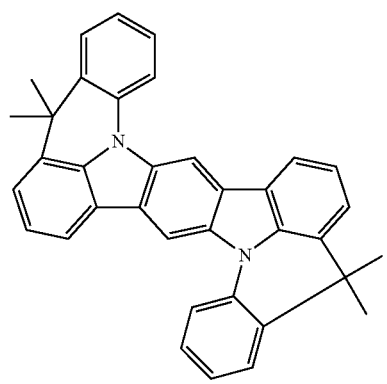
87
88
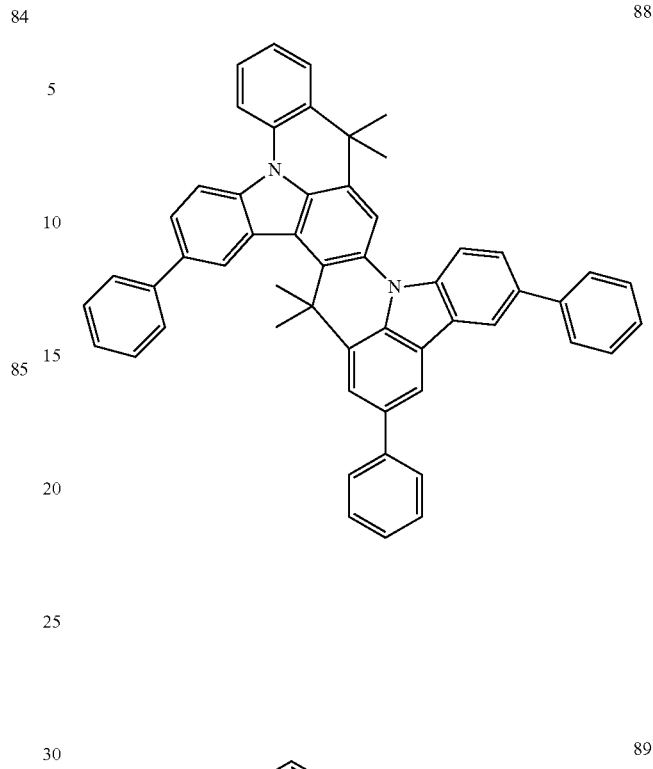
89
90

91
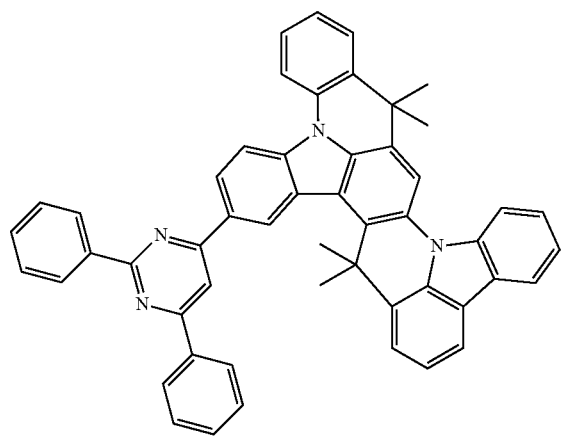
92
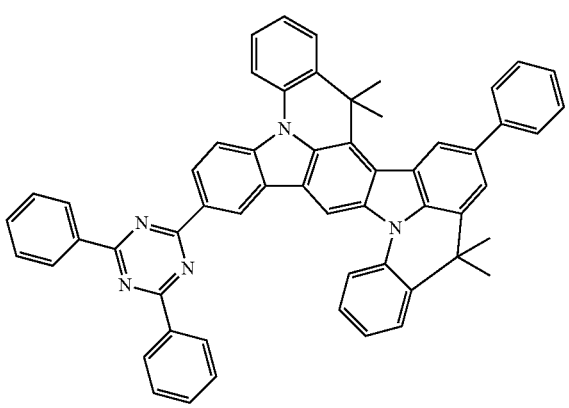
93
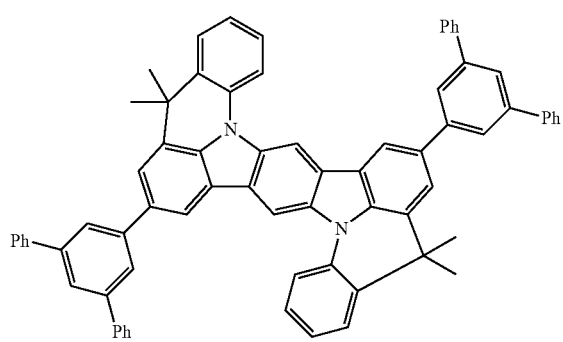
94
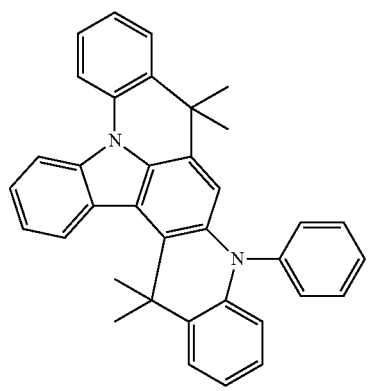
95
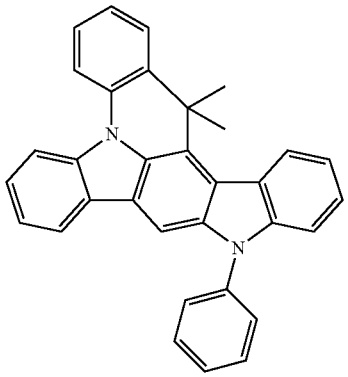
96
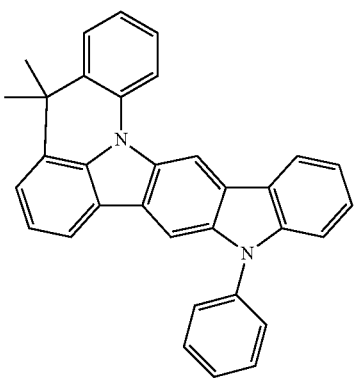
97
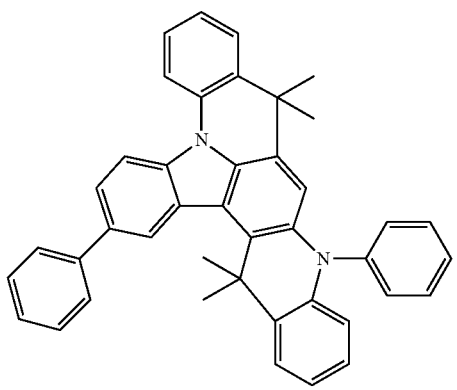
98
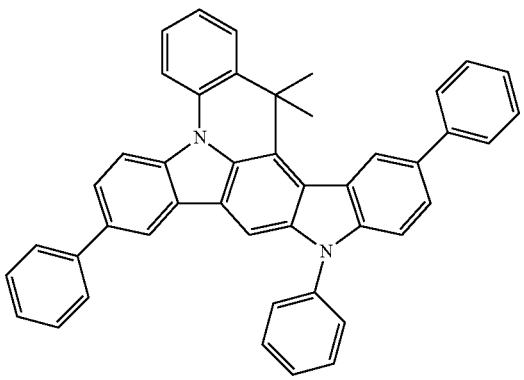

-continued
99
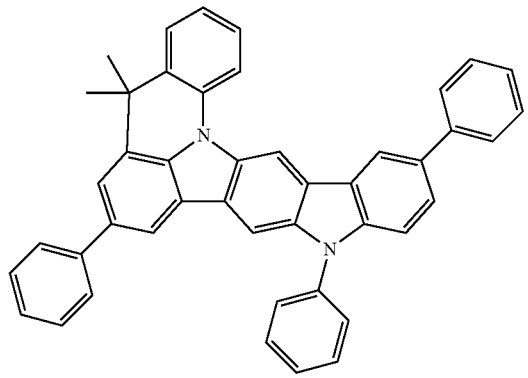
100
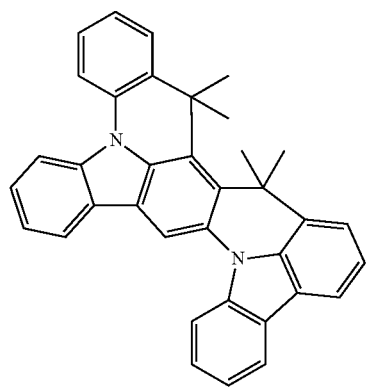
101
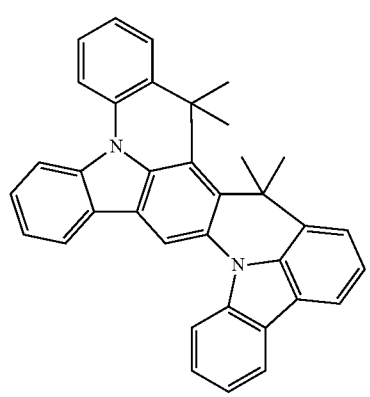
102
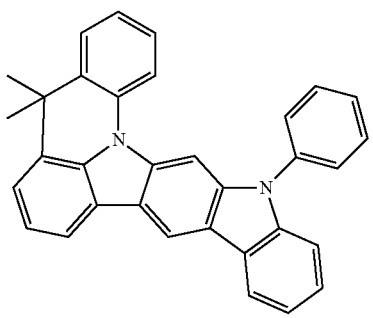
-continued
103
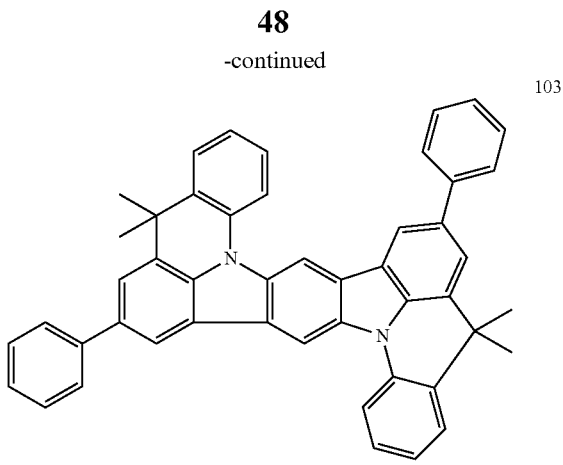
104
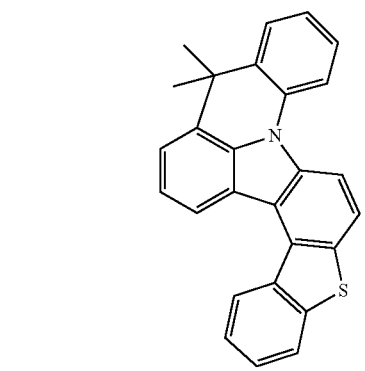
105
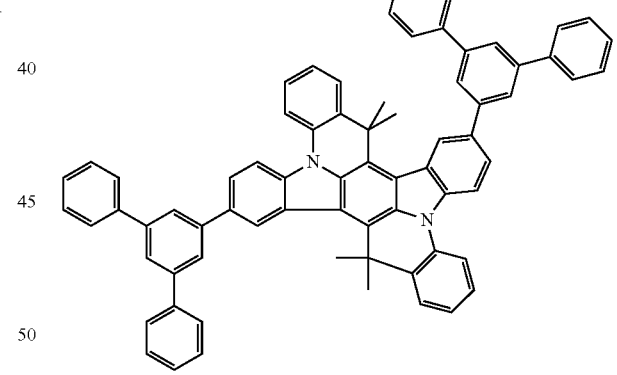
106
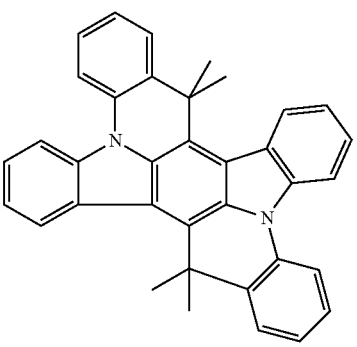

107
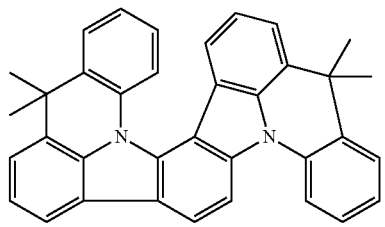
108
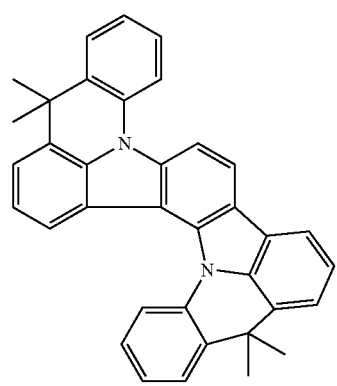
109
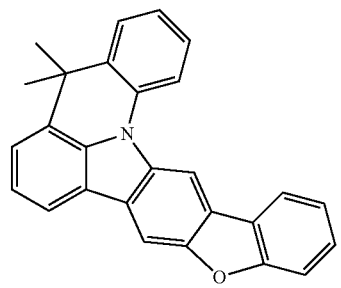
110
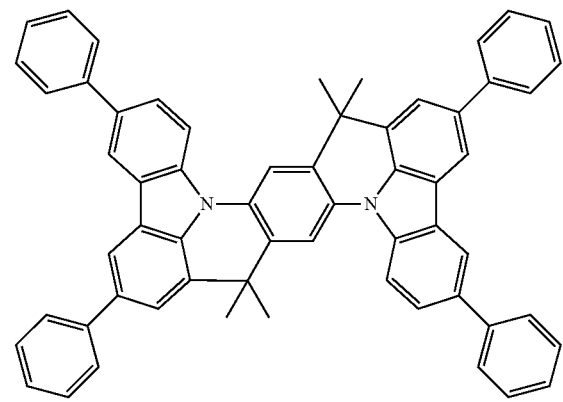
111
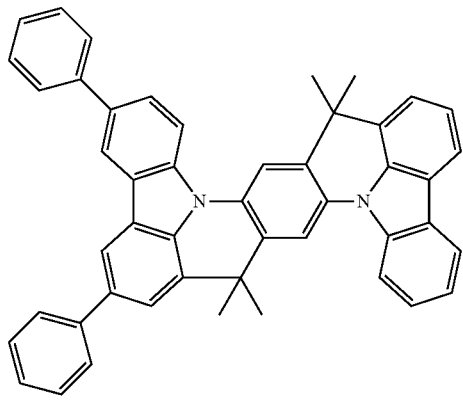
112
113
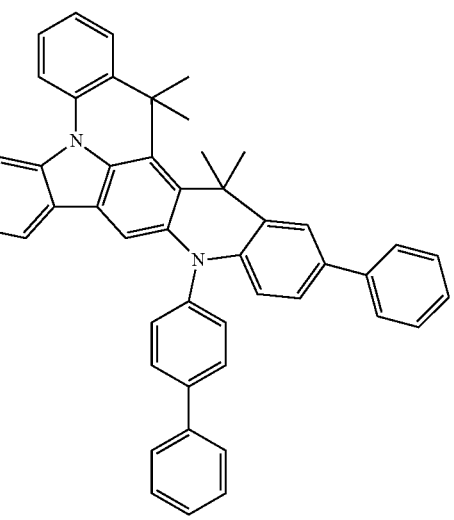

114
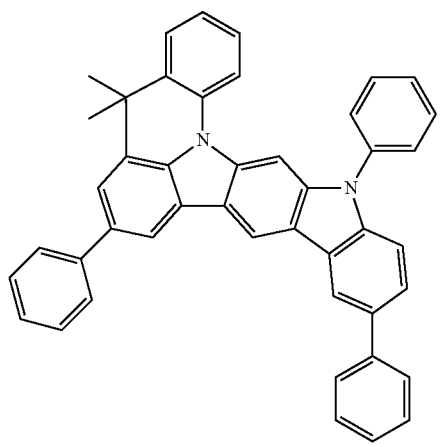
115
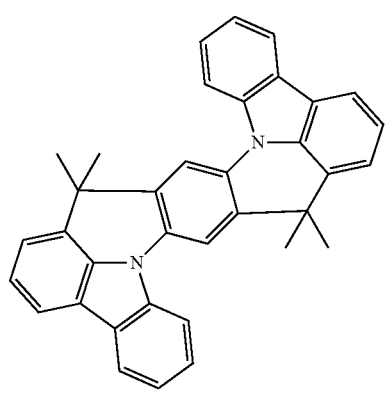
116
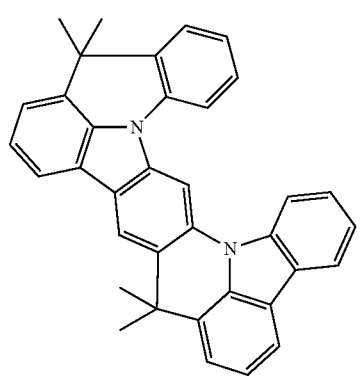
117
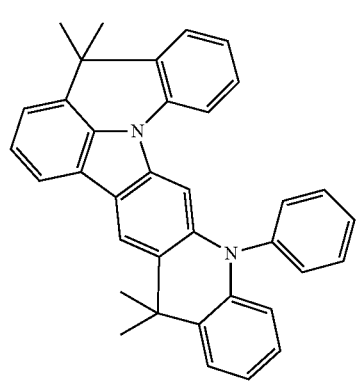
118
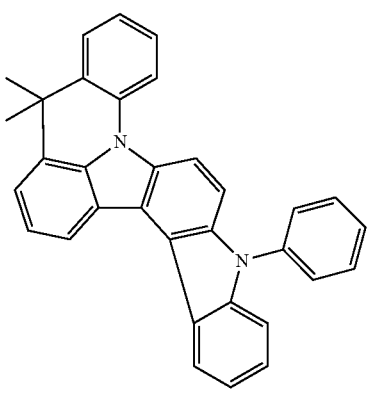
119
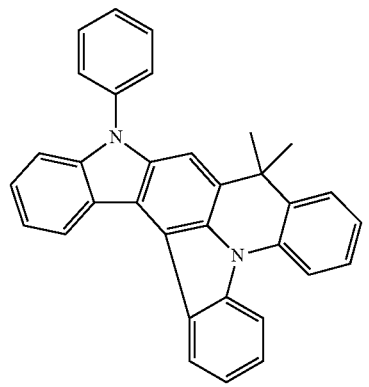
120
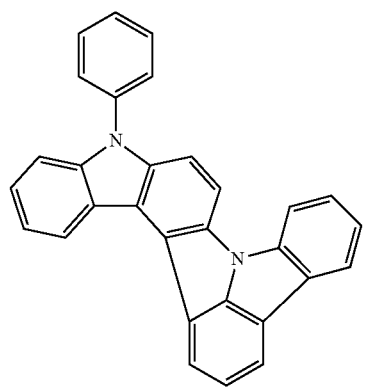

121
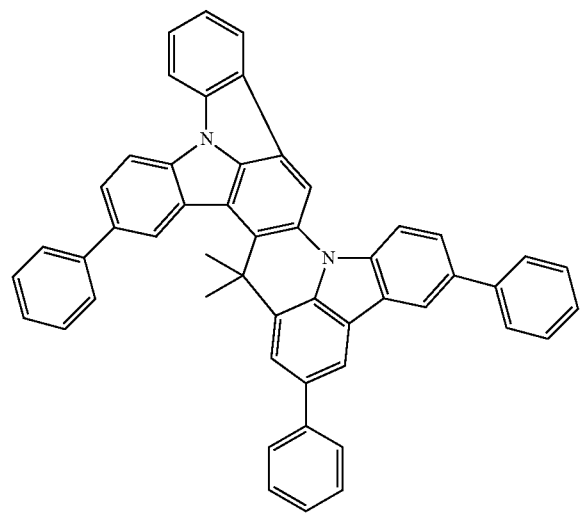
122
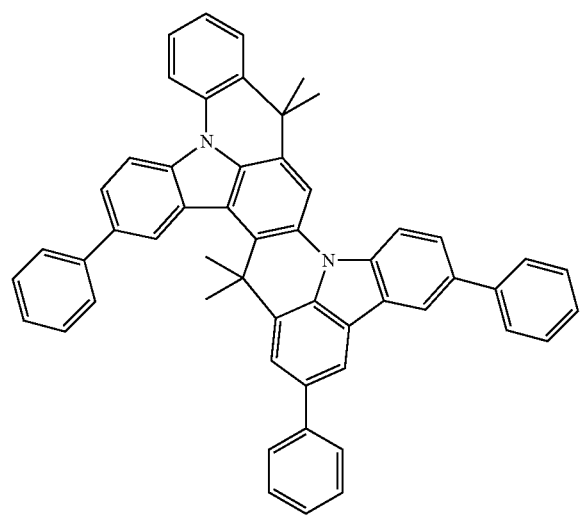
123
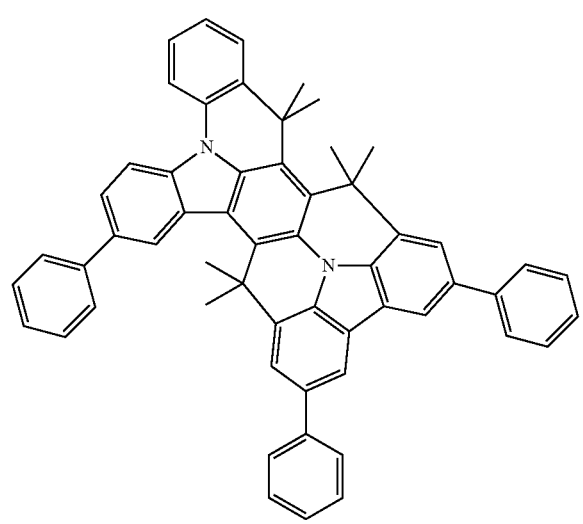
124
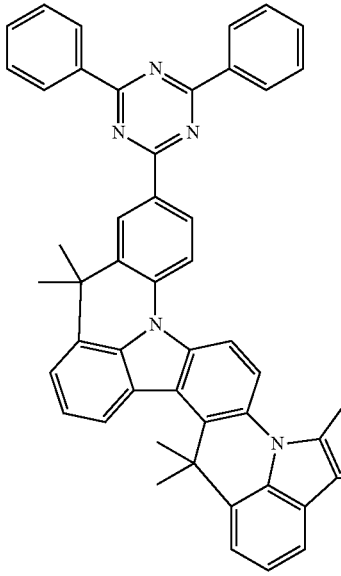
125
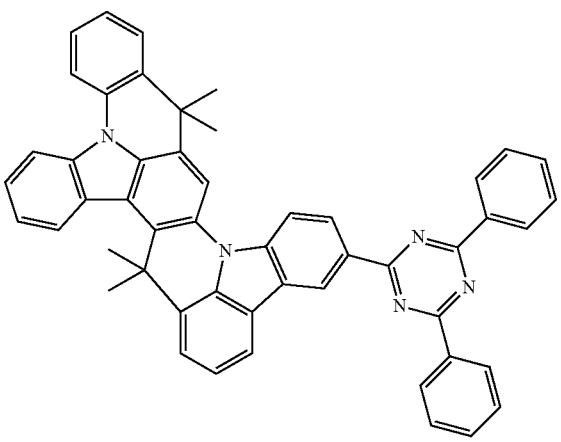
126
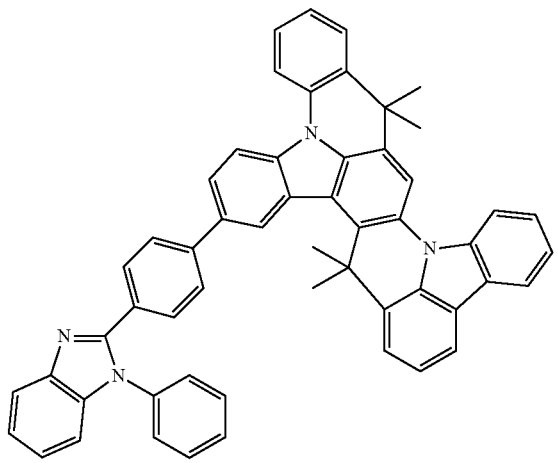

127
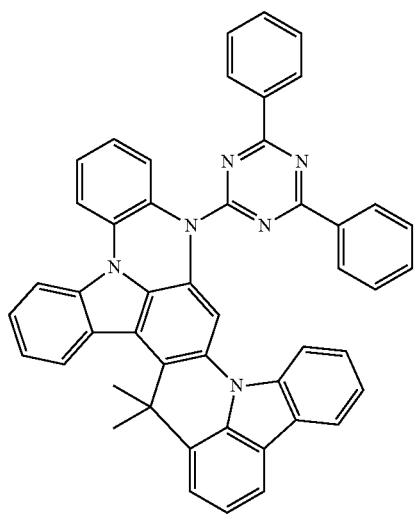
128
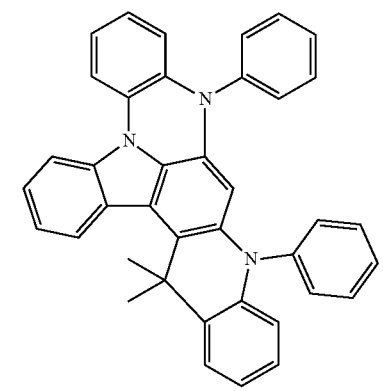
129
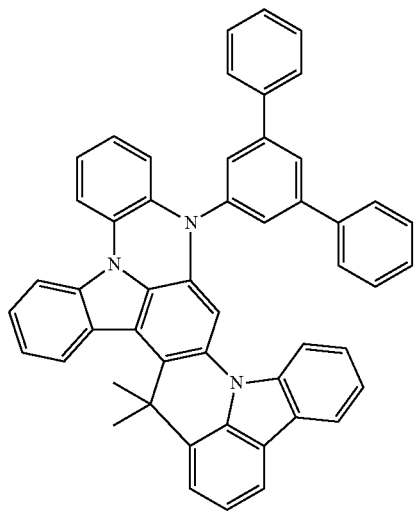
130
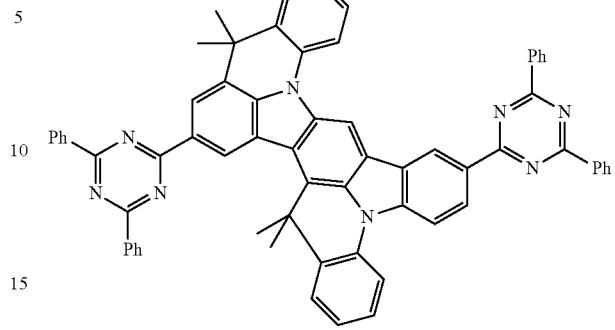
131
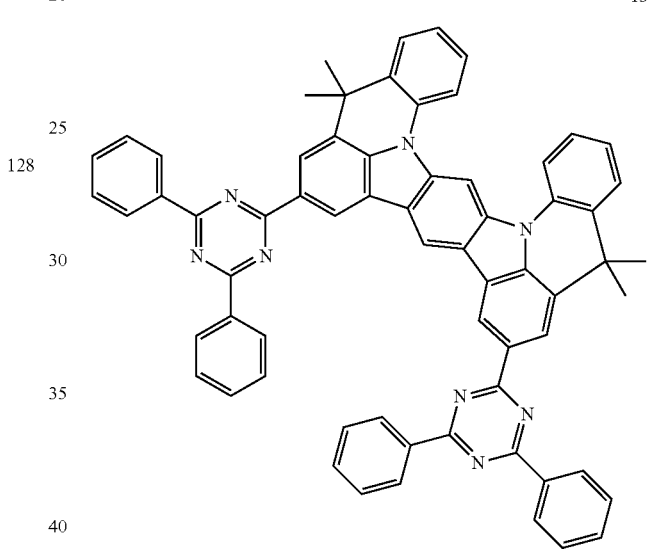
132
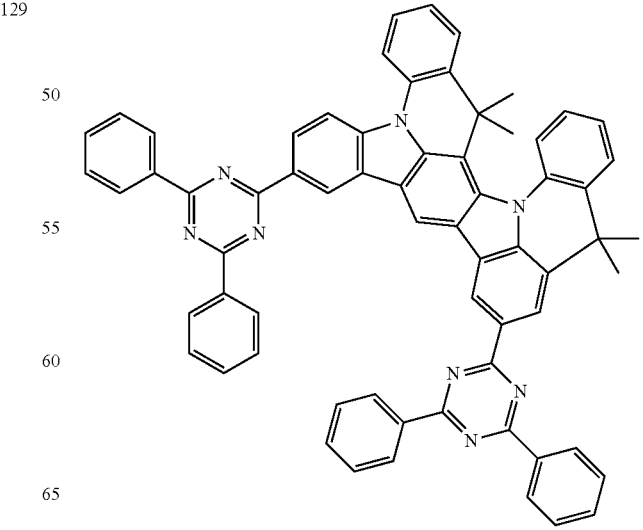

133
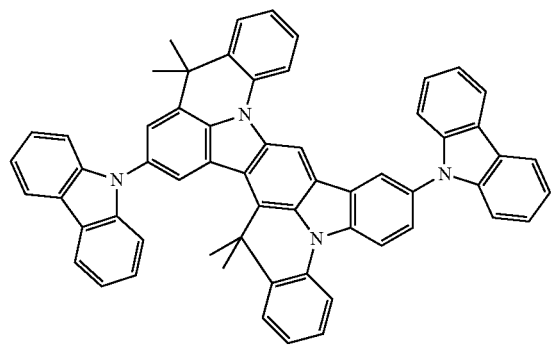
134
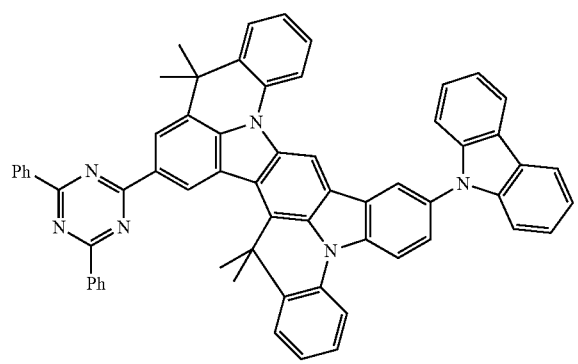
135
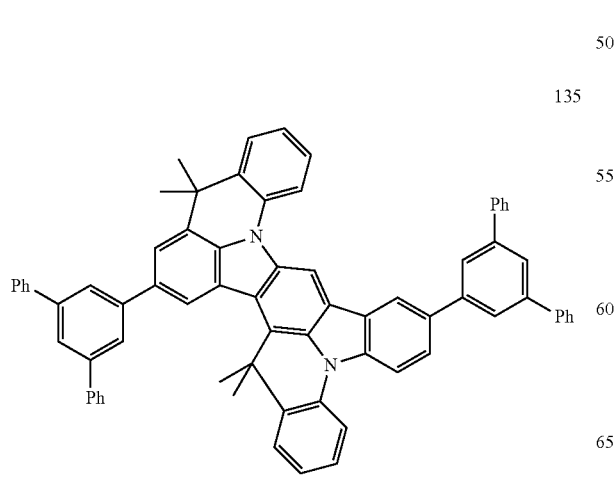
136
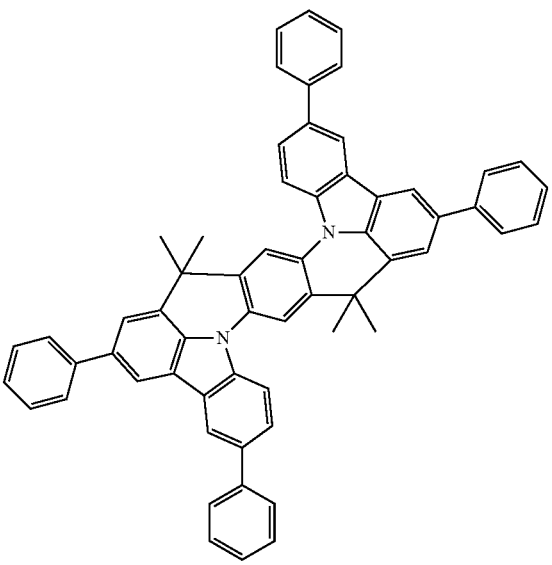
137
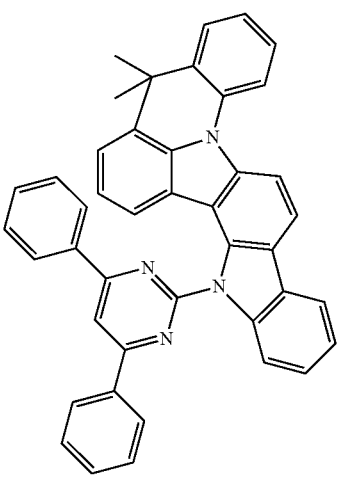
138
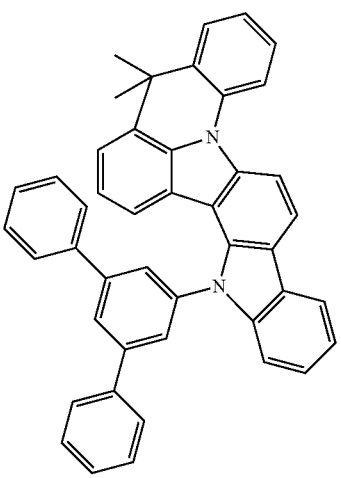

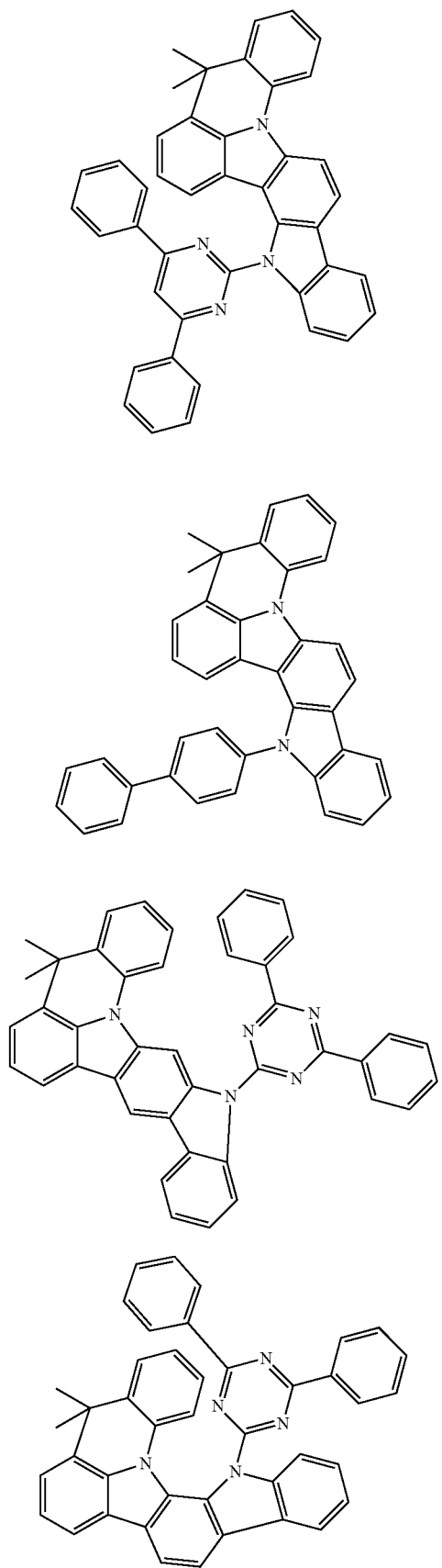
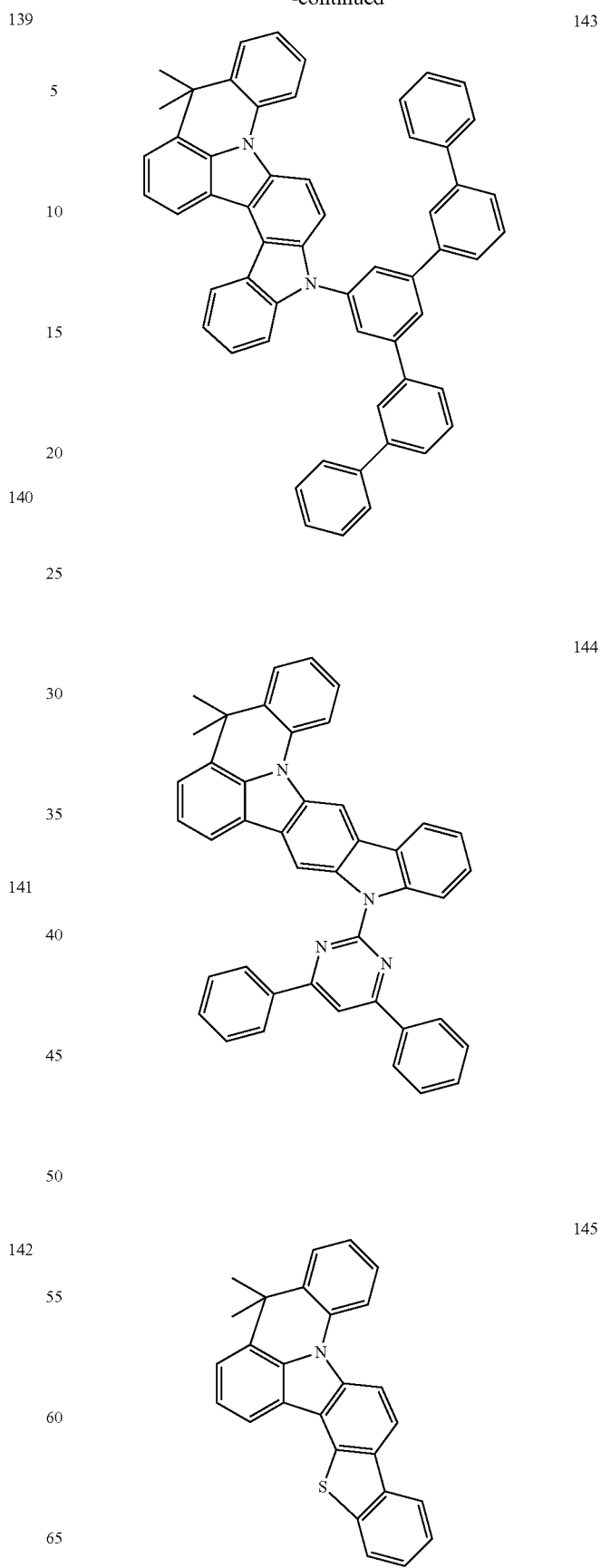

146 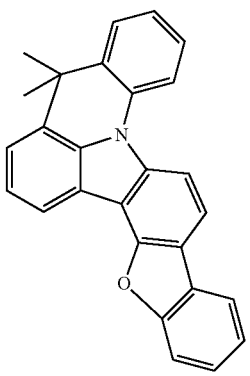

147 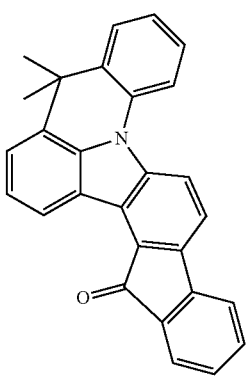

148 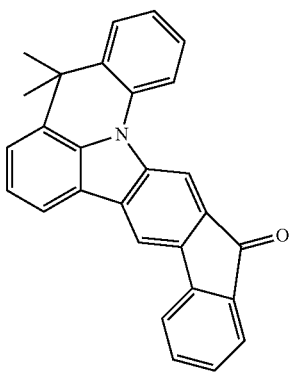

149 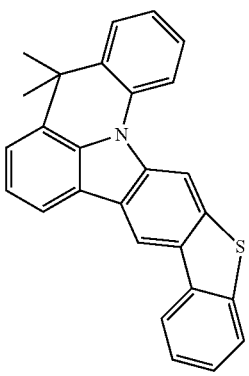

150 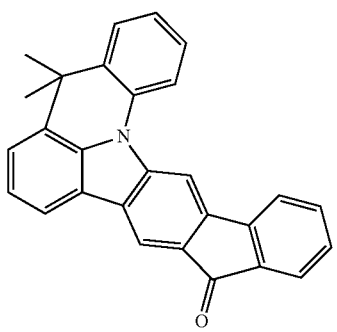

151 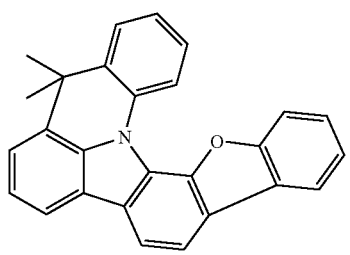

The compounds according to the invention can be prepared by processes known to the person skilled in the art, such as, for example, metal-catalysed cross-coupling reactions and acid-catalysed ring-closure reactions.

Scheme 1 below shows the synthesis of various bridged triarylamine units (A-E), which are important intermediates in the synthesis of the compounds according to the invention. The corresponding phosphine and phosphine oxide analogues can also be prepared analogously.

R and R' in the schemes generally stand for a radical as defined above by $R^1$ and $R^2$.

Scheme 1

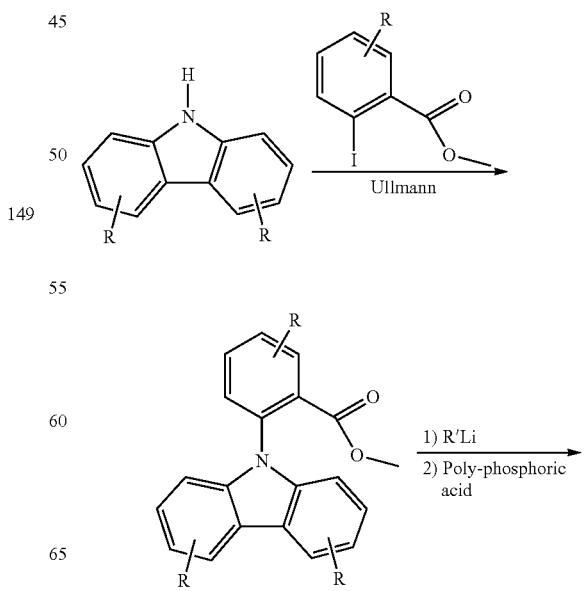

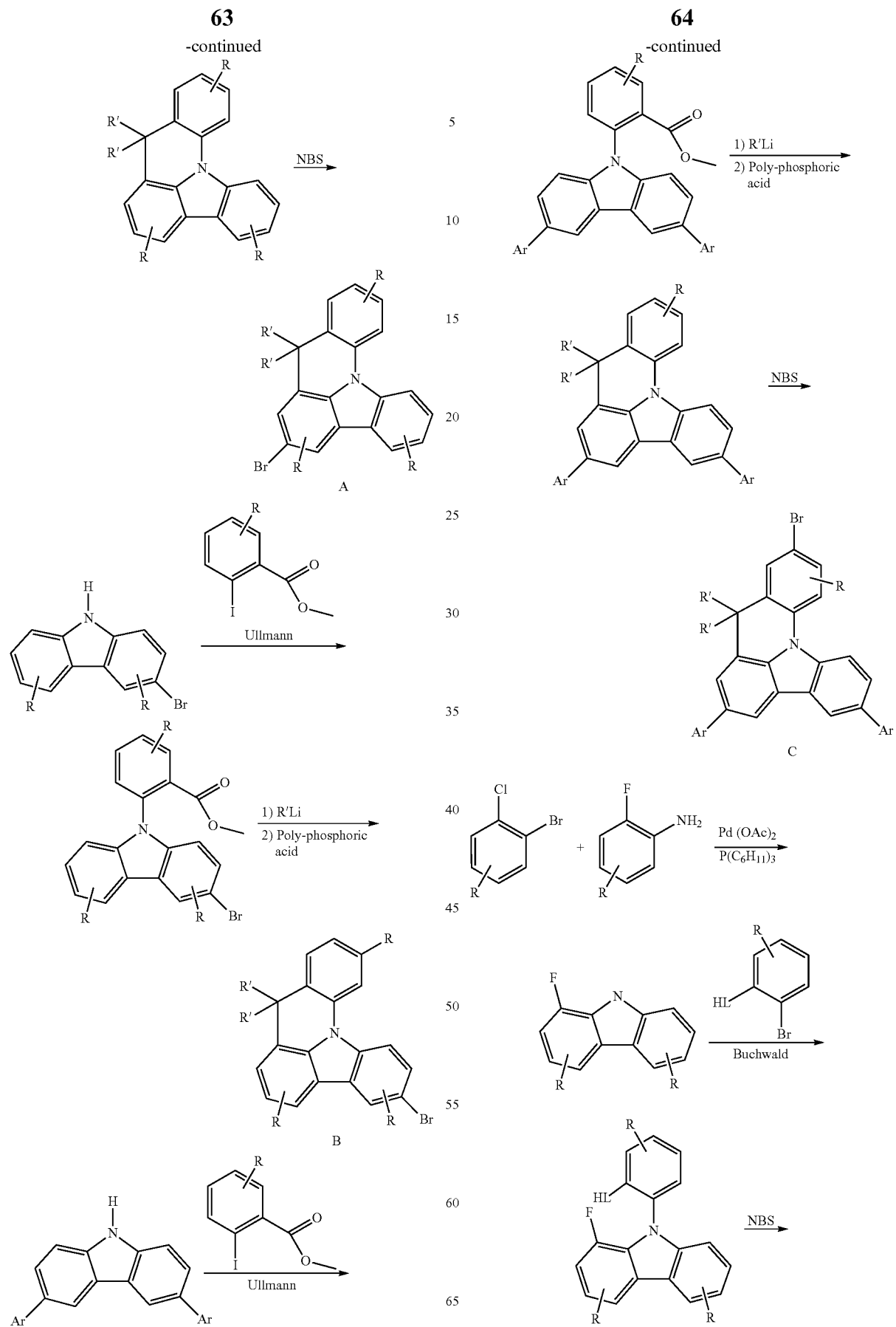

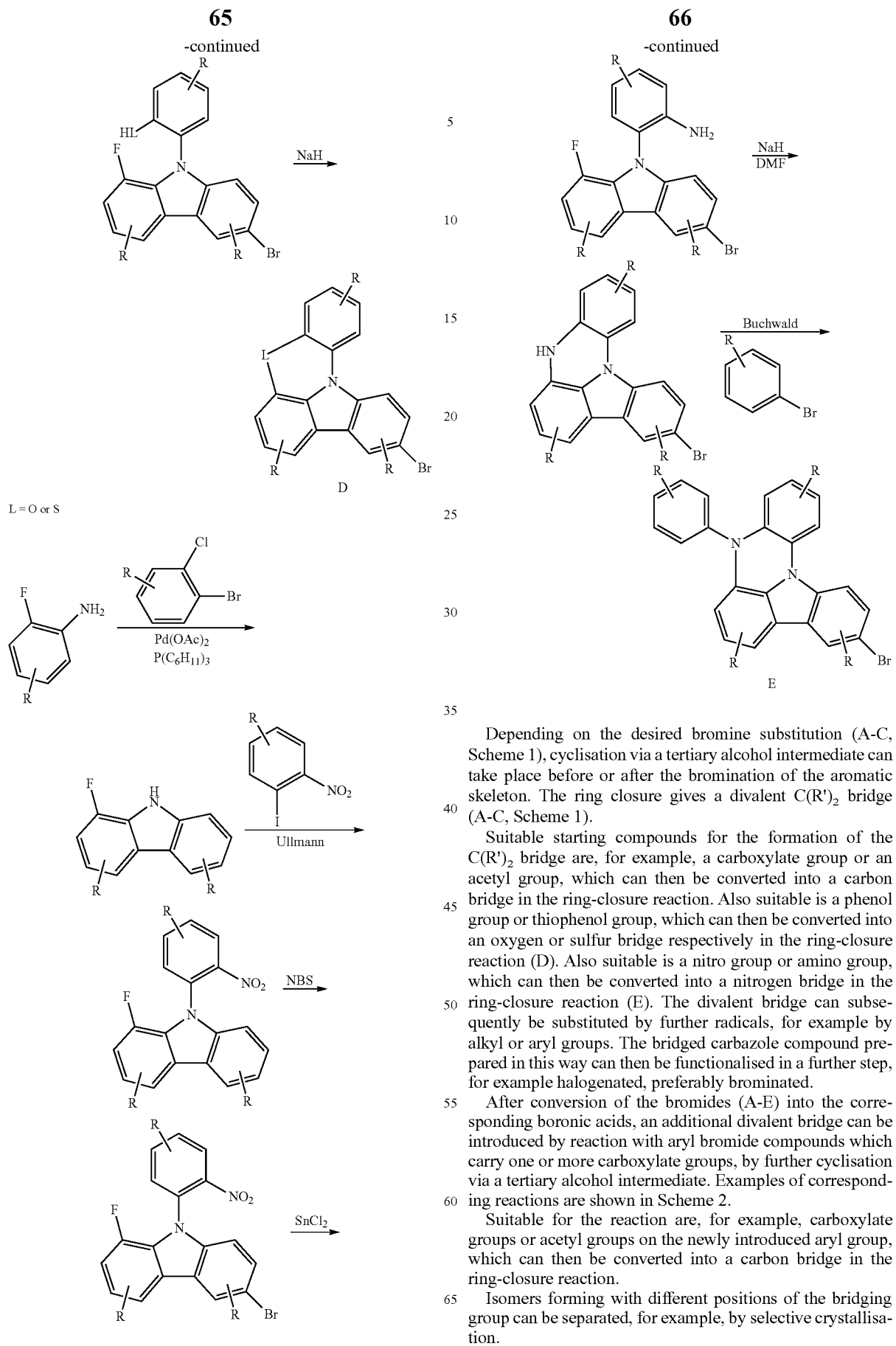

Depending on the desired bromine substitution (A-C, Scheme 1), cyclisation via a tertiary alcohol intermediate can take place before or after the bromination of the aromatic skeleton. The ring closure gives a divalent C(R')$_2$ bridge (A-C, Scheme 1).

Suitable starting compounds for the formation of the C(R')$_2$ bridge are, for example, a carboxylate group or an acetyl group, which can then be converted into a carbon bridge in the ring-closure reaction. Also suitable is a phenol group or thiophenol group, which can then be converted into an oxygen or sulfur bridge respectively in the ring-closure reaction (D). Also suitable is a nitro group or amino group, which can then be converted into a nitrogen bridge in the ring-closure reaction (E). The divalent bridge can subsequently be substituted by further radicals, for example by alkyl or aryl groups. The bridged carbazole compound prepared in this way can then be functionalised in a further step, for example halogenated, preferably brominated.

After conversion of the bromides (A-E) into the corresponding boronic acids, an additional divalent bridge can be introduced by reaction with aryl bromide compounds which carry one or more carboxylate groups, by further cyclisation via a tertiary alcohol intermediate. Examples of corresponding reactions are shown in Scheme 2.

Suitable for the reaction are, for example, carboxylate groups or acetyl groups on the newly introduced aryl group, which can then be converted into a carbon bridge in the ring-closure reaction.

Isomers forming with different positions of the bridging group can be separated, for example, by selective crystallisation.

Scheme 2
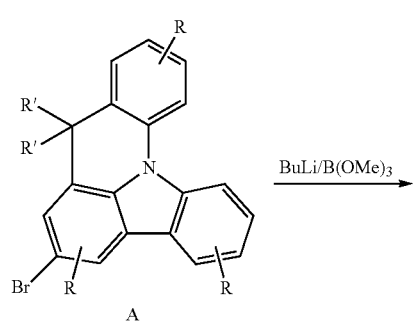
A
BuLi/B(OMe)₃ →
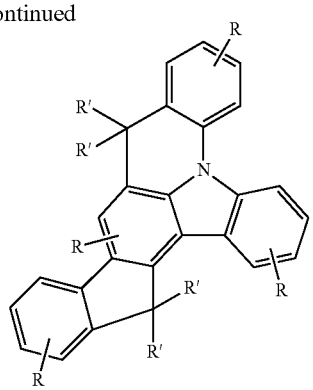
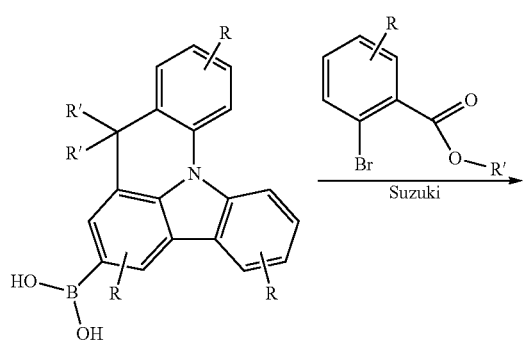
Suzuki →
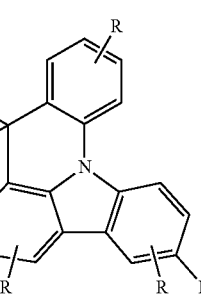
B
BuLi/B(OMe)₃ →
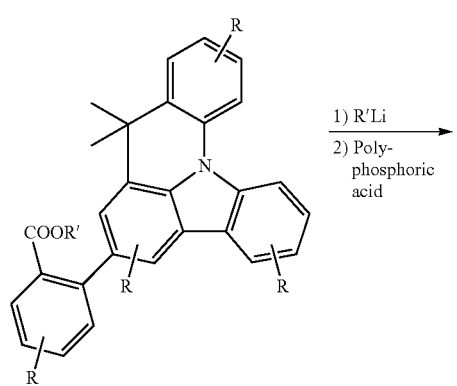
1) R'Li
2) Polyphosphoric acid
→
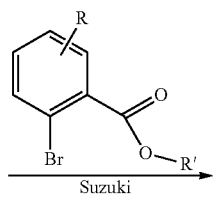
Suzuki →
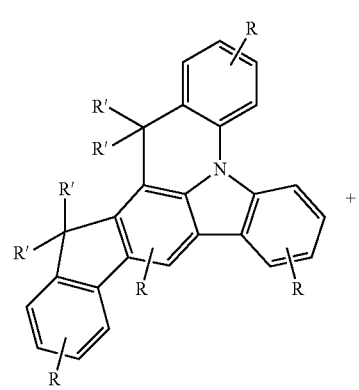
+
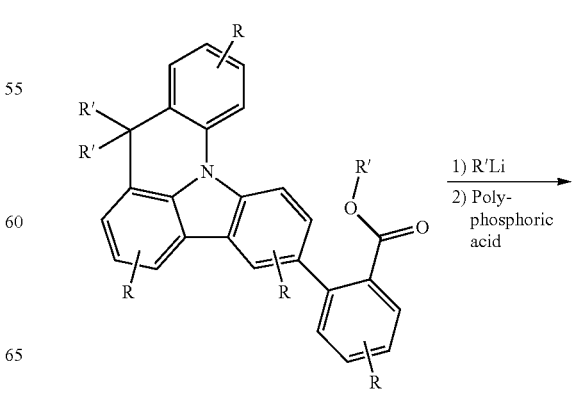
1) R'Li
2) Polyphosphoric acid
→

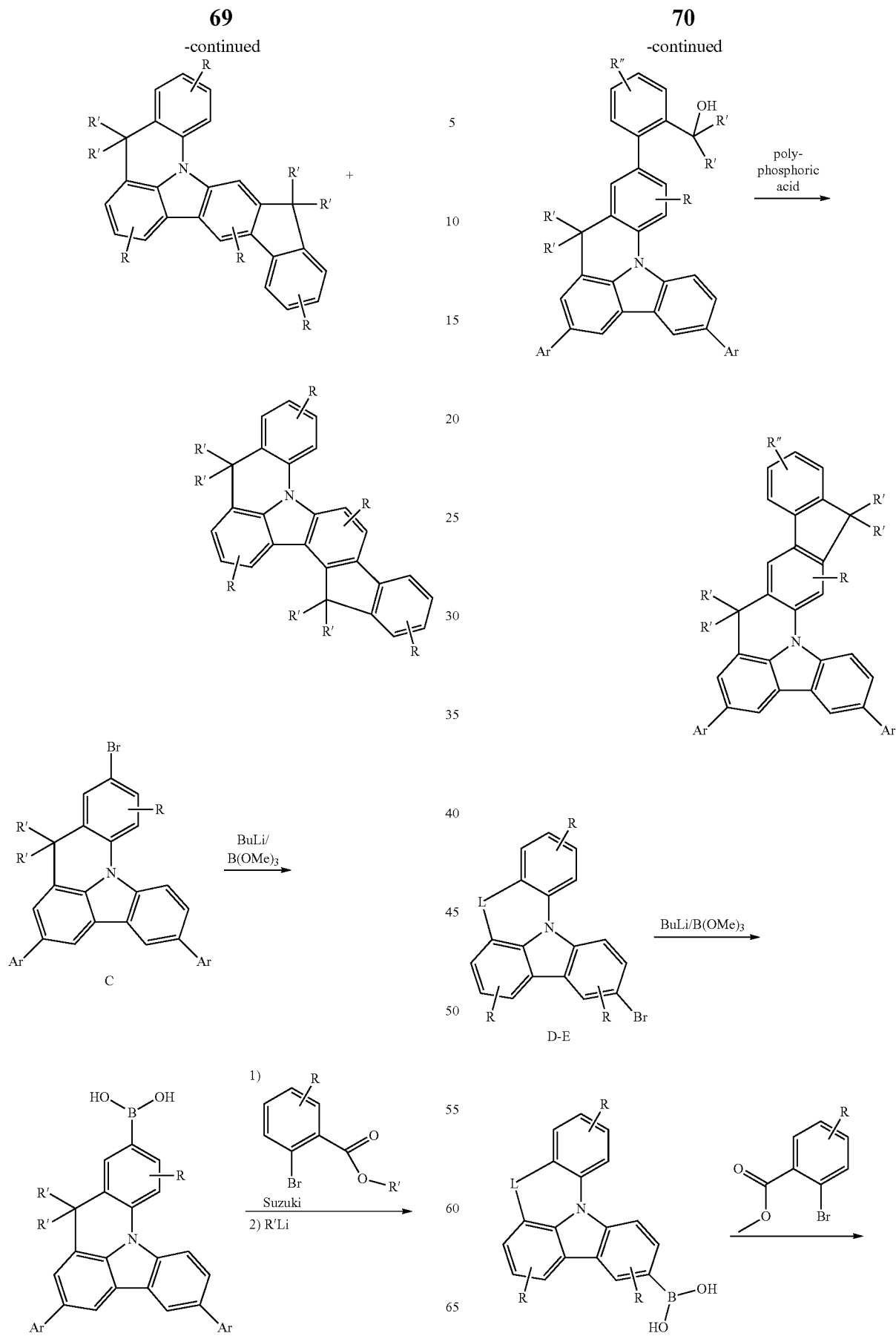

71
-continued
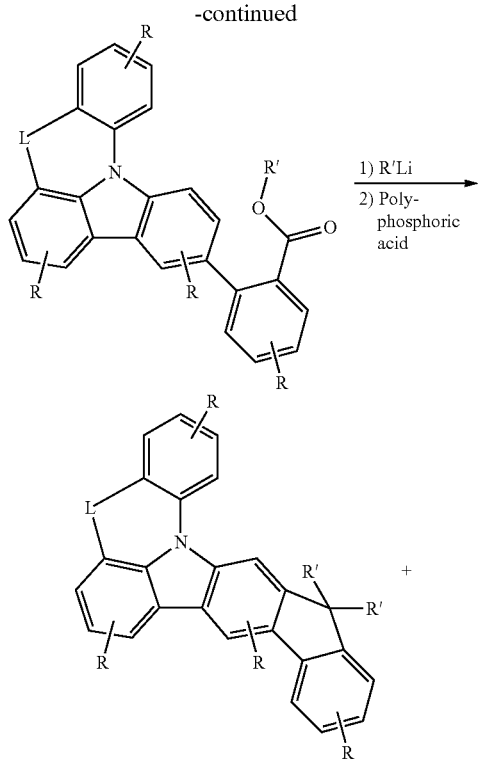
72
-continued
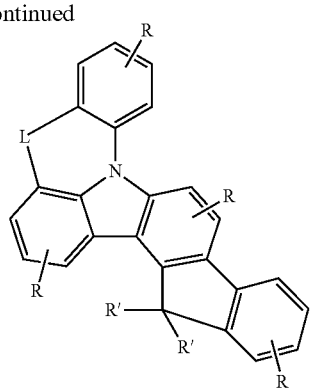
L = O, S, NR
Scheme 3 (a-c) below shows with reference to three illustrative syntheses the variant of a parallel double bridging through the use of bifunctional intermediates. Compounds according to the invention having a symmetrical structure can be prepared in this way.
Scheme 3
a)
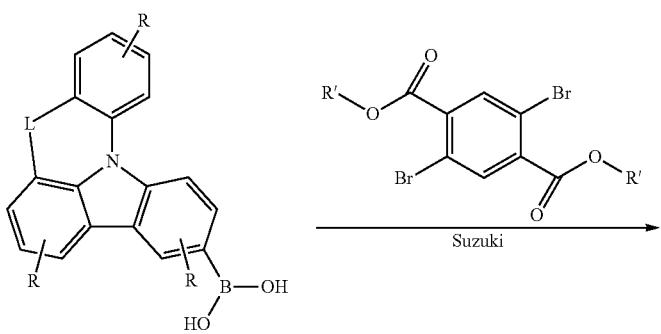
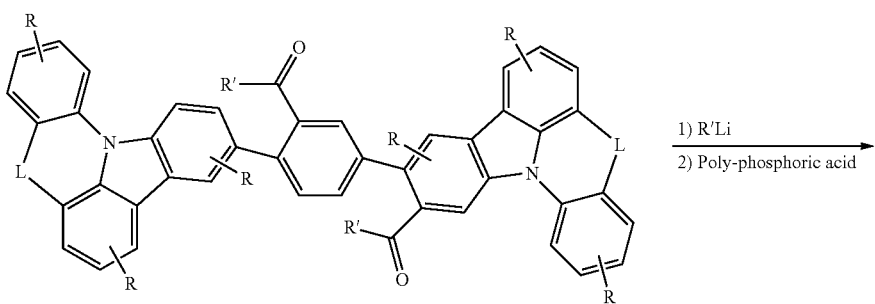

-continued
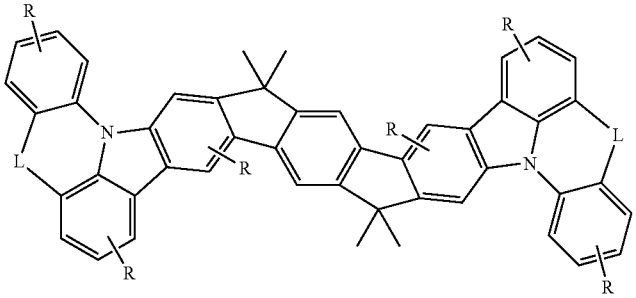
L = CR, NR, S, SO, SO$_2$, O or PR
b)
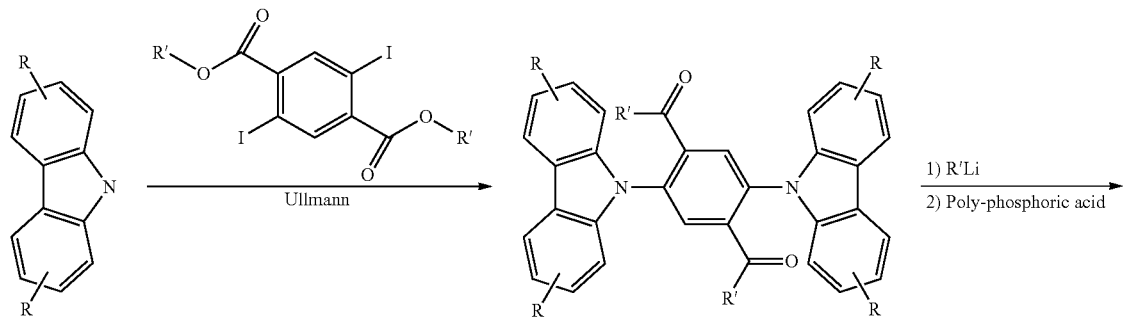
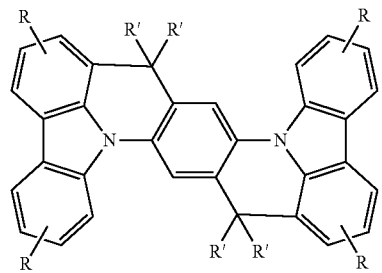
c)
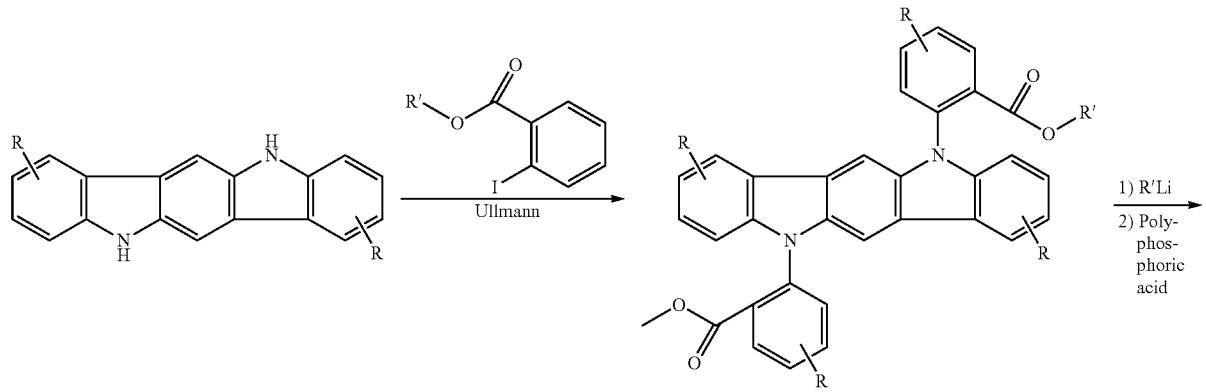

-continued

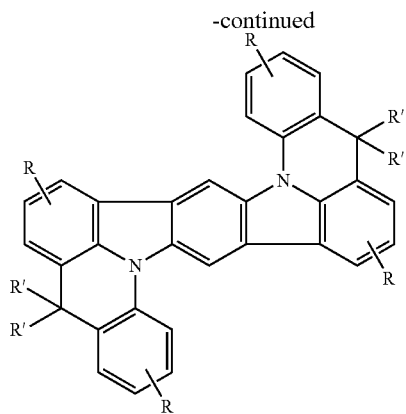 + 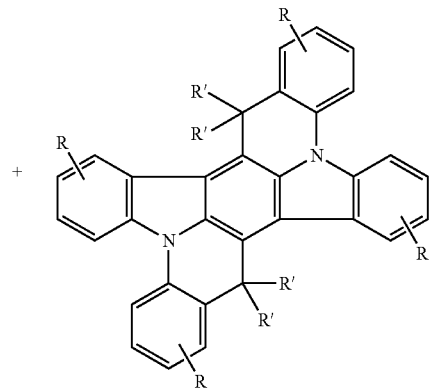

The illustrative synthetic routes shown are intended to indicate possible routes by which the compounds according to the invention can be prepared. The person skilled in the art will be able to modify the synthetic routes using his general expert knowledge if this appears advantageous under the given circumstances.

The invention thus relates to a process for the preparation of compounds of the formula (I), characterised in that it comprises the following steps:
 a) synthesis of a precursor molecule which is unbridged in the relevant position and carries a group Y* and/or T*
 b) performance of the ring-closure reaction, by means of which the bridge Y and/or T is introduced.

The preparation process will generally comprise further synthetic steps, preferably including metal-catalysed coupling reactions for the formation of aryl-aryl bonds, such as, for example, the Suzuki, Buchwald, Stille and Yamamoto coupling.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. The oligomerisation or polymerisation here is preferably carried out via the halogen functionality or the boronic acid functionality.

The invention therefore furthermore relates to oligomers, polymers or dendrimers comprising one or more compounds of the formula (I), where the bond(s) to the polymer, oligomer or dendrimer may be localised at any desired positions substituted by $R^1$ or $R^2$ in formula (I). Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:
(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyper-branched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

The invention also relates to formulations comprising at least one compound of the formula (I) or a polymer, oligomer or dendrimer containing at least one unit of the formula (I) and at least one solvent, preferably an organic solvent.

The compounds of the formula (I) according to the invention or the polymers, oligomers or dendrimers according to the invention are suitable for use in electronic devices, in particular in organic electroluminescent devices (OLEDs). Depending on the substitution, the compounds are employed in various functions and layers, but preferably as matrix material for phosphorescent dopants and/or as hole-transport and/or hole-injection material. The precise use of the compounds depends, in particular, on the choice of the groups $Ar^1$, $Ar^2$, $Ar^3$ and $Ar^4$, but also on the choice of the bridging groups Y and T and of the substituents $R^1$ and $R^2$. For example, compounds which contain electron-deficient groups, such as heteroaryl groups having one, preferably a plurality of nitrogen atoms, are particularly suitable for use as matrix material for phosphorescent dopants.

The invention therefore furthermore relates to the use of the compounds of the formula (I) according to the invention in electronic devices, in particular in organic electroluminescent devices.

In a preferred embodiment of the invention, the compounds of the formula (I) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. If the compounds of the formula (I) are used as hole-transport material, it may be preferred for them to be doped with electron-acceptor compounds, for example by $F_4$-TCNQ or with compounds as described in EP 1476881 or EP 1596445.

In a further preferred embodiment of the invention, a compound of the formula (I) is used as hole-transport material in combination with a hexaazatriphenylene derivative, as described in US 2007/0092755. The hexaazatriphenylene derivative is particularly preferably employed here in its own layer.

Thus, for example, preference is given to the following structure: anode-hexaazatriphenylene derivative-hole-transport layer, where the hole-transport layer comprises one or more compounds of the formula (I). It is likewise possible to use a plurality of successive hole-transport layers in this structure, where at least one hole-transport layer comprises at least one compound of the formula (I). The following structure is likewise preferred: anode-hole-transport layer-hexaazatriphenylene derivative-hole-transport layer, where at least one of the two hole-transport layers comprises one or more compounds of the formula (I). It is likewise possible in this structure for a plurality of successive hole-transport layers to be used instead of one hole-transport layer, where at least one hole-transport layer comprises at least one compound of the formula (I).

If the compound of the formula (I) is employed as hole-transport material in a hole-transport layer, the compound can be employed as the pure material, i.e. in a proportion of 100% in the hole-transport layer, or it can be employed in combination with further compounds in the hole-transport layer.

It is preferred in accordance with the invention for the compound of the formula (I) to be employed in an electronic device comprising one or more phosphorescent emitters. The compound can be used here, for example, in a hole-transport layer, a hole-injection layer or in an emitting layer.

In a further preferred embodiment of the invention, the compounds of the formula (I) are employed as matrix materials for phosphorescent dopants.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the greater.

An emitting layer of an organic electroluminescent device may also comprise a plurality of matrix materials (mixed-matrix systems) and/or a plurality of dopants. In this case too, the dopants are generally the materials whose proportion in the system is the smaller, and the matrix materials are the materials whose proportion in the system is the greater. In individual cases, however, the proportion of an individual matrix material in the system may be smaller than the proportion of an individual dopant.

The proportion of the matrix material of the formula (I) in the emitting layer is in this case between 50.0 and 99.9% by vol., preferably between 80.0 and 99.5% by vol., particularly preferably between 90.0 and 99.0% by vol. Correspondingly, the proportion of the dopant is between 0.01 and 50.0% by vol., preferably between 0.5 and 20.0% by vol. and particularly preferably between 1.0 and 10.0% by vol.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable. The person skilled in the art will also be able to employ further phosphorescent complexes in combination with the compounds of the formula (I) according to the invention in the emitting layer without inventive step.

In a further embodiment of the invention, the compounds according to the invention are employed as co-matrix materials together with a further matrix material (mixed-matrix system). In this case, their proportion is preferably 5 to 95% by vol. A mixed-matrix system in the sense of the invention is a layer which comprises at least three compounds, at least one dopant and at least two matrix materials. The dopant here has a proportion of 0.1-30% by vol., preferably 1-20% by vol., very particularly preferably 1-10% by vol., and the two matrix materials together make up the remainder; the ratio of matrix material to co-matrix material can be adjusted in a broad range, but preferably in the range from 1:10 to 10:1, particularly preferably in the range from 1:4 to 4:1.

Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or DE 102008033943, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with DE 102008036982, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or indenocarbazole derivatives, for example in accordance with WO 2010/136109.

In a further embodiment of the invention, the compounds of the formula (I) are employed as emitting materials in an emitting layer. The compounds are particularly suitable as emitting compounds if they contain at least one diarylamino unit. In this case, the compounds according to the invention are particularly preferably used as green or blue emitters.

The proportion of the compound of the formula (I) as dopant in the mixture of the emitting layer is in this case between 0.1 and 50.0% by vol., preferably between 0.5 and 20.0% by vol., particularly preferably between 1.0 and 10.0% by vol. Correspondingly, the proportion of the matrix material is between 50.0 and 99.9% by vol., preferably between 80.0 and 99.5% by vol., particularly preferably between 90.0 and 99.0% by vol.

Preferred matrix materials for use in combination with the compounds according to the invention as emitters are indicated in one of the following sections.

The invention still furthermore relates to electronic devices, in particular organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), which comprise at least one compound of the formula (I) or an oligomer, dendrimer or polymer according to the invention. It is particularly preferred for the electronic device to be an organic electroluminescent device (OLED).

The organic electroluminescent devices preferably comprise an anode, a cathode and at least one emitting layer, characterised in that at least one organic layer, which may be an emitting layer or another layer, comprises at least one compound of the formula (I) or at least one oligomer, dendrimer or polymer according to the invention.

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, chargegeneration layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers, where at least one organic layer comprises at least one compound of the formula (I) or a polymer, oligomer or dendrimer as defined above. These emission layers particularly preferably have in total a plurality of emission maxima between 380 nm and 750 nm, resulting overall in white emission, i.e. various emitting compounds which are able to fluoresce or phosphoresce and which emit blue, yellow, orange or red light are used in the emitting layers. Particular preference is given to three-layer systems, i.e. systems having three emitting layers, where at least one of these layers preferably comprises at least one compound of the formula (I) or a polymer, oligomer or dendrimer as defined above and where the three layers exhibit blue, green, orange or red emission (for the basic structure see, for example, WO 2005/011013). Emitters which have broad-band emission bands and thus exhibit white emission are likewise suitable for white emission. Alternatively and/or additionally, the compound according to the invention may also be present in a hole-transport layer or another layer.

Besides the compounds according to the invention, preferred dopants in fluorescent organic electroluminescent devices are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of dopants from the class of the styrylamines are substituted or unsubstituted tristilbenamines or the dopants described in WO 2006/000388, WO 2006/058737, WO 2006/000389, WO 2007/065549 and WO 2007/115610. Preference is furthermore given to the condensed hydrocarbons disclosed in the application DE 102008035413.

Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). The compounds according to the invention are furthermore preferred matrix materials, in particular as matrix materials for phosphorescent dopants.

Further preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Apart from the compounds according to the invention, very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable electron-transport and electron-injection materials in the devices according to the invention are, for example, $AlQ_3$, BAlQ, LiQ and LiF, as well as derivatives of electron-deficient heteroaromatic compounds, such as, for example, triazine, pyridazine, pyrimidine, pyrazine and benzimidazole.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Alternatively, it is also possible to use the corresponding quinolinates, for example LiQ. The layer thickness of this interlayer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent in order to facilitate either irradiation of the organic material (O-SCs) or the coupling-out of light (OLEDs, O-lasers). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

Preference is furthermore given to an organic electroluminescent device, characterised in that one or more layers are applied by means of a sublimation process, in which the materials are applied by vapour deposition in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds of the formula (I) or a soluble polymer, oligomer or dendrimer as defined above are necessary for this purpose. High solubility can be achieved through suitable substitution of the compounds.

In accordance with the invention, the electronic devices comprising one or more compounds of the formula (I) can be employed in displays, as light sources in lighting applications and as light sources in medical and/or cosmetic applications (for example in light therapy).

The compounds according to the invention have one or more of the following advantages over the prior art on use in organic electroluminescent devices:

1. The compounds according to the invention are suitable as hole-transport and hole-injection materials, where good charge-carrier mobility is present and a long lifetime of the devices is achieved.
2. The compounds according to the invention are suitable for use as emitter materials, preferably as blue-fluorescent emitter materials, and in this use preferably result in good efficiencies and long lifetimes of the electronic devices.
3. The compounds according to the invention are very highly suitable for use as matrix material in an emitting layer, in particular as matrix material for phosphorescent emitters, and in this use preferably result in good efficiencies, long lifetimes and low operating voltages.
4. The compounds according to the invention have good temperature stability and can therefore be purified efficiently by means of sublimation.

The present application text and also the following examples are directed to the use of the compounds according to the invention in OLEDs and to the use of corresponding devices in displays and as light sources.

It is possible for the person skilled in the art without further inventive step also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers), to mention but a few applications.

The present invention likewise relates to the use of the compounds according to the invention in the corresponding devices and to these devices themselves.

The invention is explained in greater detail by the following examples without wishing it to be restricted thereby.

WORKING EXAMPLES

I) Synthesis of the Bromine-Substituted Bridged Triarylamine Starting Compounds Br-1 to Br-7

3-Bromo-8,8-dimethyl-8H-indolo[3,2,1-de]acridine (Br-1)

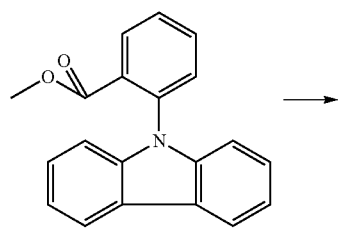

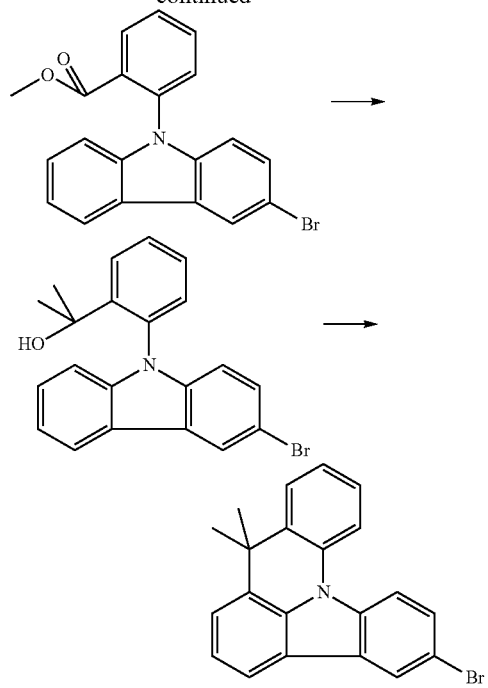

Methyl 2-(3-bromo-9H-carbazolyl)benzoate 62 g (207 mmol) of methyl 2-(9H-carbazolyl)benzoate are cooled to −10° C. in 2 l of DMF, and 37.3 g (207 mmol) of NBS are added in portions. The solution is then brought to room temperature and stirred at this temperature for 6 h. 500 ml of water are subsequently added to the mixture, which is then extracted with $CH_2Cl_2$. The organic phase is dried over $MgSO_4$, and the solvents are removed in vacuo. The product is washed by stirring with hot toluene, and the solid is isolated.

Yield: 72 g (190 mmol), 92% of theory, purity according to $^1$H-NMR about 98%.

2-[2-(3-Bromocarbazol-9-yl)phenyl]propan-2-ol 81 g (213 mmol) of methyl 2-(3-bromo-9H-carbazolyl)benzoate are dissolved in 1.5 l of dried THF and degassed. The solution is cooled to −78° C., and 569 ml (854 mmol) of methyllithium are added over the course of 40 min. The mixture is allowed to warm to −40° C. over the course of 1 h, and the reaction is monitored by TLC. When the reaction is complete, the mixture is carefully quenched with MeOH at −30° C. The reaction solution is concentrated to 1/3, 1 l of methylene chloride is added, the mixture is washed, and the organic phase is dried over $MgSO_4$ and evaporated.

Yield: 73 g (193 mmol), 91% of theory, purity according to $^1$H-NMR about 94%.

6-Bromo-8,8-dimethyl-8H-indolo[3,2,1-de]acridine (Br-1)

16.3 g (43.6 mmol) of 2-[2-(3-bromocarbazol-9-yl)phenyl]propan-2-ol are dissolved in 1.2 l of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in methylene chloride/THF

6-Bromo-8,8-dimethyl-3-phenyl-8H-indolo[3,2,1-de]acridine (Br-2)

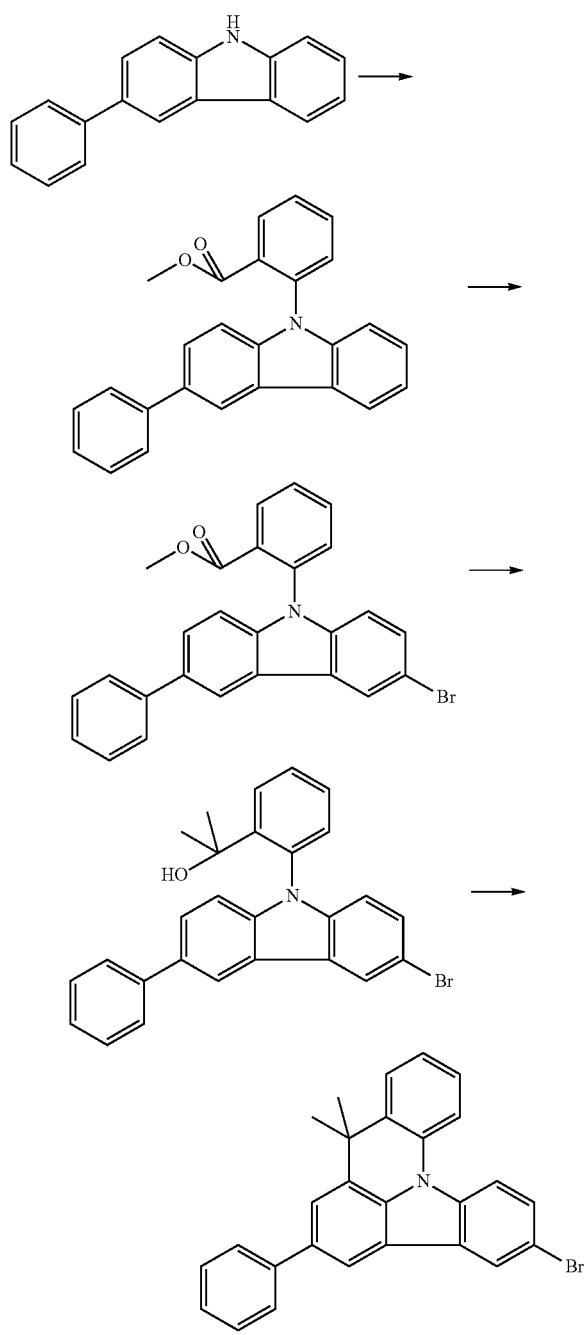

Methyl 2-(3-phenyl-9H-carbazolyl)benzoate 85 g (350 mmol) of 3-phenyl-9H-carbazole, 63 ml (262 mmol) of methyl 2-iodobenzoate, 20 g (315 mmol) of copper powder, 87 g (631 mmol) of potassium carbonate and 9.3 g (35 mmol) of 18-crown-6 are initially introduced in 1200 ml of DMF under a protective gas and heated at 1300° C. for 86 h. The mixture is subsequently evaporated and washed by stirring with hot heptane and purified by chromatography (heptane, dichloromethane 1:1). The product is washed by stirring with hot hexane, and the solid is isolated.

Yield: 82 g (219 mmol), 62% of theory, purity according to $^1$H-NMR about 97%.

Methyl 2-(3-bromo-6-phenyl-9H-carbazolyl)benzoate 78.4 g (207 mmol) of methyl 2-(3-phenyl-9H-carbazolyl)benzoate is cooled to −10° C. in 2 l of DMF, and 37.3 g (207 mmol) of NBS are added in portions. The mixture is subsequently allowed to come to room temperature and is stirred at this temperature for 6 h. 500 ml of water are then added to the mixture, which is then extracted with $CH_2Cl_2$. The organic phase is dried over $MgSO_4$, and the solvents are removed in vacuo. The product is washed by stirring with hot toluene, and the solid is isolated.

Yield: 91.4 g (200 mmol), 95% of theory, purity according to $^1$H-NMR about 98%.

2-[2-(3-Bromo-6-phenylcarbazol-9-yl)phenyl]propan-2-ol 97 g (213 mmol) of methyl 2-(3-bromo-6-phenyl-9H-carbazolyl)benzoate are dissolved in 1500 ml of dried THF and degassed. The solution is cooled to −78° C., and 569 ml (854 mmol) of methyllithium are added over the course of 40 min. The mixture is allowed to warm to −40° C. over the course of 1 h, and the reaction is monitored by TLC. When the reaction is complete, the mixture is carefully quenched with MeOH at −30° C. The reaction solution is concentrated to 1/3, 1 l of methylene chloride is added, the mixture is washed, and the organic phase is dried over $MgSO_4$ and evaporated. Yield: 93.4 g (204 mmol), 95.9% of theory, purity according to $^1$H-NMR about 96%.

6-Bromo-8,8-dimethyl-3-phenyl-8H-indolo[3,2,1-de]acridine (Br-2)

20 g (43.6 mmol) of 2-[2-(3-bromo-6-phenylcarbazol-9-yl)phenyl]propan-2-ol are dissolved in 1.2 l of degassed toluene, a suspension of 40 g of polyphosphoric acid and 28 ml of methanesulfonic acid is added, and the mixture is heated at 60° C. for 1 h. The batch is cooled, and water is added. A solid precipitates out and is then dissolved in methylene chloride/THF (1:1). The solution is carefully rendered alkaline using 20% NaOH, the phases are separated and dried over $MgSO_4$. The solid obtained is washed by stirring with heptane. Yield: 16.3 g (37 mmol), 84.4% of theory, purity according to $^1$H-NMR about 95%.

3-Bromo-8,8-dimethyl-8H-indolo[3,2,1-de]acridine (Br-3)

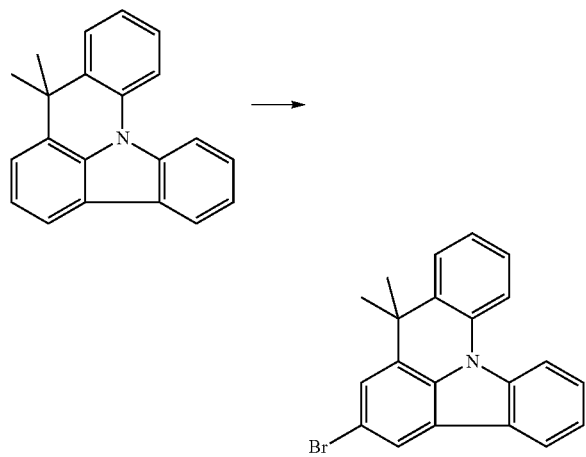

6.3 g (22.2 mmol) of 8,8-dimethylindolo[3,2,1-de]acridine are initially introduced in 150 ml of $CH_2Cl_2$. A solution of 3.9 g (22.3 mmol) of NBS in 100 ml of acetonitrile is subsequently added dropwise at −15° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane, and the solid is isolated.

Yield: 4.5 g (12 mmol), 57% of theory, purity according to $^1$H-NMR about 97%.

10-Bromo-8,8-dimethyl-3,6-diphenyl-8H-indolo[3,2,1-de]acridine (Br-4)

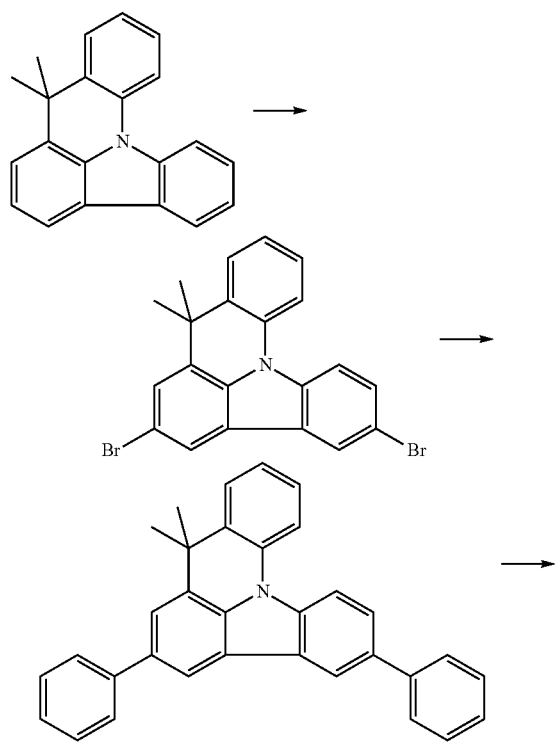

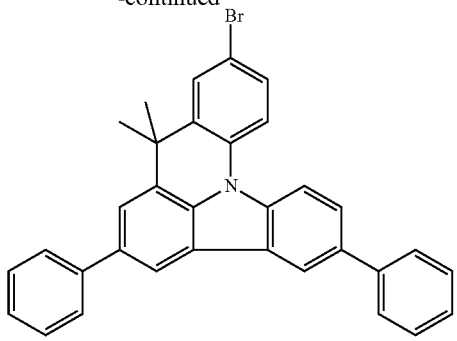

3,6-Dibromo-8,8-dimethyl-8H-indolo[3,2,1-de]acridine 6.3 g (22.2 mmol) of 8,8-dimethylindolo[3,2,1-de]acridine are initially introduced in 150 ml of $CH_2Cl_2$. A solution of 8 g (45.1 mmol) of NBS in 100 ml of acetonitrile is subsequently added dropwise at −15° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane, and the solid is isolated.

Yield: 7.3 g (16 mmol), 75% of theory, purity according to $^1$H-NMR about 97%.

8,8-Dimethyl-3,6-diphenyl-8H-indolo[3,2,1-de]acridine 19.8 g (45 mmol) of 3,6-dibromo-8,8-dimethyl-8H-indolo[3,2,1-de]acridine, 11.4 g (94 mmol) of phenylboronic acid and 164 ml of saturated $NaHCO_3$ solution are suspended in 1500 ml of toluene and 150 ml of ethanol. 1.9 g (1.6 mmol) of $Pd(PPh)_3$ are added to this suspension, and the reaction mixture is heated under reflux for 16 h. After cooling, the organic phase is separated off, filtered through silica gel, washed three times with 200 ml of water and subsequently evaporated to dryness.

Yield: 18.5 g (42 mmol), 95% of theory, purity according to $^1$H-NMR about 98%.

10-Bromo-8,8-dimethyl-3,6-diphenyl-8H-indolo[3,2,1-de]acridine (Br-4)

9.6 g (22.2 mmol) of 8,8-dimethyl-3,6-diphenyl-8H-indolo[3,2,1-de]acridine are initially introduced in 150 ml of $CH_2Cl_2$. A solution of 3.9 g (22.3 mmol) of NBS in 100 ml of acetonitrile is subsequently added dropwise at −15° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane, and the solid is isolated.

Yield: 10.7 g (20.8 mmol), 94% of theory, purity according to $^1$H-NMR about 97%.

2,5-Dibromo-7,7,11,11-tetramethyl-7H,11H-benz[1,8]indolo[2,3,4,5,6-de]acridine (Br-5)

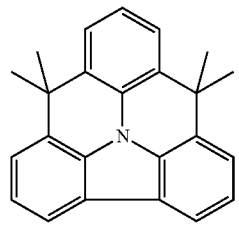

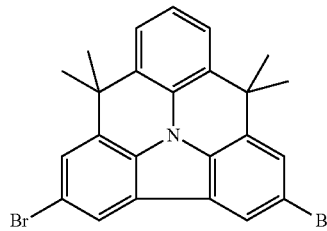

7.18 g (22.2 mmol) of 7,7,11,11-tetramethyl-7H,11H-benz[1,8]indolo-[2,3,4,5,6-de]acridine are initially introduced in 150 ml of CH$_2$Cl$_2$. A solution of 8 g (45.1 mmol) of NBS in 100 ml of CH$_2$Cl$_2$ is subsequently added dropwise at 0° C. with exclusion of light, and the mixture is allowed to come to room temperature and is stirred at this temperature for a further 4 h. 150 ml of water are subsequently added to the mixture, which is then extracted with CH$_2$Cl$_2$. The organic phase is dried over MgSO$_4$, and the solvents are removed in vacuo. The product is washed by stirring with hot hexane, and the solid is isolated.

Yield: 8.1 g (16 mmol), 70% of theory, purity according to $^1$H-NMR about 98%.

3-Bromo-8H-8,12b-diazabenzo[a]aceanthrylene (Br-6)

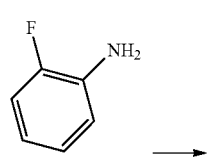

+

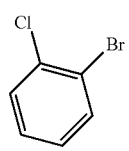

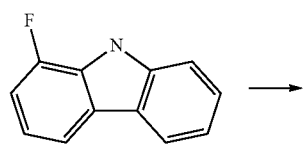

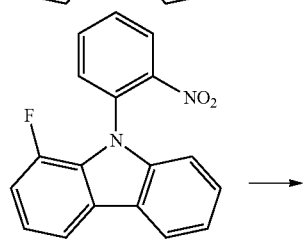

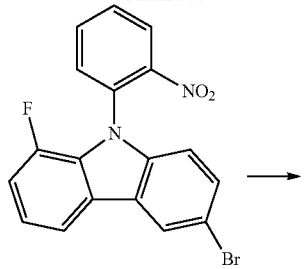

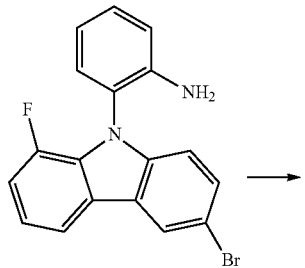

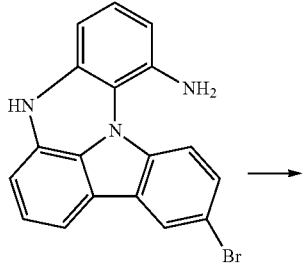

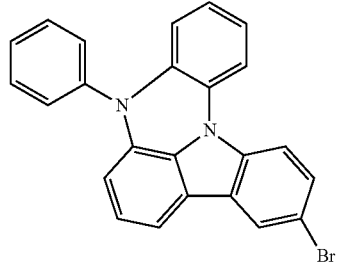 [SMILES: Brc1ccc2c(c1)c1cccc3c1n2-c1ccccc1N3c1ccccc1]

Fluoro-9-(2-nitrophenyl)-9H-carbazole

A degassed solution of 97 ml (990 mmol) of 2-fluoroaniline and 165 g (862 mmol) of 2-bromochlorobenzene in 1000 ml of NMP is saturated with N$_2$ for 1 h. Then, firstly 28.9 g (100 mmol) of trichlorohexylphosphine, then 11.2 g (50 mmol) of palladium acetate are added to the solution, and 549 g (2.5 mol) of potassium carbonate in the solid state are subsequently added. The reaction mixture is heated under reflux for 18 h. After cooling to room temperature, 1 l of water are carefully added. The organic phase is washed with 4×50 ml of H$_2$O and dried over MgSO$_4$, and the solvents are removed in vacuo. The pure product is obtained by recrystallisation. The yield is 111 g (760 mmol), corresponding to 70% of theory.

6-Bromo-1-fluoro-9-(2-nitrophenyl)-9H-carbazole 6.7 g (22.2 mmol) of fluoro-9-(2-nitrophenyl]-9H-carbazole are initially introduced in 150 ml of CH$_2$Cl$_2$. A solution of 3.9 g (22.3 mmol) of NBS in 100 ml of acetonitrile is subsequently added dropwise at −15° C. with exclusion of light, and the mixture is allowed to come to room temperature and is stirred at this temperature for a further 4 h. 150 ml of water are subsequently added to the mixture, which is then extracted with CH$_2$Cl$_2$. The organic phase is dried over MgSO$_4$, and the solvents are removed in vacuo. The product is washed by stirring with hot hexane, and the solid is isolated.

Yield: 8 g (20 mmol), 97% of theory, purity according to $^1$H-NMR about 97%.

2-(6-Bromo-1-fluorocarbazol-9-yl)phenylamine 67 g (219 mmol) of 6-bromo-1-fluoro-9-(2-nitrophenyl)-9H-carbazole are dissolved in 820 ml of EtOH, 143 g (755 mmol) of ZnCl$_2$ are added at room temperature, and the mixture is heated under reflux for 6 h. The mixture is allowed to come to room temperature over the course of 1 h, 20% NaOH is added, and the phases are separated. The solvent is then removed, and the residue is purified by chromatography. The yield is 44 g (125 mmol), corresponding to 72% of theory.

3-Bromo-8H-8,12b-diazabenzo[a]aceanthrylene

Under a protective gas, 25 g (72 mmol) of 2-(6-bromo-1-fluorocarbazol-9-yl)phenylamine are dissolved in 200 ml of DMF, 2.8 g (72 mmol) of NaH (60% in oil) are added at room temperature, and the mixture is heated under reflux for 6 h. The mixture is allowed to come to room temperature over the course of 1 h, the solvent is then removed, and the residue is purified by chromatography. The yield is 19 g (54 mmol), corresponding to 78% of theory.

Bromo-8-phenyl-8H-8,12b-diazabenzo[a]aceanthrylene (Br-6)

A degassed solution of 30 g (86.6 mmol) of 3-bromo-8H-8,12b-diazabenzo-[a]aceanthrylene and 8.8 g (95.9 mmol) of phenylamine in 1 l of dioxane is saturated with N$_2$ for 1 h. Then, firstly 0.9 ml (4.3 mmol) of P($^t$Bu)$_3$, then 0.480 g (2.1 mmol) of palladium acetate are added to the solution. 12.6 g (131 mmol) of NaOtBu in the solid state are subsequently added. The reaction mixture is heated under reflux for 18 h. After cooling to room temperature, 1 l of water is carefully added. The organic phase is washed with 4×50 ml of H$_2$O and dried over MgSO$_4$, and the solvents are removed in vacuo. The pure product is obtained by recrystallisation. The yield is 27 g (64 mmol), corresponding to 76% of theory.

10-Bromo-8,8-dimethyl-8H-indolo[3,2,1-de]acridine (Br-7)

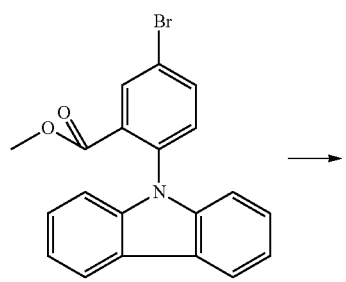

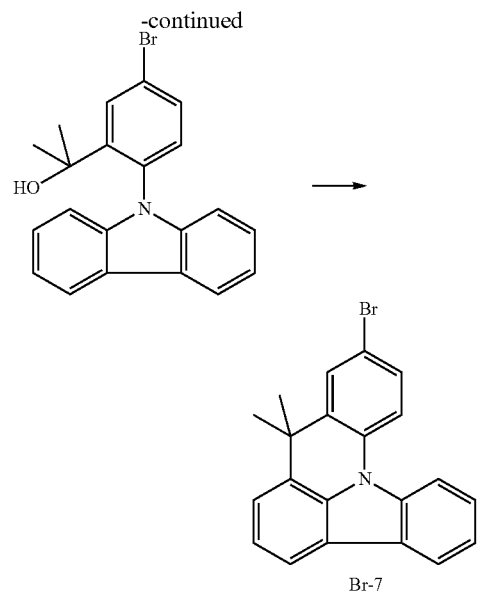

Br-7 a) 2-(5-Bromo-2-carbazol-9-ylphenyl)propan-2-ol 80.9 g (213 mmol) of methyl 5-bromo-2-carbazol-9-ylbenzoate (synthesis: J. Mat. Chem. 2009, 19(41), 7661-7665) are dissolved in 1500 ml of dried THF and degassed. The solution is cooled to −78° C., and 569 ml (854 mmol) of methyllithium are added over the course of 40 min. The mixture is allowed to warm to −40° C. over the course of 1 h, and the reaction is monitored by TLC. When the reaction is complete, the mixture is carefully quenched with MeOH at −30° C. The reaction solution is concentrated to one third, and 1 l of methylene chloride is added. The solution is subsequently washed, and the organic phase is dried over MgSO$_4$ and evaporated. Yield: 78.1 g (206 mmol), 97% of theory, purity according to $^1$H-NMR about 94%.

b) 10-Bromo-8,8-dimethyl-8H-indolo[3,2,1-de]acridine 16.4 g (43.6 mmol) of 2-(5-bromo-2-carbazol-9-ylphenyl)propan-2-ol are dissolved in 1200 ml of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in methylene chloride/THF (1:1). The solution is carefully rendered alkaline using 20% NaOH, the phases are separated and dried over MgSO$_4$. The solid obtained is washed by stirring with heptane. Yield: 14.8 g (40 mmol), 95% of theory, purity according to $^1$H-NMR about 95%.

II) Synthesis of Compounds 1 to 10 According to the Invention

Compounds according to the invention can be synthesised starting from bromine-substituted bridged triarylamine intermediates. Examples of the synthesis of some of these compounds (Br-1 to Br-7) were given in the preceding section.

The syntheses shown below of compounds 1, 2, 3 and 4 according to the invention are based on intermediates Br-1 or Br-4.

Synthetic processes for the preparation of compounds 5a-5k,6, 7 and 10a-10n according to the invention, in which unsubstituted carbazole or N-phenylbicarbazole serves as starting material, are subsequently described.

Compound 8 according to the invention is synthesised starting from the bromine-substituted triarylamine intermediate Br-1.

The synthesis of compound 9 according to the invention is based on intermediate Br-7.

Further compounds according to the invention, for example those based on intermediates Br-2 and Br-3, can be prepared with a corresponding modification of the syntheses.

This can be carried out by the person skilled in the art in accordance with the processes shown below.

Synthesis of Compounds 1 and 2

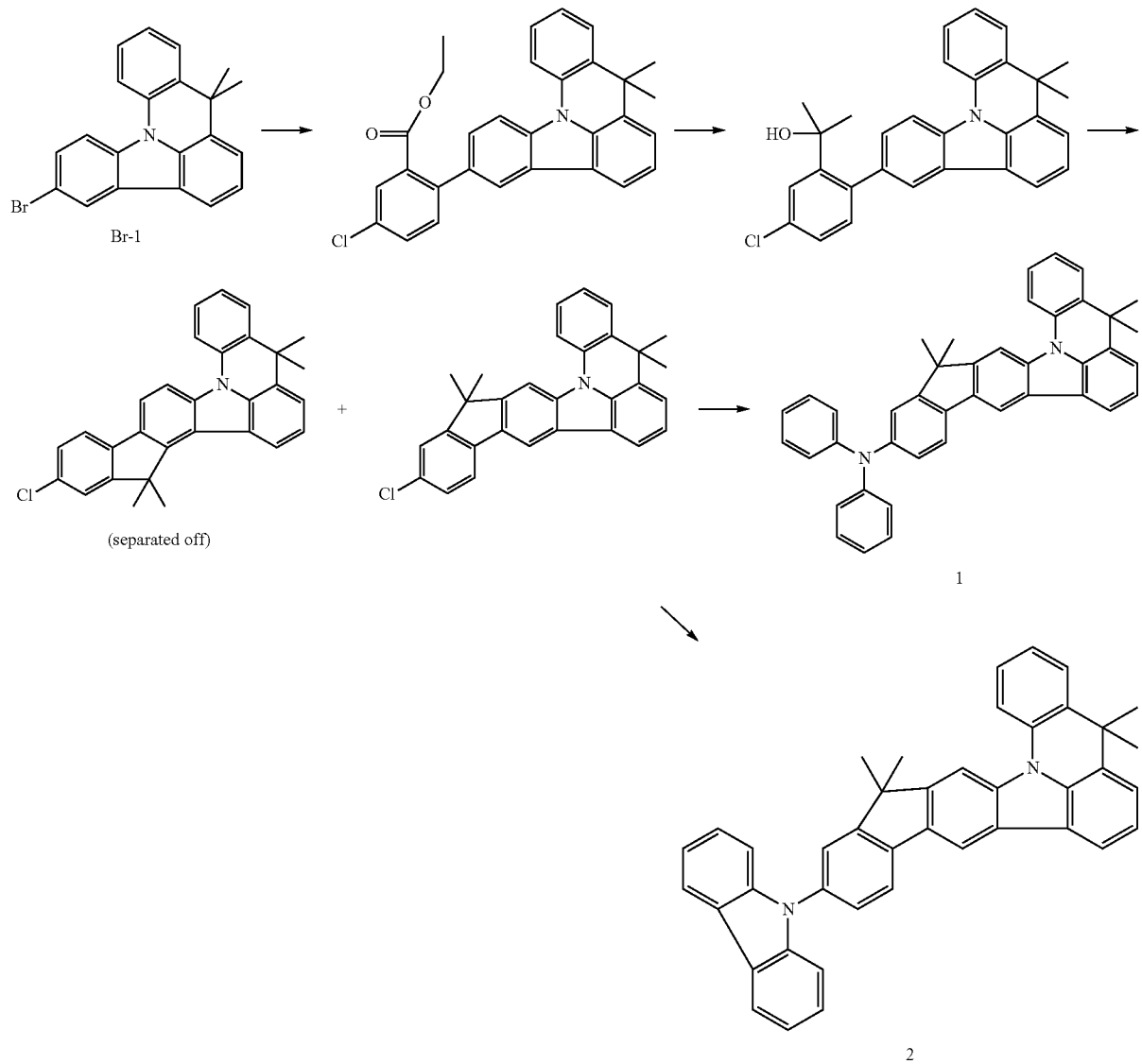

sodium carbonate are suspended in 350 ml of toluene, 350 ml of dioxane and 500 ml of water. 913 mg (3.0 mmol) of tri-otolylphosphine and then 112 mg (0.5 mmol) of palladium (II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene. The yield is 44 g (94 mmol), corresponding to 86% of theory.

2-[2-(8,8-Dimethyl-8H-indolo[3,2,1-de]acridin-3-yl)phenyl]propan-2-ol

Under a protective gas, 105 g (227 mmol) of ethyl 2-(8,8-dimethyl-8H-indolo[3,2,1-de]acridin-3-yl)benzoate are ini- Ethyl 2-(8,8-dimethyl-8H-indolo[3,2,1-de]acridin-3-yl)benzoate 39.8 g (110.0 mmol) of 3-bromo-8,8-dimethyl-8H-indolo[3,2,1-de]acridine (Br-1), 30 g (110.0 mmol) of [4-chloro-2-(ethoxycarbonyl)phenyl]boronic acid and 9.7 g (92 mmol) of tially introduced in 2 l of THF and cooled to 0° C. 150 ml of methylmagnesium chloride solution are added dropwise at this temperature, and the mixture is subsequently brought to room temperature overnight. 300 ml of saturated NH$_4$Cl solution and 900 ml of water/conc. HCl 8:1 are added to the solution. The phases are separated, and the solvent is removed in vacuo. The residue is recrystallised from heptane. The yield is 80 g (176 mmol), corresponding to 79% of theory.

Cyclisation:

Under a protective gas, 90 g (200 mmol) of 2-[2-(8,8-dimethyl-8H-indolo-[3,2,1-de]acridin-3-yl)phenyl]propan-2-ol in 134 g (1.37 mol) of polyphosphoric acid are initially introduced and cooled to 0° C. The mixture is subsequently stirred at 100° C. for 3 h and then cooled to room temperature. Water is added to the mixture with ice cooling, the mixture is then extracted with ethyl acetate, and the solvent is removed in vacuo. The ratio of the isomers is 70:30. They can be separated by recrystallisation from toluene/isopropanol. The yield of the isomer mixture is 69 g (159 mmol), corresponding to 80% of theory.

Compound 1:

A degassed solution of 37 g (86.6 mmol) of the compound from the cyclisation step and 16 g (95.9 mmol) of diphenylamine in 1 l of dioxane is saturated with $N_2$ for 1 h. Then, firstly 0.9 ml (4.3 mmol) of P($^t$Bu)$_3$, then 0.480 g (2.1 mmol) of palladium acetate are added to the solution, and 12.6 g (131 mmol) of NaOtBu in the solid state are subsequently added. The reaction mixture is heated under reflux for 18 h. After cooling to room temperature, 1 l of water are carefully added. The organic phase is washed with 4×50 ml of $H_2O$ and dried over $MgSO_4$, and the solvents are removed in vacuo. The residue is recrystallised from toluene and from chlorobenzene and finally sublimed in a high vacuum. The purity is 99.9%. The yield is 37 g (65 mmol), corresponding to 77% of theory.

Compound 2:

A degassed solution of 37 g (86.6 mmol) of the compound from the cyclisation step and 15.8 g (95.9 mmol) of carbazole in 1000 ml of dioxane is saturated with $N_2$ for 1 h. Then, firstly 0.9 ml (4.3 mmol) of P($^t$Bu)$_3$, then 0.480 g (2.1 mmol) of palladium acetate are added to the solution, and 12.6 g (131 mmol) of NaOtBu as the solid are subsequently added. The reaction mixture is heated under reflux for 18 h. After cooling to room temperature, 1 l of water are carefully added. The organic phase is washed with 4×50 ml of $H_2O$ and dried over $MgSO_4$, and the solvents are removed in vacuo. The residue is recrystallised from toluene and from chlorobenzene and finally sublimed in a high vacuum. The purity is 99.9%. The yield is 28.8 g (51 mmol), corresponding to 60% of theory.

Synthesis of Compound 3

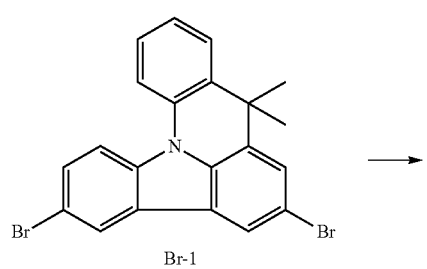

Br-1

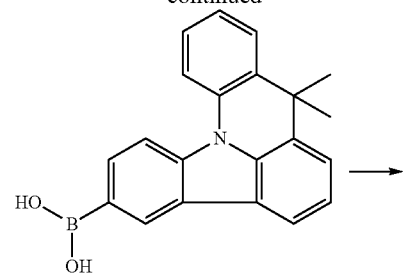

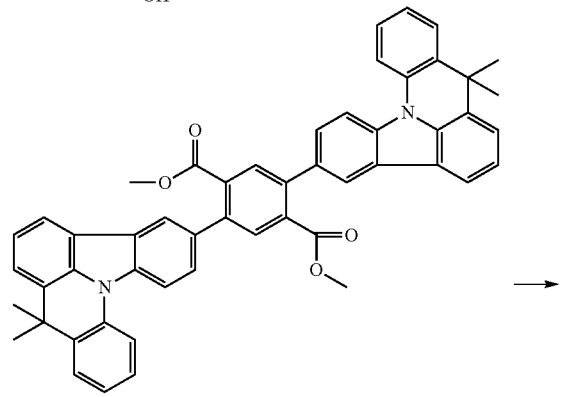

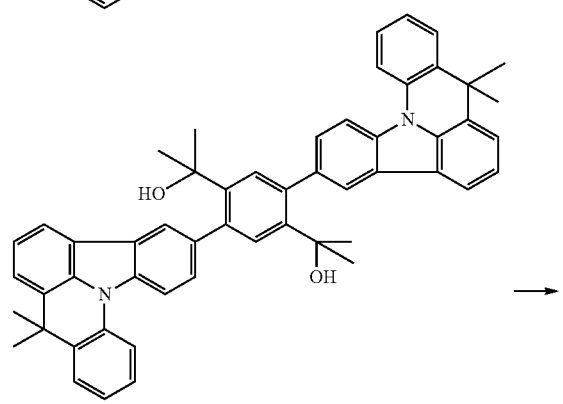

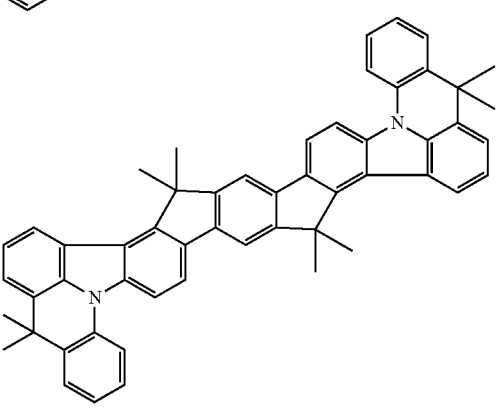

3

8,8-Dimethyl-8H-indolo[3,2,1-de]acridine-6-boronic acid 93.7 g (259 mmol) of 6-bromo-8,8-dimethyl-8H-indolo[3,2,1-de]acridine (Br-1) are dissolved in 1500 ml of dry THF, 135 ml (337 mmol) of a 2.5 M solution of n-butyllithium in cyclohexane are added dropwise at −70° C., and, after 1 h, 37 ml of trimethyl borate (336 mmol) are added dropwise. The mixture is allowed to come to room temperature over the course of 1 h, the solvent is removed, and the residue, which is uniform according to ¹H-NMR, is employed without further purification in the subsequent reaction. The yield is 77 g (235 mmol), corresponding to 91% of theory.

Dimethyl 2-(8,8-dimethyl-8H-indolo[3,2,1-de]acridin-2-yl)-5-(8,8-dimethyl-8H-indolo[3,2,1-de]acridin-3-yl)terephthalate 268 g (820 mol) of 8,8-dimethyl-8H-indolo[3,2,1-de]acridine-6-boronic acid, 180.4 g (474 mmol) of diethyl dibromoterephthalate and 315.9 g (2.29 mol) of potassium carbonate are initially introduced in a mixture of 850 ml of toluene and 850 ml of water and saturated with $N_2$ for 30 min. After addition of 1.36 g (1.18 mmol) of Pd(PPh$_3$)$_4$, the mixture is heated at the boil for 4 h. After cooling to RT and addition of 400 ml of EtOH, the mixture is cooled to room temperature and stirred for 1 h, and the precipitate is filtered off with suction, washed with water, EtOH and heptane and dried at 80° C. in vacuo. The yield is 295 g (390 mmol), corresponding to 71% of theory.

2-[5-(8,8-Dimethyl-8H-indolo[3,2,1-de]acridin-2-yl)-2-(8,8-dimethyl-8H-indolo[3,2,1-de]acridin-3-yl)-4-(1-hydroxy-1-methylethyl)phenyl]propan-2-ol 103 g (136.4 mmol) of dimethyl 2-(8,8-dimethyl-8H-indolo[3,2,1-de]acridin-2-yl)-5-(8,8-dimethyl-8H-indolo[3,2,1-de]acridin-3-yl)terephthalate are initially introduced in 600 ml of THF and cooled to −70° C., and 400 ml (600 mmol) of 1.6 M methyllithium solution are added dropwise at −70° C. over the course of 60 min. After 2 h at −70° C., firstly 30 ml of ice-water, then 60 ml of 50% acetic acid are added dropwise, the reaction mixture is worked up by extraction with ethyl acetate/water, and the organic phase is dried over Na$_2$SO$_4$ and freed from solvent in vacuo. The yield is 90 g (120 mmol), corresponding to 88% of theory.

Compound 3:

31.7 g (42 mmol) of 2-[5-(8,8-dimethyl-8H-indolo[3,2,1-de]acridin-2-yl)-2-(8,8-dimethyl-8H-indolo[3,2,1-de]acridin-3-yl)-4-(1-hydroxy-1-methylethyl)phenyl]propan-2-ol are dissolved in 1200 ml of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in methylene chloride/THF (1:1). The solution is carefully rendered alkaline using 20% NaOH, the phases are separated and dried over MgSO$_4$. The solid obtained is washed by stirring with heptane. Yield: 26.3 g (36.5 mmol), 87% of theory, purity according to HPLC about 99.9%.

Synthesis of Compound 4

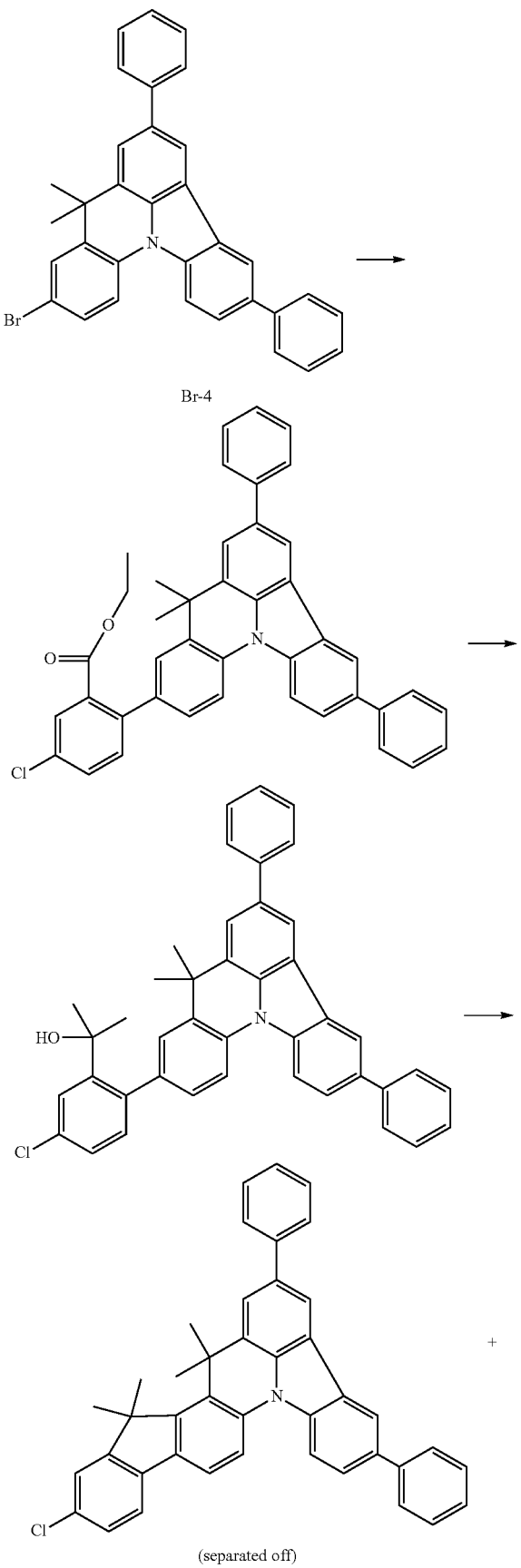

Br-4

(separated off)

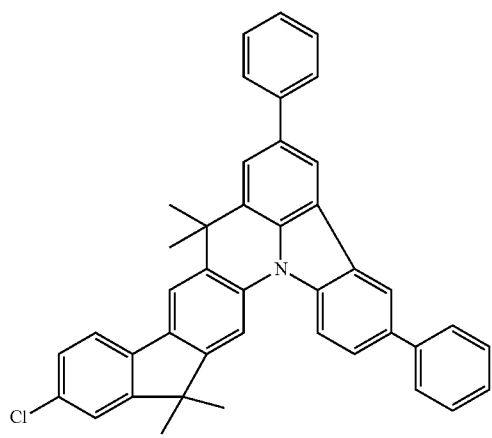

4

The cyclised precursor of compound 4 is prepared in an analogous manner as shown for compounds 1 and 2 from starting compound Br-4 and [4-chloro-2-(ethoxycarbonyl)phenyl]boronic acid by Suzuki coupling, reaction with methylmagnesium chloride solution and acid-catalysed cyclisation. This is followed by separation of the isomers, which are present in a ratio of 70:30 and can be separated by recrystallisation from toluene/acetonitrile.

The precise procedure for the final reaction resulting in compound 4 according to the invention is given below:

Compound 4:

A degassed solution of 37 g (86.6 mmol) of the compound from the preceding step and 15.8 g (95.9 mmol) of carbazole in 1000 ml of dioxane is saturated with $N_2$ for 1 h. Then, firstly 0.9 ml (4.3 mmol) of P($^t$Bu)$_3$ and then 0.48 g (2.1 mmol) of palladium acetate are added to the solution. 12.6 g (131 mmol) of NaOtBu as the solid are subsequently added. The reaction mixture is heated under reflux for 18 h. After cooling to room temperature, 1000 ml of water are carefully added. The organic phase is washed with 4×50 ml of $H_2O$ and dried over MgSO$_4$, and the solvents are removed in vacuo. The residue is recrystallised from toluene and from chlorobenzene and finally sublimed in a high vacuum. The purity is 99.9%. The yield is 23.8 g (43 mmol), corresponding to 51% of theory.

Synthesis of Compounds 5a-5k

Synthesis of Compound 5a

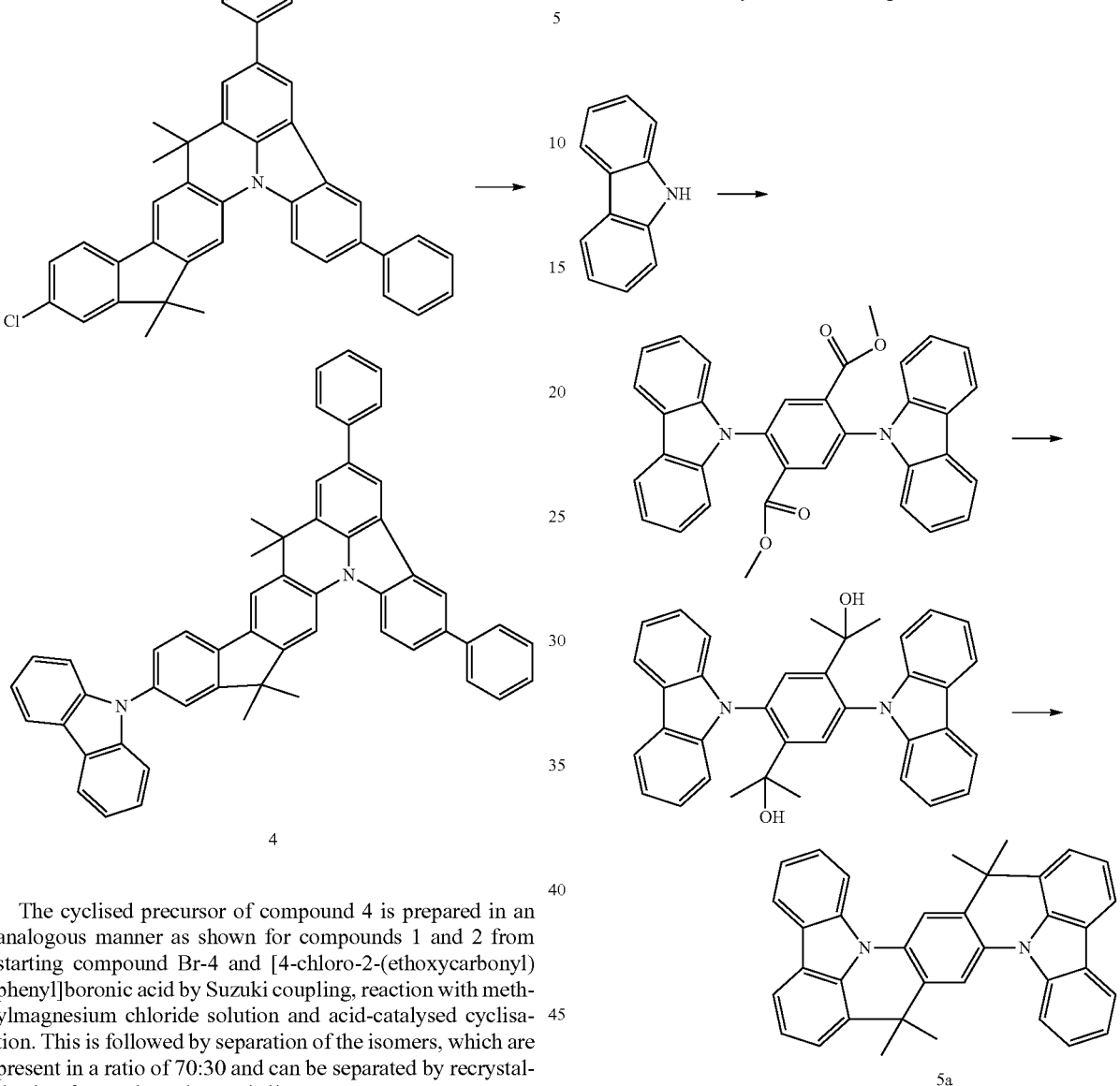

Dimethyl 2,5-biscarbazol-9-ylterephthalate

A degassed solution of 13.6 g (43 mmol) of diethyl dibromoterephthalate and 15.8 g (95.9 mmol) of carbazole in 1 l of dioxane is saturated with $N_2$ for 1 h. Then, firstly 0.9 ml (4.3 mmol) of P($^t$Bu)$_3$, then 0.48 g (2.1 mmol) of palladium acetate are added to the solution, and 12.6 g (131 mmol) of NaOtBu as the solid are subsequently added. The reaction mixture is heated under reflux for 18 h. After cooling to room temperature, 1 l of water is carefully added. The organic phase is washed with 4×50 ml of $H_2O$ and dried over MgSO$_4$, and the solvents are removed in vacuo. The pure product is obtained by recrystallisation. The yield is 18 g (34 mmol), corresponding to 81% of theory.

2-[2,5-Biscarbazol-9-yl-4-(1-hydroxy-1-methyl-ethyl)phenyl]propan-2-ol 73 g (140 mmol) of dimethyl 2,5-biscarbazol-9-yltereph-thalate are initially introduced in 600 ml of THF and cooled to −70° C., and 400 ml (600 mmol) of 1.6 M methyllithium solution are added dropwise at −70° C. over the course of 60 min. After 2 h at −70° C., firstly 30 ml of ice-water, then 60 ml of 50% acetic acid are added dropwise, the reaction mixture is worked up by extraction with ethyl acetate/water, and the organic phase is dried over $Na_2SO_4$ and freed from solvent in vacuo. The yield is 60.9 g (116 mmol), corresponding to 83% of theory.

Cyclisation to Compound 5a:

23 g (45 mmol) of 2-[2,5-biscarbazol-9-yl-4-(1-hydroxy-1-methylethyl)phenyl]propan-2-ol are dissolved in 1.2 l of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in methylene chloride/THF (1:1). The solution is carefully rendered alkaline using 20% NaOH, the phases are separated and dried over $MgSO_4$. The solid obtained is washed by stirring with heptane. Yield: 15.3 g (31 mmol), 70% of theory, purity according to HPLC about 99.9%.

Compounds 5b-5k are obtained analogously:

| Ex. | Starting material 1 | Product | Yield |
|---|---|---|---|
| 5b | 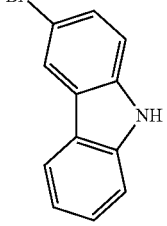<br>1592-95-6 | 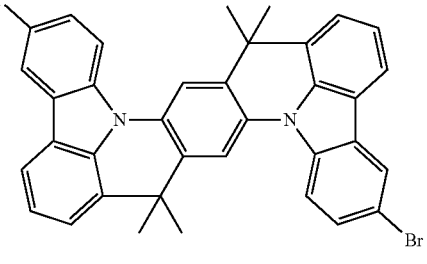 | 67% |
| 5c | 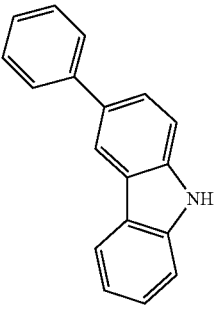<br>103012-26-6 | 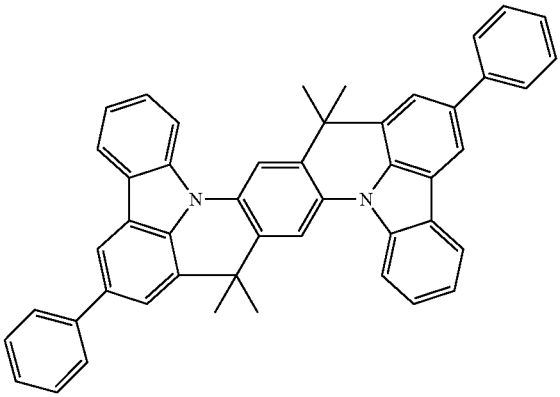 [SMILES: CC1(C)c2cc3c(cc2-n2c4ccccc4c4cc(-c5ccccc5)cc1c42)C(C)(C)c1cc(-c2ccccc2)cc2c4ccccc4n-3c12] | 74% |
| 5d | 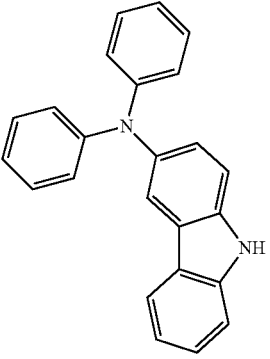<br>883224-26-8 | 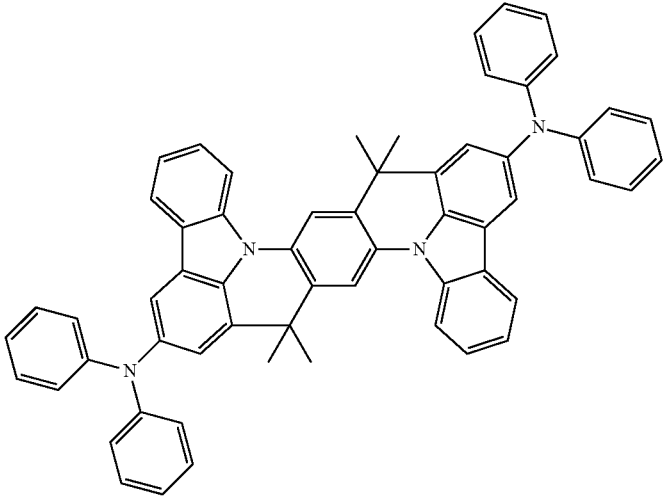 [SMILES: CC1(C)c2cc3c(cc2-n2c4ccccc4c4cc(N(c5ccccc5)c5ccccc5)cc1c42)C(C)(C)c1cc(N(c2ccccc2)c2ccccc2)cc2c4ccccc4n-3c12] | 65% |

-continued

| Ex. | Starting material 1 | Product | Yield |
|---|---|---|---|
| 5e | 56525-79-2 | | 68% |
| 5f | 42448-04-4 | | 62% |
| 5g | 37500-95-1 | | 59% |
| 5h | 244-69-9 | | 66% |

-continued
| Ex. | Starting material 1 | Product | Yield |
|---|---|---|---|
| 5i | 6267-02-3 | | 58% |
| 5j | 92-84-2 | | 68% |
| 5k | 18628-07-4 | | 59% |
Synthesis of Compound 6
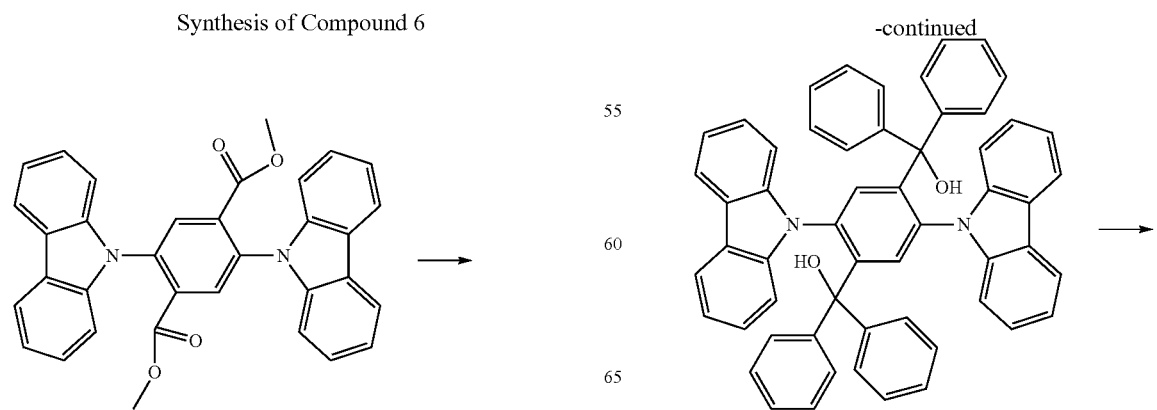

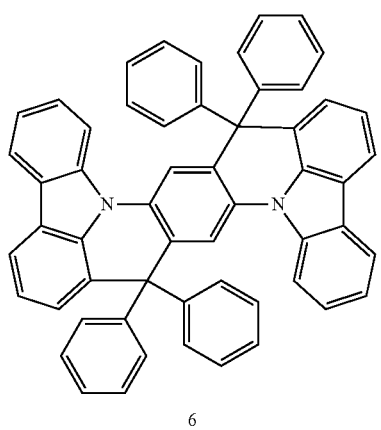

6 a) [2,5-Biscarbazol-9-yl-4-(hydroxydiphenylmethyl)phenyl]diphenyl-methanol

The compound is synthesised by the same procedure as for the corresponding step of Example 5 by reaction of 73 g (140 mmol) of dimethyl 2,5-biscarbazol-9-ylterephthalate with 400 ml (600 mmol) of 1.6 M phenyllithium solution. The yield is 89 g (115 mmol), corresponding to 82% of theory.

b) Cyclisation to Compound 6

The compound is synthesised by the same procedure as for the corresponding step of Example 5 by reaction of 34.7 g (45 mmol) of [2,5-bis-carbazol-9-yl-4-(hydroxydiphenylmethyl)phenyl]diphenylmethanol with 40 g of polyphosphoric acid and 28 ml of methanesulfonic acid. The solid obtained is washed by stirring with heptane. Yield: 26 g (35.5 mmol), 79% of theory, purity according to HPLC about 99.9%.

Synthesis of Compound 7

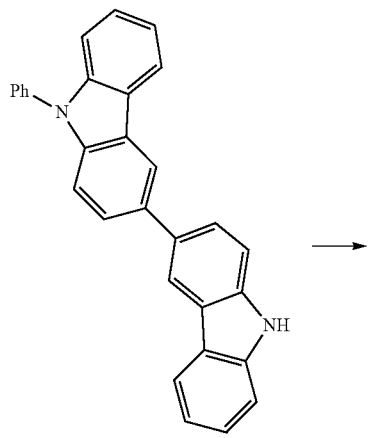

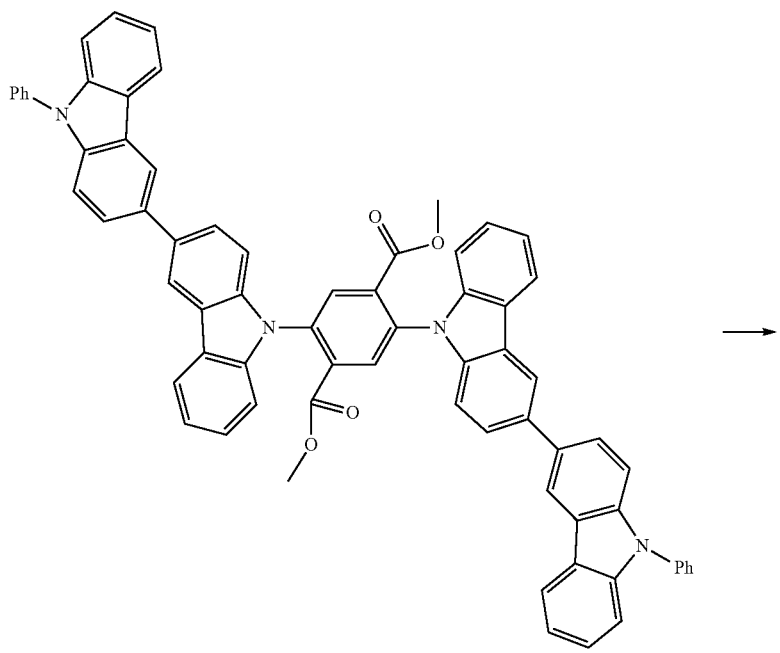

-continued

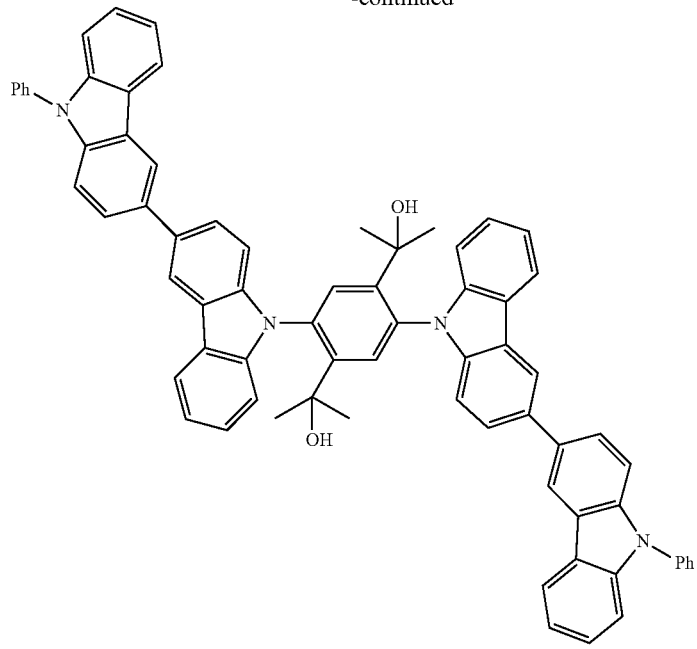

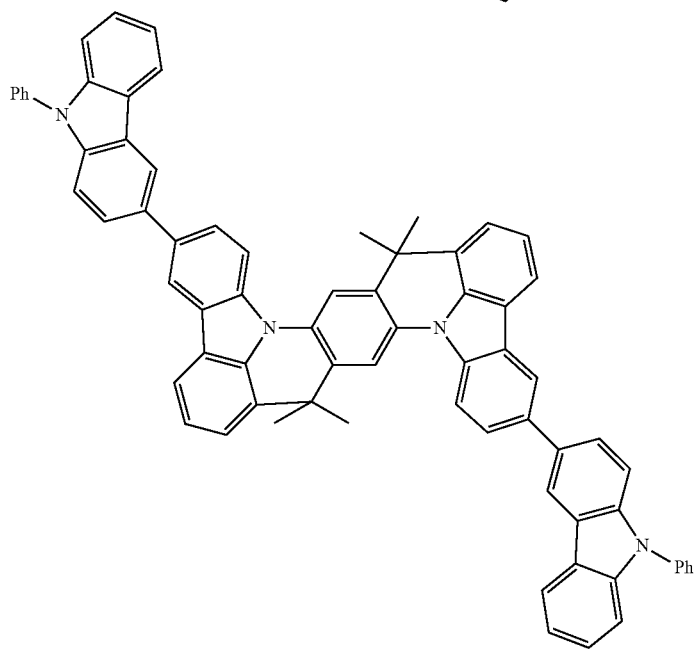

7 a) Dimethyl 2,5-bis-(9'-phenyl-9'H-[3,3']bicarbazolyl-9-yl)terephthalate

The compound is synthesised by the same procedure as for the corresponding step of Example 5 by reaction of 13.6 g (43 mmol) of diethyl dibromoterephthalate and 39 g (95.9 mmol) of 9-phenyl-3,3'-bicarbazole. The pure product is obtained by recrystallisation. The yield is 31 g (31 mmol), corresponding to 80% of theory.

b) 2-[4-(1-Hydroxy-1-methylethyl)-2,5-bis-(9'-phenyl-9'H-[3,3']bicarbazolyl-9-yl)phenyl]propan-2-ol The compound is synthesised by the same procedure as for the corresponding step of Example 5 by reaction of 140.9 g (140 mmol) of dimethyl 2,5-bis-(9'-phenyl-9'H-[3,3']bicarbazolyl-9-yl)terephthalate with 400 ml (600 mmol) of 1.6 M methyllithium solution. The yield is 110 g (109 mmol), corresponding to 79% of theory.

c) Cyclisation to Compound 7

The compound is synthesised by the same procedure as for the corresponding step of Example 5 by reaction of 45.3 g (45 mmol) of 2-[4-(1-hydroxy-1-methylethyl)-2,5-bis-(9'-phenyl-9'H-[3,3']bicarbazolyl-9-yl)phenyl]propan-2-ol with 40 g of polyphosphoric acid and 28 ml of methanesulfonic acid. The solid obtained is washed by stirring with heptane. Yield: 28 g (29 mmol), 65% of theory, purity according to HPLC about 99.9%.

Synthesis of Compound 8

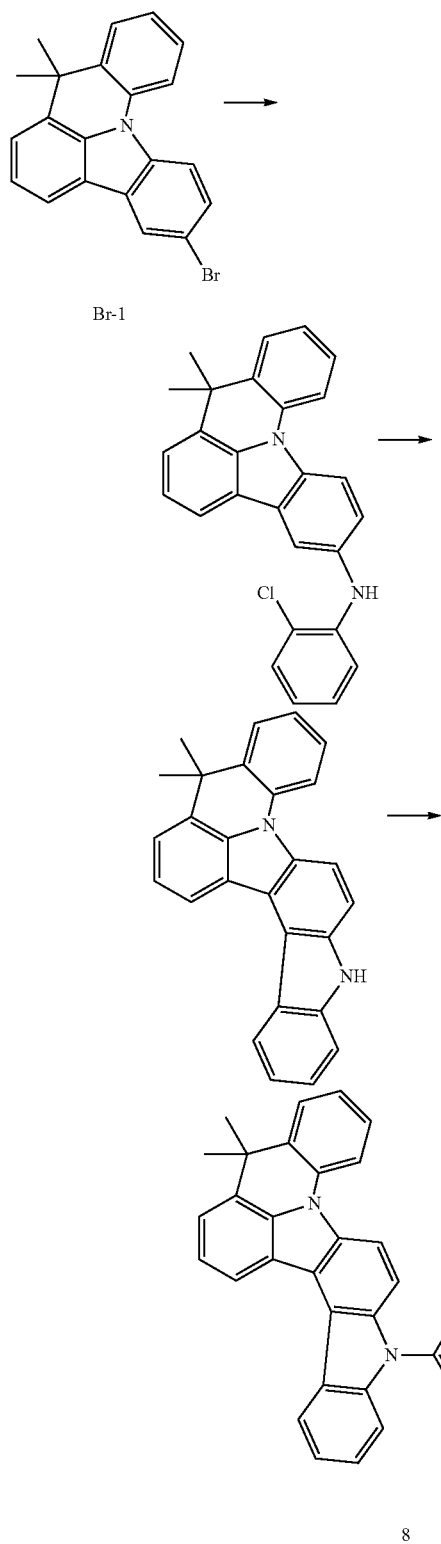

8 a) 2-Chlorophenyl-(8,8-dimethyl-8H-indolo[3,2,1-de]acridin-3-yl)amine 66.2 g (183 mmol) of 3-bromo-8,8-dimethyl-8H-indolo[3,2,1-de]acridine (Br-1), 28 g (220 mmol) of 2-chlorophenylamine, 1.5 g of DPPF (2.7 mmol), 0.5 g of palladium(II) acetate and 45 g of sodium tert-butoxide (486 mmol) are heated at the boil in 1.5 l of toluene for 18 h under a protective atmosphere. The mixture is subsequently partitioned between toluene and water, and the organic phase is washed three times with water and dried over $Na_2SO_4$ and evaporated in a rotary evaporator. The residue remaining is recrystallised from heptane/ethyl acetate. The yield is 43 g (107 mmol, 59%).

b) Cyclisation 2500 ml of dioxane are added to 135 g (332 mmol) of 2-chlorophenyl-(8,8-dimethyl-8H-indolo[3,2,1-de]acridin-3-yl)amine, 7.4 g (33.2 mmol) of palladium(II) acetate, 191 g (1.992 mol) of sodium tert-butoxide, 39.8 ml (39.8 mmol) of 1M $P(tBu)_3$ solution in toluene, and the mixture is stirred at 110° C. for 9 h. 2000 ml of water are then added. The mixture is extracted with 2000 ml of ethyl acetate, and the combined organic phases are dried over $Na_2SO_4$ and evaporated in a rotary evaporator. The residue is recrystallised from toluene/heptane. The yield is 62 g (168 mmol, 51%).

c) Conversion into the Pyrimidine Derivative (Compound 8)

4.2 g of 60% NaH in mineral oil (106 mmol) are dissolved in 300 ml of dimethylformamide under a protective atmosphere. 39 g (106 mol) of the precursor from reaction b) are dissolved in 250 ml of DMF and added dropwise to the reaction mixture. After 1 h at room temperature, a solution of 2-chloro-4,6-diphenyl-1,3-pyrimidine (34.5 g, 0.122 mol) in 200 ml of THF is added dropwise. The reaction mixture is then stirred at room temperature for 12 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane and finally sublimed in a high vacuum. The purity is 99.9%, the yield is 28 g (46 mmol, 43%).

Synthesis of Compound 9

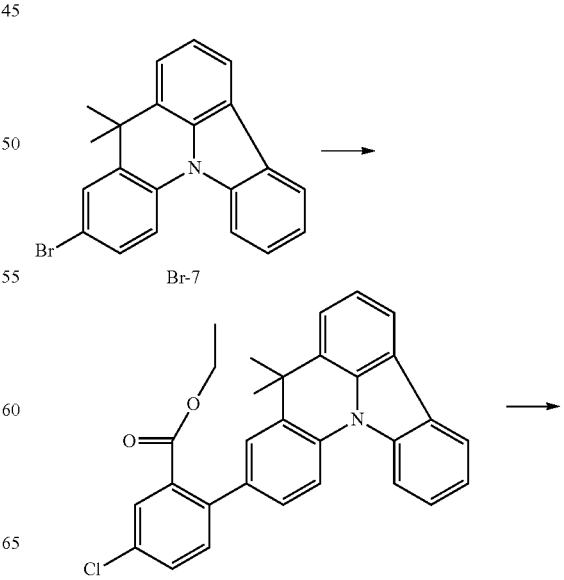

113
-continued

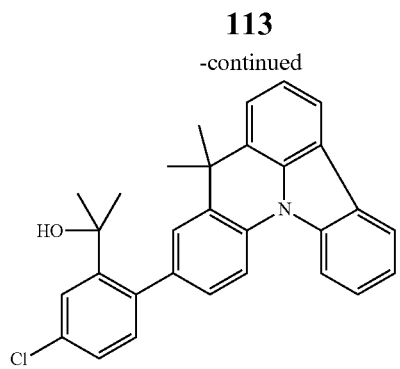

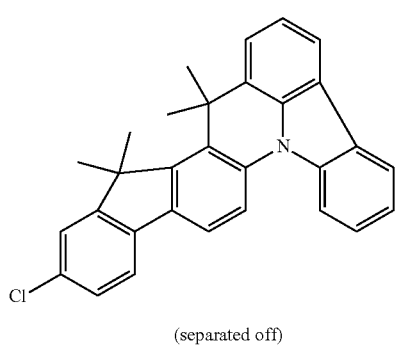
(separated off)

+

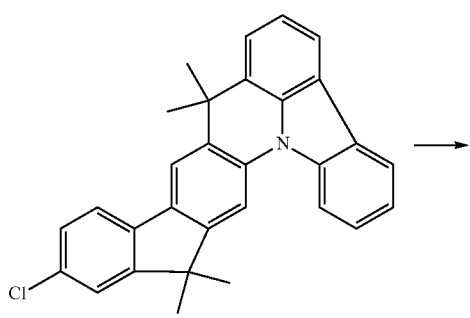

→

114
-continued

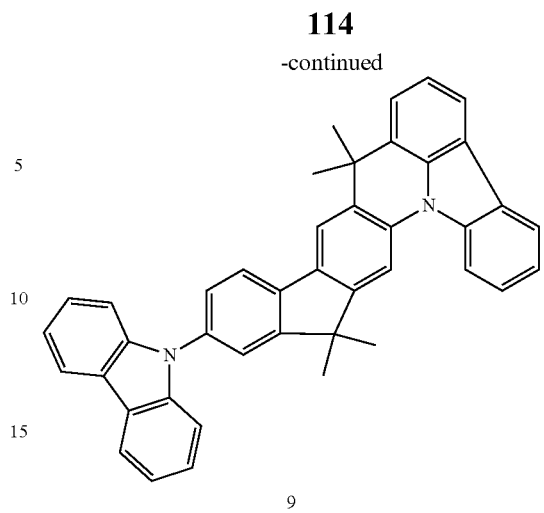

9

Compound 9 is synthesised analogously to compound 2 by reaction of 3-bromo-8,8-dimethyl-8H-indolo[3,2,1-de]acridine (110 mmol) with [4-chloro-2-(ethoxycarbonyl)phenyl] boronic acid (110.0 mmol) and subsequent cyclisation. The residue is recrystallised from toluene and dichloromethane/isopropanol. The isomers (ratio 70:30) can be separated by recrystallisation from toluene/acetonitrile. The yield of the isomer mixture is 55.2 g (127 mmol), corresponding to 64% of theory. A degassed solution of 37 g (86.6 mmol) of the desired isomer and 15.8 g (95.9 mmol) of carbazole is subsequently dissolved in 1000 ml of dioxane, and the solution is saturated with $N_2$ for 1 h. Then, firstly 0.9 ml (4.3 mmol) of P($^t$Bu)$_3$, then 0.480 g (2.1 mmol) of palladium acetate are added to the solution, and 12.6 g (131 mmol) of NaOtBu in the solid state are subsequently added. The reaction mixture is heated under reflux for 18 h. After cooling to room temperature, 1000 ml of water are carefully added. The organic phase is washed with 4×50 ml of $H_2O$ and dried over $MgSO_4$, and the solvents are removed in vacuo. The residue is recrystallised from toluene and from chlorobenzene and finally sublimed in a high vacuum. The purity is 99.9%. The yield is 23.8 g (43 mmol), corresponding to 51% of theory.

Synthesis of Compounds 10a-10n

Synthesis of Compound 10a

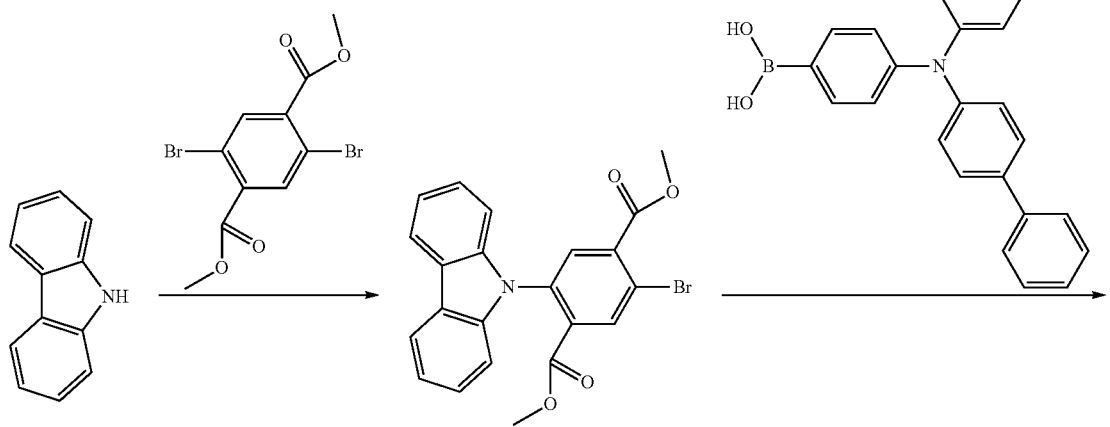

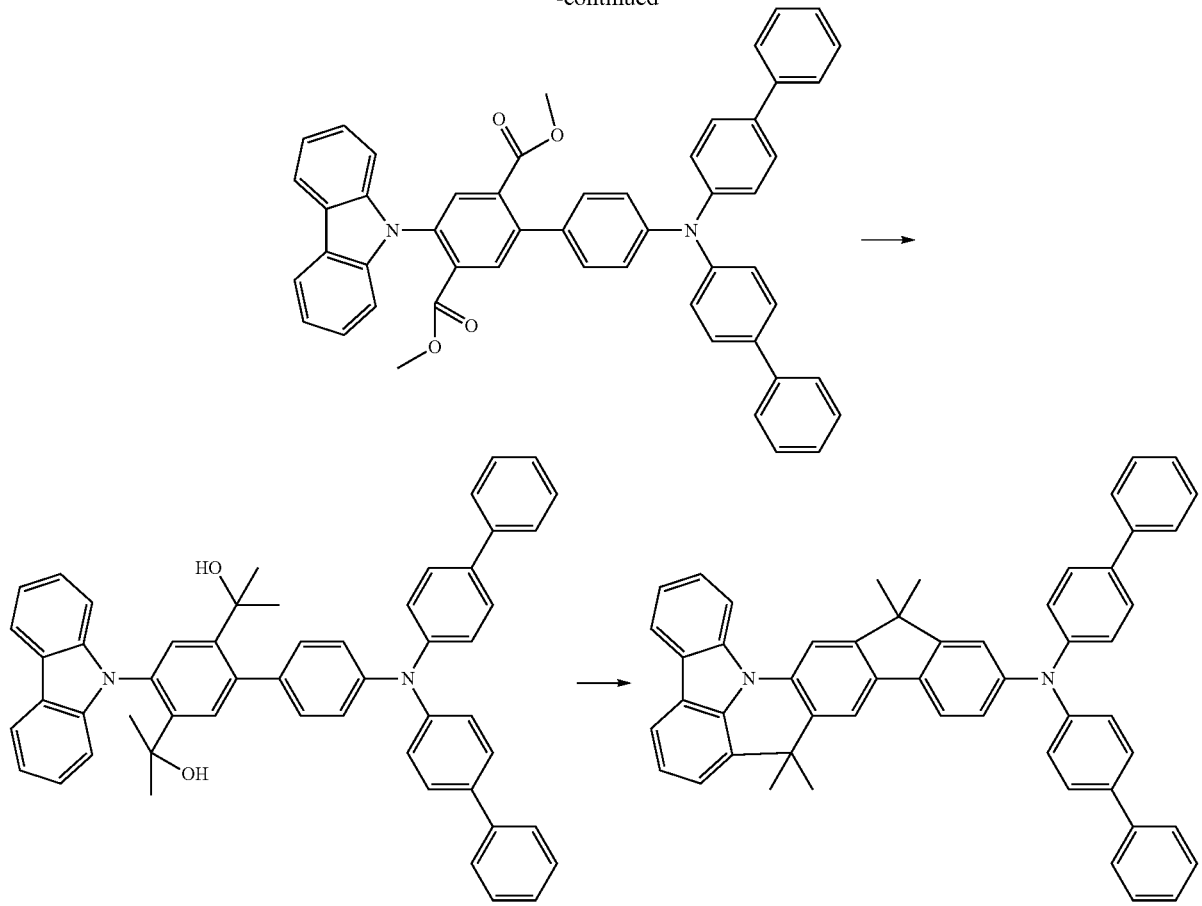

Dimethyl 2-bromo-5-carbazol-9-ylterephthalate

A degassed solution of 157.6 g (400 mmol) of diethyl dibromoterephthalate and 36.7 g (220 mmol) of carbazole in 1 l of 1,2-dichlorobenzene is saturated with $N_2$ for 1 h. Then, firstly 20 g (314 mmol) of copper powder, then 18 g (67 mmol) of 18-crown-6 are added to the solution, and 177 g (850 mmol) of potassium carbonate as the solid are subsequently added. The reaction mixture is heated at 170° C. for 18 h. After cooling to room temperature, 1 l of water is carefully added. The organic phase is washed with 4×50 ml of $H_2O$ and dried over $MgSO_4$, and the solvents are removed in vacuo. The pure product is obtained by recrystallisation. The yield is 83 g (177 mmol), corresponding to 81% of theory.

Dimethyl 4'-(bisbiphenyl-4-ylamino)-4-carbazol-9-ylbiphenyl-2,5-dicarboxylate 91 g (207 mol) of bisbiphenyl-4-yl-(4-boronophenyl)amine, 207 g (474 mmol) of dimethyl 2-bromo-5-carbazol-9-ylterephthalate and 315.9 g (2.29 mol) of potassium carbonate are initially introduced in a mixture of 850 ml of toluene and 850 ml of water and saturated with $N_2$ for 30 min. After addition of 1.36 g (1.18 mmol) of $Pd(PPh_3)_4$, the mixture is heated at the boil for 4 h. After cooling to RT and addition of 400 ml of EtOH, the mixture is cooled to room temperature and stirred for 1 h, and the precipitate is filtered off with suction, washed with water, EtOH and heptane and dried at 80° C. in vacuo. The yield is 254 g (336 mmol), corresponding to 72% of theory.

2-[4'-(Bisbiphenyl-4-ylamino)-4-carbazol-9-yl-5-(1-hydroxy-1-methylethyl)biphenyl-2-yl]propan-2-ol 105 g (140 mmol) of dimethyl 4'-(bisbiphenyl-4-ylamino)-4-carbazol-9-yl-biphenyl-2,5-dicarboxylate are initially introduced in 600 ml of THF and cooled to −70° C., and 400 ml (600 mmol) of 1.6 M methyllithium solution are added dropwise at −70° C. over the course of 60 min. After 2 h at −70° C., firstly 30 ml of ice-water, then 60 ml of 50% acetic acid are added dropwise, the reaction mixture is worked up by extraction with ethyl acetate/water, and the organic phase is dried over $Na_2SO_4$ and freed from solvent in vacuo. The yield is 85 g (112 mmol), corresponding to 85% of theory.

Cyclisation to Compound 10a:

33.9 g (45 mmol) of 2-[4'-(bisbiphenyl-4-ylamino)-4-carbazol-9-yl-5-(1-hydroxy-1-methylethyl)biphenyl-2-yl]propan-2-ol are dissolved in 1.2 l of degassed toluene, a suspension of 40 g of polyphosphoric acid and 28 ml of methanesulfonic acid is added, and the mixture is heated at 60° C. for 1 h. The batch is cooled, and water is added. A solid precipitates out and is dissolved in methylene chloride/THF (1:1). The solution is carefully rendered alkaline using 20% NaOH, the phases are separated and dried over $MgSO_4$. The solid obtained is washed by stirring with heptane. Yield: 22.5 g (31 mmol), 70% of theory, purity according to HPLC about 99.9%.

Compounds 10b-10n are obtained analogously:

| Ex. | Starting material 1 | Starting material 2 | Product | Yield |
|---|---|---|---|---|
| 10b | | 1251772-97-0 | | 62% |
| 10c | see above | 1246021-99-7 | | 73% |
| 10d | see above | 1246021-63-5 | | 72% |
| 10e | see above | 1246021-61-3 | | 68% |

-continued
| Ex. | Starting material 1 | Starting material 2 | Product | Yield |
|---|---|---|---|---|
| 10f | see above | 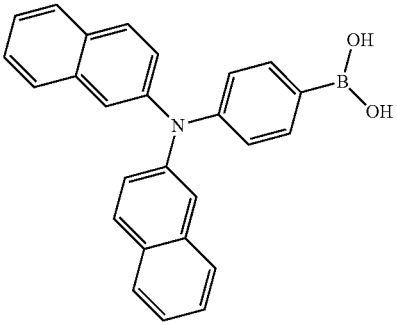<br>1232102-18-9 | 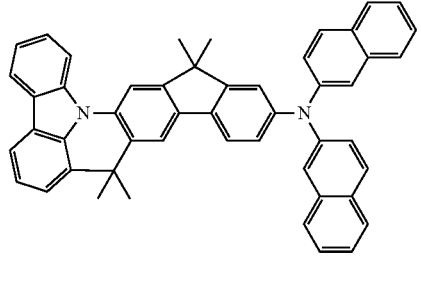 [SMILES: CC1(C)c2cc(N(c3ccc4ccccc4c3)c3ccc4ccccc4c3)ccc2-c2cc3c(cc21)-n1c2ccccc2c2cccc(c21)C3(C)C] | 75% |
| 10g | see above | 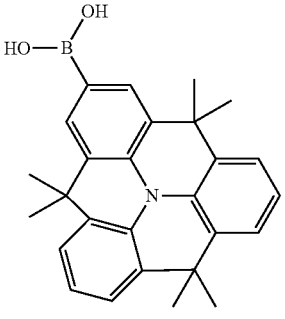<br>1207594-82-8 | 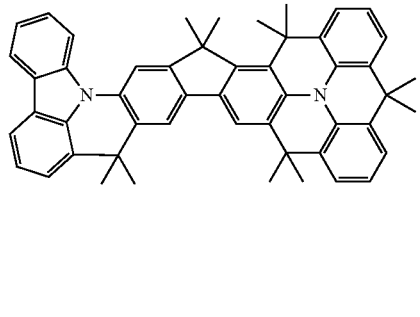 [SMILES: CC1(C)c2cccc3c2N2c4c1cccc4C(C)(C)c1c2c(cc2c1C(C)(C)c1cc4c(cc1-2)C(C)(C)c1cccc2c5ccccc5n-4c12)C3(C)C] | 77% |
| 10h | see above | 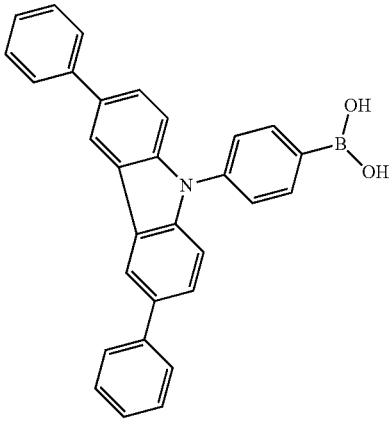<br>1149804-38-5 | 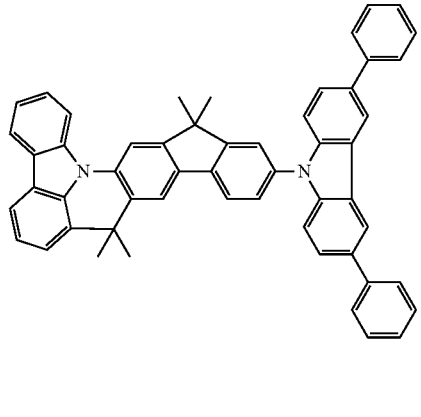 [SMILES: CC1(C)c2cc(-n3c4ccc(-c5ccccc5)cc4c4cc(-c5ccccc5)ccc43)ccc2-c2cc3c(cc21)-n1c2ccccc2c2cccc(c21)C3(C)C] | 65% |
| 10i | see above | 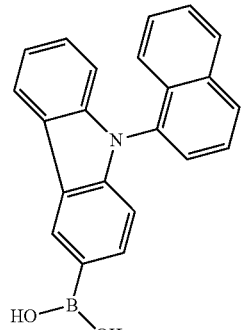<br>1133057-97-2 | 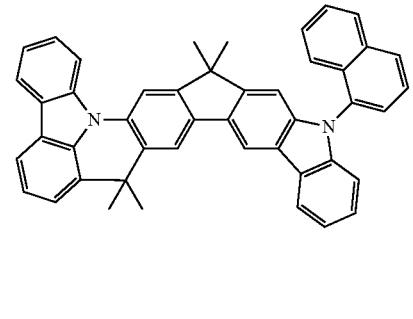 [SMILES: CC1(C)c2cc3c(cc2-c2cc4c5ccccc5n(-c5cccc6ccccc56)c4cc21)C(C)(C)c1cccc2c4ccccc4n-3c12] | 68% |

-continued
| Ex. | Starting material 1 | Starting material 2 | Product | Yield |
|---|---|---|---|---|
| 10j | see above | 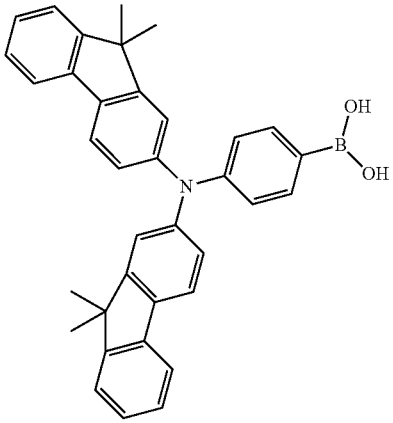<br>1079300-11-0 | 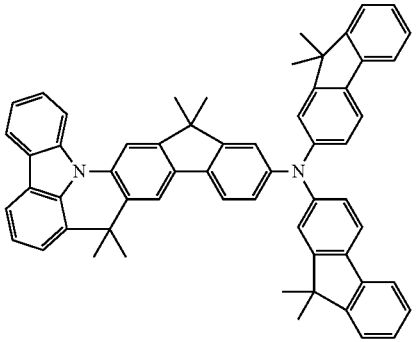 [SMILES: CC1(C)c2ccccc2-c2ccc(N(c3ccc4c(c3)C(C)(C)c3ccccc3-4)c3ccc4c(c3)C(C)(C)c3cc5c(cc3-4)C(C)(C)c3cccc4c6ccccc6n-5c34)cc21] | 75% |
| 10k | see above | 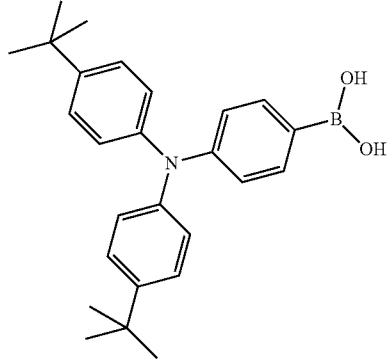<br>875148-46-2 | 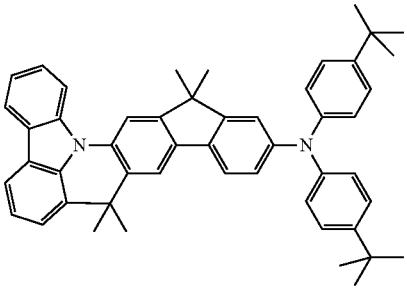 [SMILES: CC(C)(C)c1ccc(N(c2ccc(C(C)(C)C)cc2)c2ccc3c(c2)C(C)(C)c2cc4c(cc2-3)C(C)(C)c2cccc3c5ccccc5n-4c23)cc1] | 79% |
| 10l | see above | 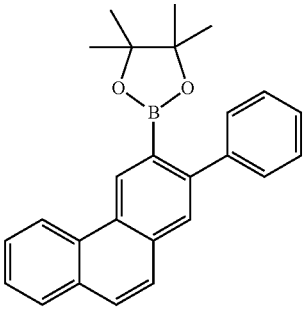<br>1242770-93-9 | 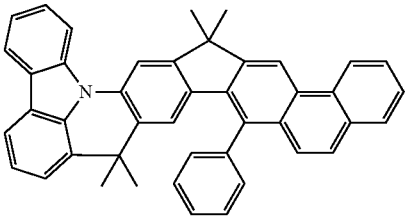 [SMILES: CC1(C)c2cc3c(cc2-c2c1cc1c(ccc4ccccc41)c2-c1ccccc1)C(C)(C)c1cccc2c4ccccc4n-3c12] | 68% |

-continued

| Ex. | Starting material 1 | Starting material 2 | Product | Yield |
|---|---|---|---|---|
| 10m | see above | 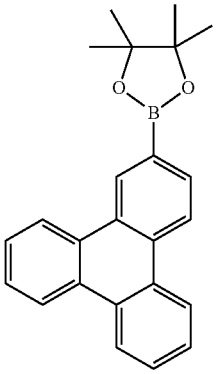<br>890042-13-4 | 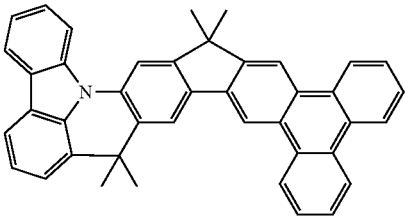 [SMILES: CC1(C)c2cc3c(cc2-c2cc4c5ccccc5c5ccccc5c4cc21)C(C)(C)c1cccc2c4ccccc4n-3c12] | 64% |
| 10n | see above | 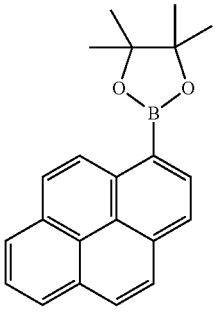<br>349666-24-6 | 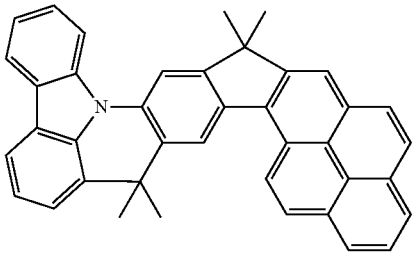 [SMILES: CC1(C)c2cc3c(cc2-c2c1cc1ccc4cccc5ccc2c1c45)C(C)(C)c1cccc2c4ccccc4n-3c12] | 69% |

III) Device Examples
Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples C1 to I47 below (see Tables 1 and 2). Glass plates coated with structured ITO (indium tin oxide) in a thickness of 150 nmk are coated with 20 nm of PEDOT (poly(3,4-ethylenedioxy-2,5-thiophene), applied by spin coating from water; purchased from H.C. Starck, Goslar, Germany) for improved processing. These coated glass plates form the substrates to which the OLEDs are applied. The OLEDs basically have the following layer structure: substrate/optional hole-injection layer (HIL)/optional hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is revealed by Table 1 below. The materials required for the production of the OLEDs are shown in Table 3 below.

All materials are applied by thermal vapour deposition in a vacuum chamber. The emission layer here always consists of at least one matrix material (host material) and an emitting dopant (emitter), with which the matrix material or matrix materials is (are) mixed by co-evaporation in a certain proportion by volume. An expression such as ST1:CBP:TER1 (55%:35%:10%) here means that material ST1 is present in the layer in a proportion by volume of 55%, CBP is present in the layer in a proportion of 35% and TER1 is present in the layer in a proportion of 10%. Other layers may also analogously consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), and the lifetime are determined. The electroluminescence spectrum are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiency respectively achieved at 1000 cd/m$^2$. Finally, EQE1000 denotes the external quantum efficiency at an operating luminous density of 1000 cd/m$^2$. The lifetime LT is defined as the time after which the luminous density has dropped from the initial luminous density L0 to a certain proportion L1 on operation at constant current. The expressions L0=4000 cd/m$^2$ and L1=80% in Table 2 mean that the lifetime indicated in column LT corresponds to the time after which the initial luminous density has dropped from 4000 cd/m$^2$ to 3200 cd/m$^2$. The values for the lifetime can be converted into a figure for other initial luminous densities with the aid of conversion formulae known to the person skilled in the art. The lifetime for an initial luminous density of 1000 cd/m$^2$ is the usual specification here.

The data for the various OLEDs are summarised in Table 2. Example C1-C13 are comparative examples in accordance with the prior art, while Examples I1-I47 show data for OLEDs comprising materials according to the invention.

Some of the examples are explained in greater detail below in order to illustrate the advantages of the compounds according to the invention. However, it should be pointed out that this only represents a selection of the data shown in Table 2. As can be seen in the table, significant improvements over the prior art are also achieved on use of the compounds according to the invention that are not mentioned in greater detail, in some cases in all parameters, but in some cases only an improvement in the efficiency or voltage or lifetime can be observed. However, even the improvement of one of the said parameters represents a significant advance since different applications require optimisation with respect to different parameters.

Use of Compounds According to the Invention as Hole-Injection or Hole-Transport Material OLEDs $C_1$-$C_3$ are comparative examples in accordance with the prior art in which fluorescent dopants D1-D3 are employed in combination with matrix materials M1 and M2, hole-transport materials SpA1, SpNPB and NPB and electron-transport materials $Alq_3$, ETM1 and ST2.

OLEDs C4, C5, C7-C9 and C13 are comparative examples in accordance with the prior art in which phosphorescent emitters TEG1, TER1 and TER2 are employed in combination with matrix materials ST1 and CBP, hole-transport materials SpA1, NPB and BPA1 and electron-transport materials $Alq_3$ and ST1.

If NPB is replaced by material HTM4 according to the invention, a significant increase in the lifetime by about 45% (Examples C1, I10), in particular, is obtained for blue-fluorescent OLEDs. The voltage and current efficiency improve slightly, giving an approximately 10% better power efficiency. In combination with the pure hydrocarbon D3 as emitter, a very significant improvement in the lifetime by almost 50% is likewise obtained with compound HTM3 according to the invention compared with NPB, while the power efficiency remains unchanged (Examples C3 and I6). On use of HTM4 in phosphorescent OLEDs, an improvement in the lifetime by somewhat more than 50% compared with the prior art BPA1 (Examples C5 and I11) is obtained. An improvement in the voltage and current efficiency furthermore produces an up to 25% increased power efficiency (Examples C9 and I12).

Use in a mixed hole-transport layer (in this respect see the unpublished application DE 102010010481.7) also enables improved data to be achieved with the materials according to the invention. Thus, mixing of BPA1 and M4 or M5 produces a 25% increased lifetime compared with BPA1 alone (Examples C5, I20 and I21). The power efficiency remains approximately the same.

The use of compounds according to the invention on the hole-transport side of OLEDs thus produces significant improvements with respect to lifetime, operating voltage and efficiency.

Use of Compounds According to the Invention as Matrix Materials in Phosphorescent OLEDs Compounds according to the invention can furthermore be employed in the emission layer of phosphorescent OLEDs, either as individual component (Examples I14-I16) or as component in a mixed-matrix system (Examples I17-I19, I28, I37-I46). Data for OLEDs comprising the materials ST1, Ket1 (individual materials) or DAP1, CPB, TCTA and FTPh for mixed-matrix systems (Examples C4-C6, C8-C13) are shown as comparative examples in accordance with the prior art.

Besides a significant improvement in the voltage and power efficiency by about 25%, a lifetime which is increased by somewhat more than 30% compared with ST1 is also obtained, in particular, with compound M3 according to the invention. Compared with Ket1, the improvement in the power efficiency is even clearer (Examples C4-C6, I14 and I15). In mixed-matrix systems, similar improvements are obtained through the use of compounds M4 and M5 (Examples C13, I18 and I19).

The materials according to the invention thus give rise to significant improvements compared with the prior art in all parameters, especially with respect to lifetime and power efficiency, on use as matrix materials in phosphorescent OLEDs. The considerable improvement in the power efficiency on use of the materials according to the invention is attributable, in particular, to the significant improvement in the operating voltage.

Use of Compounds According to the Invention as Deep-Blue Dopants

Furthermore, compounds according to the invention can be employed as blue-fluorescent dopants. On use of D4, deep-blue colour coordinates with a y coordinate of 0.12 are obtained with a quantum efficiency around 7% and a lifetime of about 170 h from 6000 cd/m$^2$ (Example I47).

TABLE 1

| | | | | | | | | |
|---|---|---|---|---|---|---|---|---|
| | | | | | | | | |
| Ex. | HIL Thickness | HTL Thickness | IL Thickness | EBL Thickness | EML Thickness | HBL Thickness | ETL Thickness | EIL Thickness |
| C1 | HATCN 5 nm | SpA1 140 nm | — | NPB 20 nm | M1:D1 (95%:5%) 30 nm | — | ETM1:LiQ (50%:50%) 20 nm | — |
| C2 | HATCN 5 nm | SpA1 110 nm | — | NPB 20 nm | M2:D2 (90%:10%) 30 nm | — | Alq$_3$ 20 nm | LiF 1 nm |
| C3 | HATCN 5 nm | SpNPB 40 nm | — | NPB 20 nm | M2:D3 (98.5%:1.5%) 30 nm | — | ST2:LiQ (50%:50%) 20 nm | — |
| C4 | — | SpA1 70 nm | HATCN 5 nm | BPA1 20 nm | ST1:TEG1 (90%:10%) 30 nm | — | ST1:LiQ (50%:50%) 30 nm | — |
| C5 | — | SpA1 70 nm | HATCN 5 nm | BPA1 20 nm | ST1:TEG1 (90%:10%) 30 nm | ST1 10 nm | ST1:LiQ (50%:50%) 30 nm | — |
| C6 | — | SpA1 70 nm | HATCN 5 nm | BPA1 90 nm | Ket1:TEG1 (90%:10%) 30 nm | — | ST1:LiQ (50%:50%) 40 nm | — |
| C7 | — | SpA1 20 nm | — | NPB 20 nm | ST1:TER1 (85%:15%) 30 nm | — | Alq$_3$ 20 nm | LiF 1 nm |
| C8 | — | SpA1 20 nm | — | NPB 20 nm | ST1:TER2 (85%:15%) 30 nm | — | Alq$_3$ 20 nm | LiF 1 nm |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| C9 | — | SpA1 70 nm | HATCN 5 nm | BPA1 90 nm | ST1:CBP:TEG1 (30%:60%:10%) 30 nm | ST1 10 nm | ST1:LiQ (50%:50%) 30 nm | — |
| C10 | — | SpA1 70 nm | HATCN 5 nm | BPA1 90 nm | ST1:TCTA:TEG1 (30%:60%:10%) 30 nm | — | ST1:LiQ (50%:50%) 30 nm | — |
| C11 | HATCN 20 nm | — | — | BPA1 20 nm | Ket1:FTPh:TEG1 (30%:60%:10%) 30 nm | Ket1 10 nm | ETM2 20 nm | LiF 1 nm |
| C12 | — | SpA1 70 nm | HATCN 5 nm | BPA1 90 nm | DAP1:CBP:TEG1 (30%:60%:10%) 30 nm | — | ST1:LiQ (50%:50%) 30 nm | — |
| C13 | — | SpA1 20 nm | — | NPB 20 nm | ST1:CBP:TER1 (45%:45%:10%) 30 nm | ST1 10 nm | Alq$_3$ 20 nm | LiF 1 nm |
| I1 | HATCN 5 nm | SpA1 140 nm | — | HTM1 20 nm | M1:D1 (95%:5%) 30 nm | — | ETM1:LiQ (50%:50%) 20 nm | — |
| I2 | — | SpA1 70 nm | HATCN 5 nm | HTM1 20 nm | ST1:TEG1 (90%:10%) 30 nm | ST1 10 nm | ST1:LiQ (50%:50%) 30 nm | — |
| I3 | HATCN 5 nm | HTM2 110 nm | — | NPB 20 nm | M2:D2 (90%:10%) 30 nm | — | Alq$_3$ 20 nm | LiF 1 nm |
| I4 | — | HTM2 70 nm | HATCN 5 nm | BPA1 20 nm | ST1:TEG1 (90%:10%) 30 nm | — | ST1:LiQ (50%:50%) 30 nm | — |
| I5 | — | SpA1 20 nm | — | HTM2 20 nm | ST1:TER2 (85%:15%) 30 nm | — | Alq$_3$ 20 nm | LiF 1 nm |
| I6 | HATCN 5 nm | SpNPB 40 nm | — | HTM3 20 nm | M2:D3 (98.5%:1.5%) 30 nm | — | ST2:LiQ (50%:50%) 20 nm | — |
| I7 | — | SpA1 20 nm | — | HTM3 20 nm | ST1:TER1 (85%:15%) 30 nm | — | Alq$_3$ 20 nm | LiF 1 nm |
| I8 | — | SpA1 70 nm | HATCN 5 nm | BPA1 90 nm | ST1:HTM3:TEG1 (30%:60%:10%) 30 nm | ST1 10 nm | ST1:LiQ (50%:50%) 30 nm | — |
| I9 | HATCN 20 nm | — | — | BPA1 20 nm | Ket1:HTM3:TEG1 (30%:60%:10%) 30 nm | Ket1 10 nm | ETM2 20 nm | LiF 1 nm |
| I10 | HATCN 5 nm | SpA1 140 nm | — | HTM4 20 nm | M1:D1 (95%:5%) 30 nm | — | ETM1:LiQ (50%:50%) 20 nm | — |
| I11 | — | SpA1 70 nm | HATCN 5 nm | HTM4 20 nm | ST1:TEG1 (90%:10%) 30 nm | ST1 10 nm | ST1:LiQ (50%:50%) 30 nm | — |
| I12 | — | SpA1 70 nm | HATCN 5 nm | HTM4 90 nm | ST1:CBP:TEG1 (30%:60%:10%) 30 nm | ST1 10 nm | ST1:LiQ (50%:50%) 30 nm | — |
| I13 | — | SpA1 20 nm | — | HTM4 20 nm | ST1:CBP:TER1 (45%:45%:10%) 30 nm | ST1 10 nm | Alq$_3$ 20 nm | LiF 1 nm |
| I14 | — | SpA1 70 nm | HATCN 5 nm | BPA1 20 nm | M3:TEG1 (90%:10%) 30 nm | — | ST1:LiQ (50%:50%) 30 nm | — |
| I15 | — | SpA1 70 nm | HATCN 5 nm | BPA1 20 nm | M3:TEG1 (90%:10%) 30 nm | ST1 10 nm | ST1:LiQ (50%:50%) 30 nm | — |
| I16 | — | SpA1 20 nm | — | NPB 20 nm | M3:TER2 (85%:15%) 30 nm | — | Alq$_3$ 20 nm | LiF 1 nm |
| I17 | — | SpA1 70 nm | HATCN 5 nm | BPA1 90 nm | M3:CBP:TEG1 (30%:60%:10%) 30 nm | ST1 10 nm | ST1:LiQ (50%:50%) 30 nm | — |
| I18 | — | SpA1 20 nm | — | NPB 20 nm | ST1:M4:TER1 (45%:45%:10%) 30 nm | ST1 10 nm | Alq$_3$ 20 nm | LiF 1 nm |
| I19 | — | SpA1 20 nm | — | NPB 20 nm | ST1:M5:TER1 (45%:45%:10%) 30 nm | ST1 10 nm | Alq$_3$ 20 nm | LiF 1 nm |
| I20 | — | SpA1 70 nm | HATCN 5 nm | BPA1:M4 (55%:45%) 20 nm | ST1:TEG1 (90%:10%) 30 nm | ST1 10 nm | ST1:LiQ (50%:50%) 30 nm | — |
| I21 | — | SpA1 70 nm | HATCN 5 nm | BPA1:M5 (55%:45%) 20 nm | ST1:TEG1 (90%:10%) 30 nm | ST1 10 nm | ST1:LiQ (50%:50%) 30 nm | — |
| I22 | HATCN 5 nm | HTM5 140 nm | — | NPB 20 nm | M1:D1 (95%:5%) 30 nm | — | ETM1:LiQ (50%:50%) 20 nm | — |
| I23 | HATCN 5 nm | HTM6 40 nm | — | NPB 20 nm | M2:D3 (98.5%:1.5%) 30 nm | — | ST2:LiQ (50%:50%) 20 nm | — |
| I24 | — | HTM7 70 nm | HATCN 5 nm | BPA1 20 nm | ST1:TEG1 (90%:10%) 30 nm | ST1 10 nm | ST1:LiQ (50%:50%) 30 nm | — |
| I25 | HATCN 5 nm | HTM8 140 nm | — | NPB 20 nm | M1:D1 (95%:5%) 30 nm | — | ETM1:LiQ (50%:50%) 20 nm | — |
| I26 | HATCN 5 nm | SpA1 140 nm | — | HTM9 20 nm | M1:D1 (95%:5%) 30 nm | — | ETM1:LiQ (50%:50%) 20 nm | — |
| I27 | — | SpA1 70 nm | HATCN 5 nm | HTM10 20 nm | ST1:TEG1 (90%:10%) 30 nm | — | ST1:LiQ (50%:50%) 30 nm | — |
| I28 | — | SpA1 70 nm | HATCN 5 nm | BPA1 90 nm | ST1:HTM10:TEG1 (30%:60%:10%) 30 nm | ST1 10 nm | ST1:LiQ (50%:50%) 30 nm | — |
| I29 | — | SpA1 70 nm | HATCN 5 nm | HTM11 20 nm | ST1:TEG1 (90%:10%) 30 nm | — | ST1:LiQ (50%:50%) 30 nm | — |
| I30 | HATCN 5 nm | SpA1 140 nm | — | HTM12 20 nm | M1:D1 (95%:5%) 30 nm | — | ETM1:LiQ (50%:50%) 20 nm | — |
| I31 | HATCN 5 nm | SpA1 140 nm | — | HTM13 20 nm | M1:D1 (95%:5%) 30 nm | — | ETM1:LiQ (50%:50%) 20 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| I32 | — | SpA1 70 nm | HATCN 5 nm | HTM14 20 nm | ST1:TEG1 (90%:10%) 30 nm | — | ST1:LiQ (50%:50%) 30 nm | — |
| I33 | — | SpA1 70 nm | HATCN 5 nm | HTM15 20 nm | ST1:TEG1 (90%:10%) 30 nm | — | ST1:LiQ (50%:50%) 30 nm | — |
| I34 | — | SpA1 70 nm | HATCN 5 nm | HTM16 20 nm | ST1:TEG1 (90%:10%) 30 nm | — | ST1:LiQ (50%:50%) 30 nm | — |
| I35 | — | SpA1 70 nm | HATCN 5 nm | HTM17 90 nm | Ket1:TEG1 (90%:10%) 30 nm | — | ST1:LiQ (50%:50%) 40 nm | — |
| I36 | HATCN 5 nm | SpNPB 40 nm | — | HTM18 20 nm | M2:D3 (98.5%:1.5%) 30 nm | — | ST2:LiQ (50%:50%) 20 nm | — |
| I37 | — | SpA1 20 nm | — | NPB 20 nm | ST1:M6:TER1 (45%:45%:10%) 30 nm | ST1 10 nm | Alq$_3$ 20 nm | LiF 1 nm |
| I38 | — | SpA1 20 nm | — | NPB 20 nm | ST1:M7:TER1 (45%:45%:10%) 30 nm | ST1 10 nm | Alq$_3$ 20 nm | LiF 1 nm |
| I39 | — | SpA1 20 nm | — | NPB 20 nm | ST1:M8:TER1 (45%:45%:10%) 30 nm | ST1 10 nm | Alq$_3$ 20 nm | LiF 1 nm |
| I40 | — | SpA1 20 nm | — | NPB 20 nm | ST1:M9:TER1 (45%:45%:10%) 30 nm | ST1 10 nm | Alq$_3$ 20 nm | LiF 1 nm |
| I41 | — | SpA1 70 nm | HATCN 5 nm | BPA1 90 nm | ST1:M10:TEG1 (30%:60%:10%) 30 nm | ST1 10 nm | ST1:LiQ (50%:50%) 30 nm | — |
| I42 | — | SpA1 70 nm | HATCN 5 nm | BPA1 90 nm | ST1:M11:TEG1 (30%:60%:10%) 30 nm | ST1 10 nm | ST1:LiQ (50%:50%) 30 nm | — |
| I43 | — | SpA1 20 nm | — | NPB 20 nm | ST1:M11:TER1 (45%:45%:10%) 30 nm | ST1 10 nm | Alq$_3$ 20 nm | LiF 1 nm |
| I44 | — | SpA1 70 nm | HATCN 5 nm | BPA1 90 nm | ST1:M12:TEG1 (30%:60%:10%) 30 nm | ST1 10 nm | ST1:LiQ (50%:50%) 30 nm | — |
| I45 | — | SpA1 70 nm | HATCN 5 nm | BPA1 90 nm | DAP1:M12:TEG1 (30%:60%:10%) 30 nm | — | ST1:LiQ (50%:50%) 30 nm | — |
| I46 | — | SpA1 20 nm | — | NPB 20 nm | ST1:M12:TER1 (45%:45%:10%) 30 nm | ST1 10 nm | Alq$_3$ 20 nm | LiF 1 nm |
| I47 | HATCN 5 nm | SpNPB 40 nm | — | NPB 20 nm | M2:D4 (97%:3%) 30 nm | — | ST2:LiQ (50%:50%) 20 nm | — |

TABLE 2

Data for the OLEDs

| Ex. | U1000 (V) | CE1000 (cd/A) | PE1000 (lm/W) | EQE 1000 | CIE x/y at 1000 cd/m² | L0 (cd/m²) | L1 % | LT (h) |
|---|---|---|---|---|---|---|---|---|
| C1 | 4.7 | 8.1 | 5.4 | 6.3% | 0.14/0.16 | 6000 | 50 | 145 |
| C2 | 5.0 | 17.1 | 10.7 | 5.0% | 0.28/0.61 | 25000 | 50 | 480 |
| C3 | 4.3 | 9.8 | 7.1 | 7.6% | 0.14/0.16 | 6000 | 50 | 210 |
| C4 | 4.1 | 50 | 38 | 13.9% | 0.37/0.61 | 4000 | 80 | 310 |
| C5 | 4.2 | 52 | 39 | 14.5% | 0.36/0.60 | 4000 | 80 | 330 |
| C6 | 3.9 | 41 | 33 | 11.0% | 0.36/0.61 | 4000 | 80 | 315 |
| C7 | 5.0 | 7.2 | 4.5 | 12.0% | 0.69/0.31 | 1000 | 50 | 14000 |
| C8 | 6.5 | 9.0 | 4.3 | 8.3% | 0.66/0.33 | 1000 | 50 | 18000 |
| C9 | 4.4 | 48 | 34 | 13.3% | 0.37/0.60 | 4000 | 80 | 450 |
| C10 | 4.2 | 43 | 32 | 12.0% | 0.35/0.60 | 4000 | 80 | 195 |
| C11 | 4.3 | 45 | 33 | 12.6% | 0.36/0.61 | 4000 | 80 | 420 |
| C12 | 4.6 | 47 | 32 | 13.2% | 0.36/0.60 | 4000 | 80 | 490 |
| C13 | 5.2 | 8.1 | 4.9 | 11.4% | 0.68/0.32 | 1000 | 50 | 15000 |
| I1 | 4.5 | 8.6 | 6.0 | 6.7% | 0.14/0.16 | 6000 | 50 | 200 |
| I2 | 4.2 | 54 | 40 | 15.0% | 0.36/0.60 | 4000 | 80 | 470 |
| I3 | 4.7 | 17.6 | 11.8 | 5.1% | 0.28/0.61 | 25000 | 50 | 565 |
| I4 | 3.9 | 51 | 41 | 14.3% | 0.37/0.61 | 4000 | 80 | 335 |
| I5 | 6.2 | 9.4 | 4.8 | 8.7% | 0.66/0.33 | 1000 | 50 | 24000 |
| I6 | 4.2 | 9.5 | 7.1 | 7.4% | 0.14/0.16 | 6000 | 50 | 310 |
| I7 | 5.1 | 7.7 | 4.7 | 12.8% | 0.69/0.31 | 1000 | 50 | 20000 |
| I8 | 3.9 | 53 | 42 | 14.6% | 0.37/0.60 | 4000 | 80 | 565 |
| I9 | 3.7 | 48 | 41 | 13.4% | 0.36/0.60 | 4000 | 80 | 540 |
| I10 | 4.6 | 8.5 | 5.9 | 6.6% | 0.14/0.16 | 6000 | 50 | 210 |
| I11 | 4.2 | 56 | 42 | 15.6% | 0.36/0.61 | 4000 | 80 | 505 |
| I12 | 4.2 | 58 | 43 | 14.7% | 0.36/0.60 | 4000 | 80 | 570 |
| I13 | 5.1 | 8.7 | 5.3 | 12.2% | 0.68/0.32 | 1000 | 50 | 22000 |
| I14 | 3.5 | 53 | 48 | 14.8% | 0.37/0.61 | 4000 | 80 | 440 |
| I15 | 3.6 | 54 | 47 | 15.1% | 0.36/0.60 | 4000 | 80 | 455 |

TABLE 2-continued
Data for the OLEDs
| Ex. | U1000 (V) | CE1000 (cd/A) | PE1000 (lm/W) | EQE 1000 | CIE x/y at 1000 cd/m² | L0 (cd/m²) | L1 % | LT (h) |
|---|---|---|---|---|---|---|---|---|
| I16 | 5.8 | 10.0 | 5.4 | 9.2% | 0.66/0.33 | 1000 | 50 | 31000 |
| I17 | 3.9 | 52 | 42 | 14.5% | 0.37/0.60 | 4000 | 80 | 600 |
| I18 | 4.4 | 7.7 | 5.5 | 10.9% | 0.68/0.32 | 1000 | 50 | 19000 |
| I19 | 4.4 | 8.7 | 6.2 | 12.2% | 0.68/0.32 | 1000 | 50 | 21000 |
| I20 | 4.3 | 55 | 40 | 15.1% | 0.36/0.60 | 4000 | 80 | 390 |
| I21 | 4.3 | 52 | 38 | 14.4% | 0.36/0.60 | 4000 | 80 | 410 |
| I22 | 4.5 | 8.4 | 5.8 | 6.5% | 0.14/0.16 | 6000 | 50 | 155 |
| I23 | 4.2 | 10.0 | 7.5 | 7.8% | 0.14/0.16 | 6000 | 50 | 230 |
| I24 | 4.2 | 40 | 54 | 15.1% | 0.36/0.60 | 4000 | 80 | 345 |
| I25 | 4.7 | 8.3 | 5.6 | 6.4% | 0.14/0.16 | 6000 | 50 | 165 |
| I26 | 4.6 | 9.5 | 6.6 | 7.4% | 0.14/0.16 | 6000 | 50 | 160 |
| I27 | 4.3 | 56 | 41 | 15.5% | 0.36/0.60 | 4000 | 80 | 360 |
| I28 | 4.2 | 53 | 40 | 14.7% | 0.36/0.61 | 4000 | 80 | 530 |
| I29 | 4.3 | 55 | 40 | 15.4% | 0.36/0.60 | 4000 | 80 | 380 |
| I30 | 4.6 | 8.6 | 5.9 | 6.7% | 0.14/0.16 | 6000 | 80 | 135 |
| I31 | 4.6 | 7.7 | 5.3 | 6.0% | 0.14/0.16 | 6000 | 80 | 170 |
| I32 | 4.2 | 54 | 40 | 15.0% | 0.36/0.61 | 4000 | 80 | 350 |
| I33 | 4.1 | 53 | 41 | 14.6% | 0.37/0.60 | 4000 | 80 | 285 |
| I34 | 4.0 | 56 | 43 | 15.4% | 0.36/0.60 | 4000 | 80 | 300 |
| I35 | 3.9 | 49 | 40 | 13.6% | 0.36/0.60 | 4000 | 80 | 410 |
| I36 | 4.4 | 9.2 | 6.6 | 7.1% | 0.14/0.16 | 6000 | 50 | 270 |
| I37 | 4.7 | 8.1 | 5.5 | 11.5% | 0.68/0.32 | 1000 | 50 | 22000 |
| I38 | 4.2 | 7.0 | 5.2 | 9.8% | 0.67/0.31 | 1000 | 50 | 13000 |
| I39 | 4.7 | 7.3 | 4.9 | 10.3% | 0.68/0.32 | 1000 | 50 | 17000 |
| I40 | 4.3 | 8.6 | 6.3 | 12.1% | 0.68/0.32 | 1000 | 50 | 20000 |
| I41 | 4.2 | 53 | 40 | 14.8% | 0.36/0.61 | 4000 | 80 | 530 |
| I42 | 4.3 | 49 | 36 | 13.6% | 0.36/0.60 | 4000 | 80 | 480 |
| I43 | 4.9 | 6.7 | 4.3 | 9.5% | 0.68/0.32 | 1000 | 50 | 20000 |
| I44 | 4.1 | 52 | 40 | 14.5% | 0.37/0.61 | 4000 | 80 | 520 |
| I45 | 4.4 | 51 | 37 | 14.2% | 0.36/0.60 | 4000 | 80 | 540 |
| I46 | 4.5 | 8.8 | 6.1 | 12.4% | 0.68/0.32 | 1000 | 50 | 23000 |
| I47 | 4.2 | 7.5 | 5.7 | 7.1% | 0.14/0.12 | 6000 | 50 | 175 |
TABLE 3
Structural formulae of the materials for the OLEDs
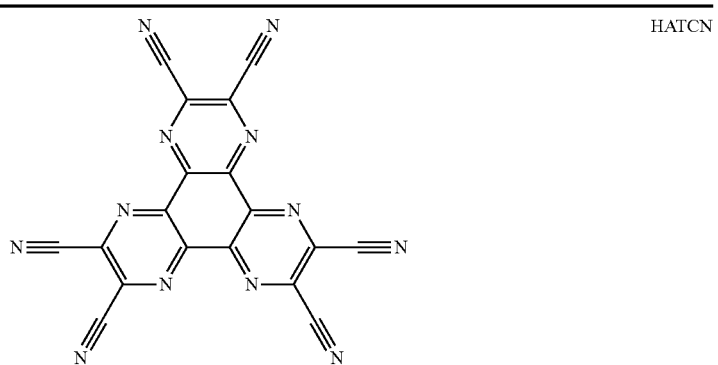
HATCN TABLE 3-continued
Structural formulae of the materials for the OLEDs
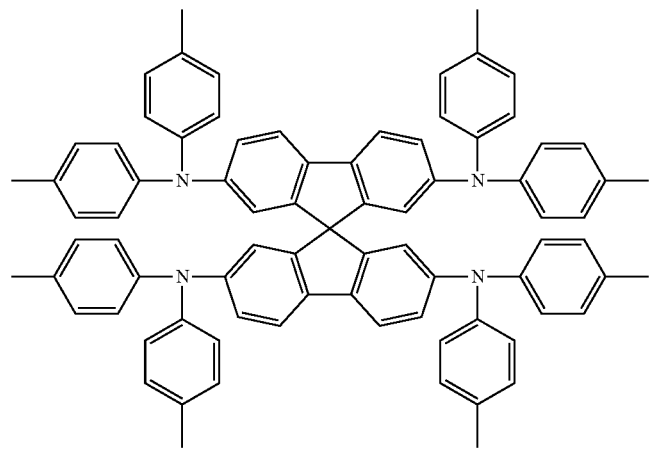
SpA1
(prior art)
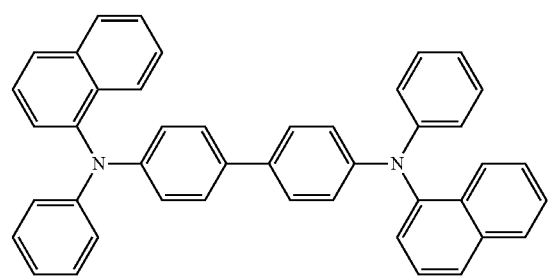
NPB
(prior art)
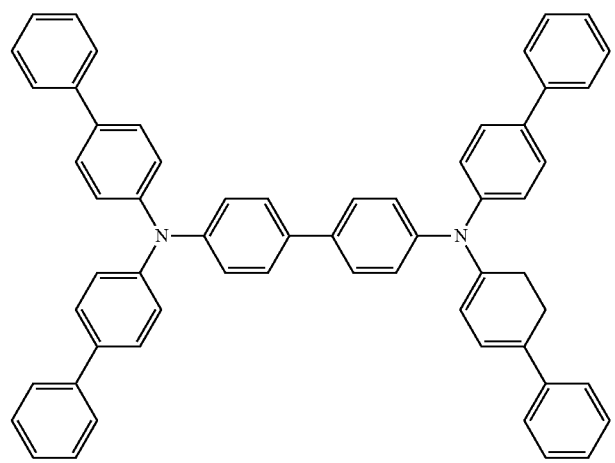
BPA1
(prior art)
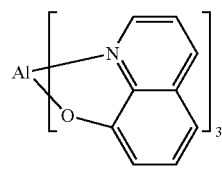
Alq$_3$ TABLE 3-continued
Structural formulae of the materials for the OLEDs
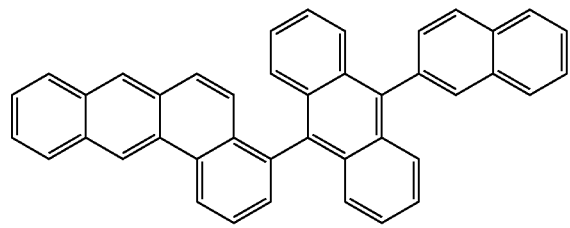 [SMILES: c1ccc2cc(-c3c4ccccc4c(-c4cccc5c4ccc4cc6ccccc6cc45)c4ccccc34)ccc2c1]
M1
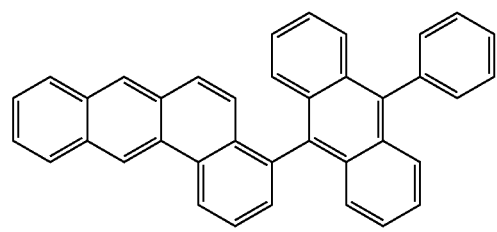 [SMILES: c1ccc(-c2c3ccccc3c(-c3cccc4c3ccc3cc5ccccc5cc34)c3ccccc23)cc1]
M2
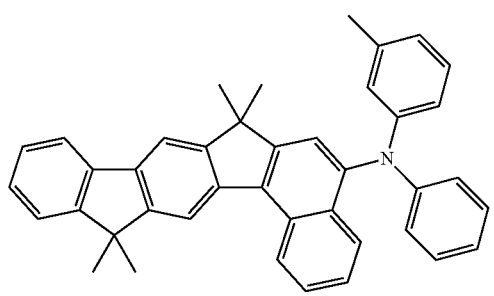 [SMILES: Cc1cccc(N(c2ccccc2)c2cc3c(c4ccccc24)-c2cc4c(cc2C3(C)C)-c2ccccc2C4(C)C)c1]
D1
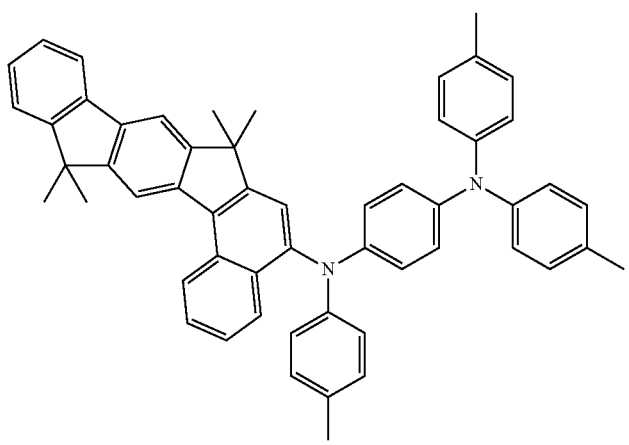 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
D2
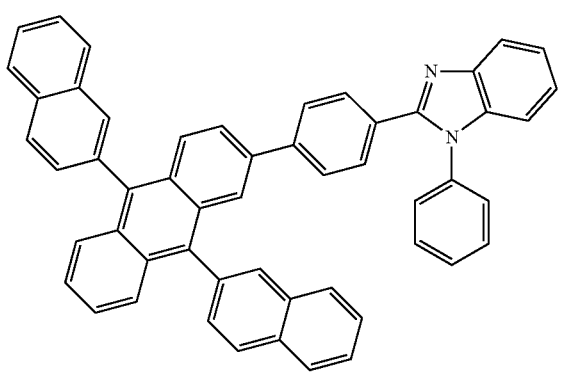 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1

TABLE 3-continued
Structural formulae of the materials for the OLEDs
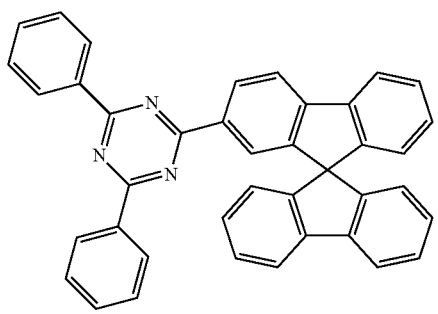
ST1
(prior art)
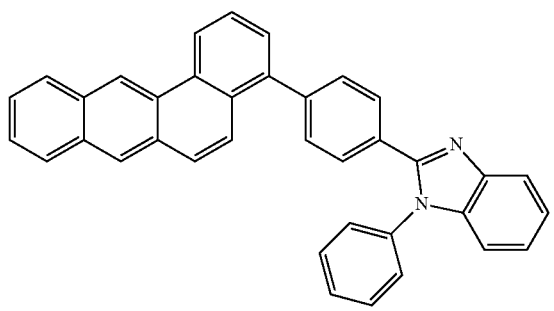 [SMILES: c1ccc(-n2c(-c3ccc(-c4cccc5c4ccc4cc6ccccc6cc45)cc3)nc3ccccc32)cc1]
ETM2
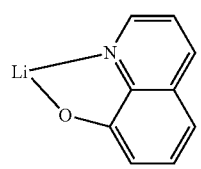
LiQ
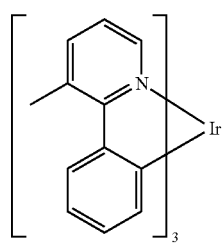
TEG1
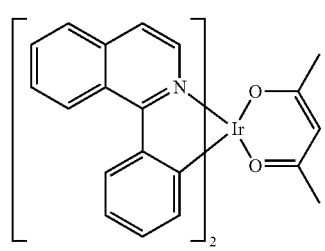
TER1
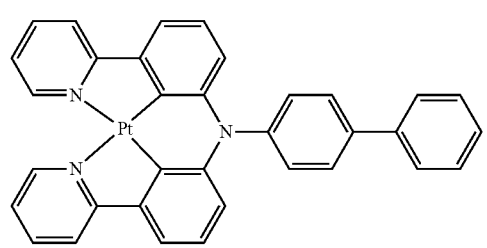
TER2

TABLE 3-continued
Structural formulae of the materials for the OLEDs
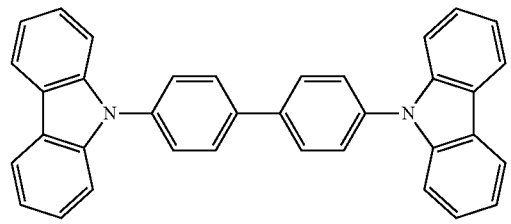
CBP
(prior art)
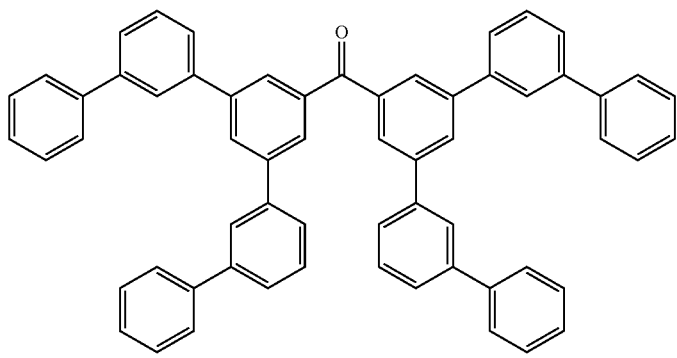
KEt1
(prior art)
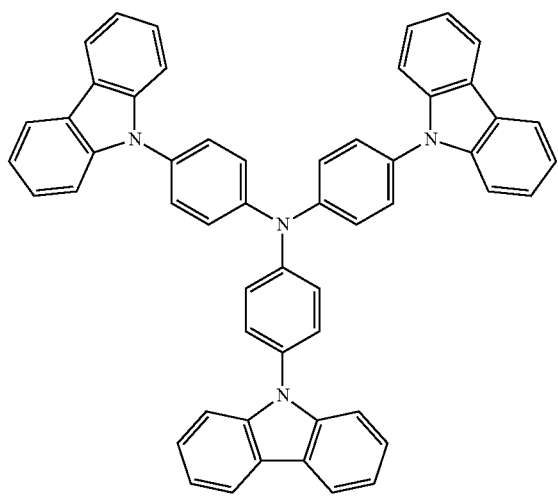
TCTA
(prior art)

TABLE 3-continued
Structural formulae of the materials for the OLEDs
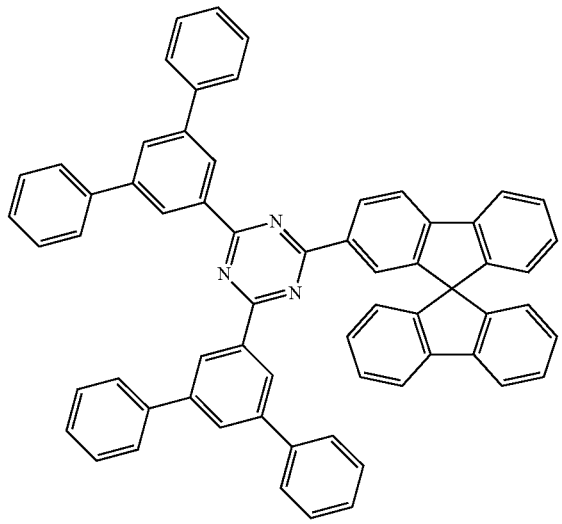 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
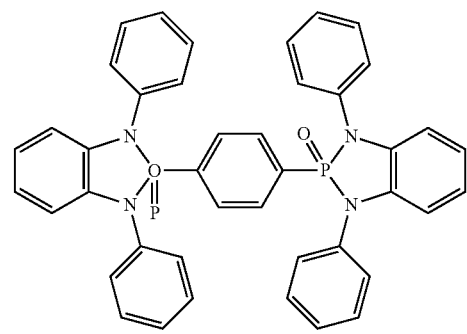
DAP1
(prior art)
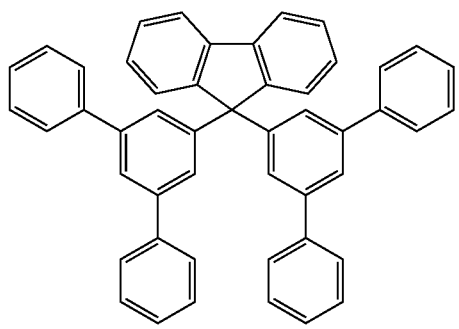
FTPh
(prior art)
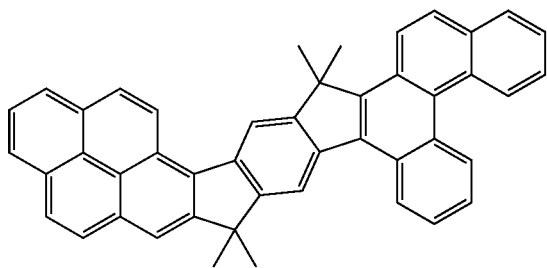 [SMILES: CC1(C)c2cc3c(cc2-c2c1cc1ccc4cccc5ccc2c1c45)C(C)(C)c1c-3c2ccccc2c2c1ccc1ccccc12]
D3

TABLE 3-continued
Structural formulae of the materials for the OLEDs
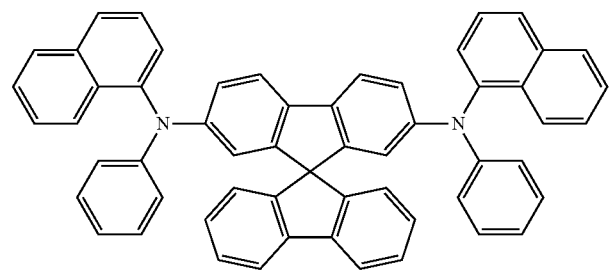 [SMILES: c1ccc(N(c2ccc3c(c2)C2(c4ccccc4-c4ccccc42)c2cc(N(c4ccccc4)c4cccc5ccccc45)ccc2-3)c2cccc3ccccc23)cc1]
SpNBP
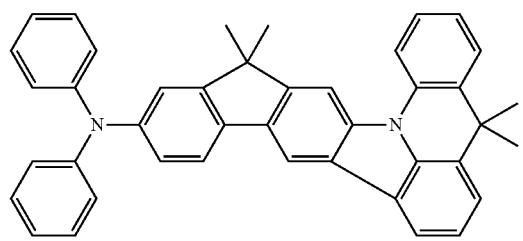
(compound 1 of the synthesis examples)
HTM1
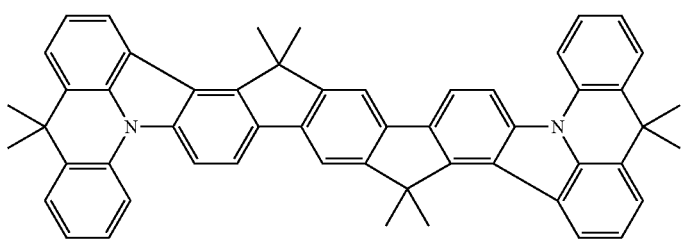
(compound 3 of the synthesis examples)
HTM2
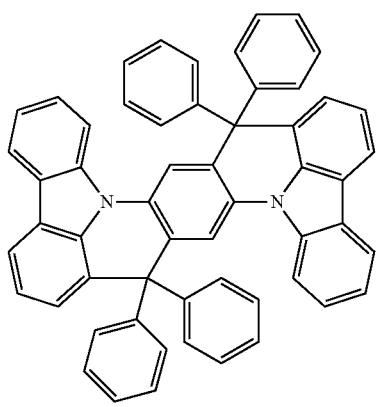
(compound 6 of the synthesis examples)
HTM3

TABLE 3-continued
Structural formulae of the materials for the OLEDs
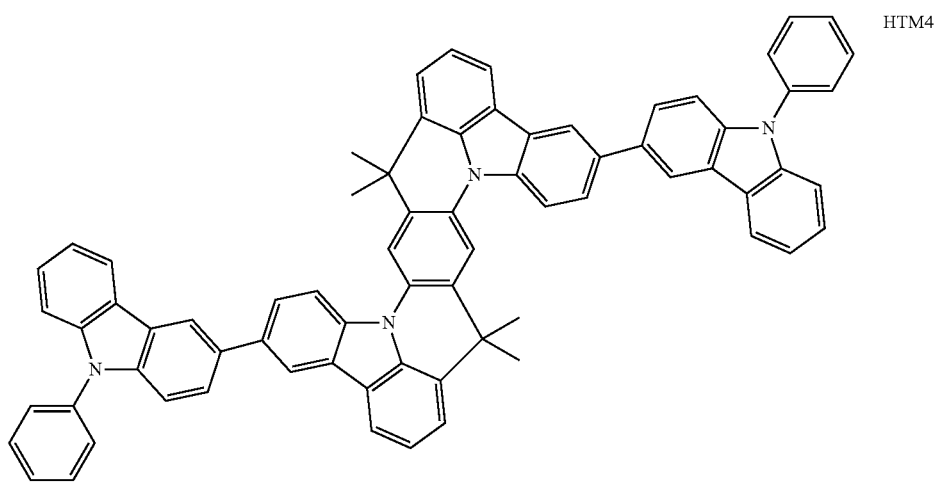
HTM4
(compound 7 of the synthesis examples)
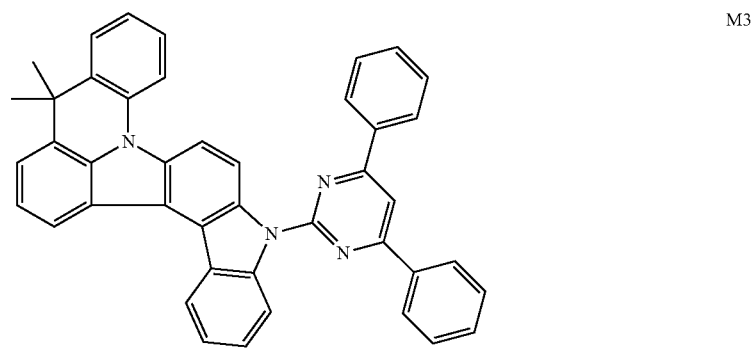
M3
(compound 8 of the synthesis examples)
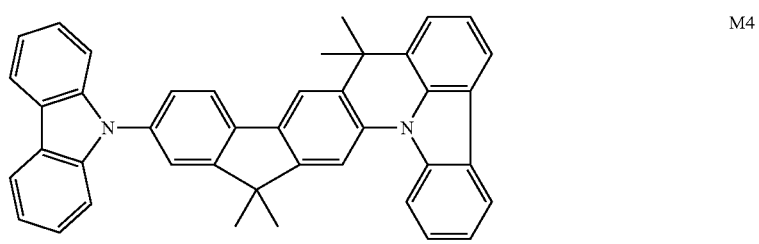
M4
(compound 9 of the synthesis examples)
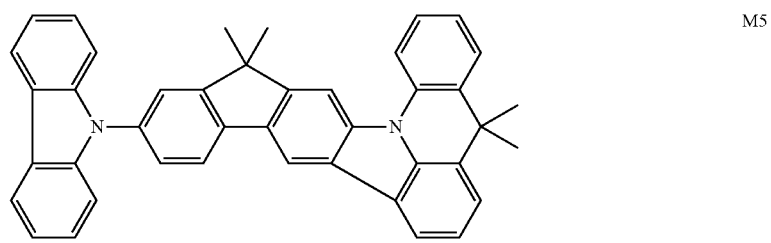
M5
(compound 2 of the synthesis examples)

TABLE 3-continued
Structural formulae of the materials for the OLEDs
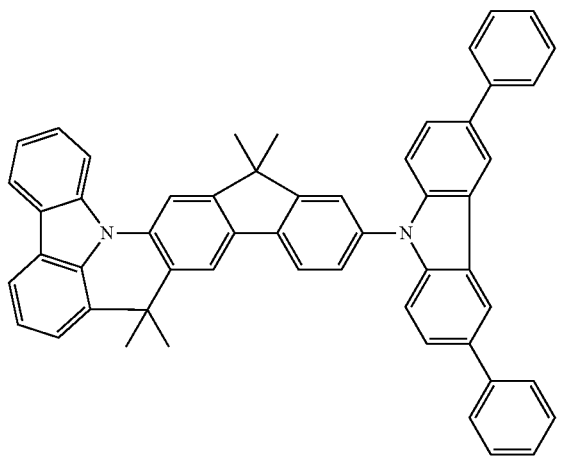
M6
(compound 10h of the synthesis examples)
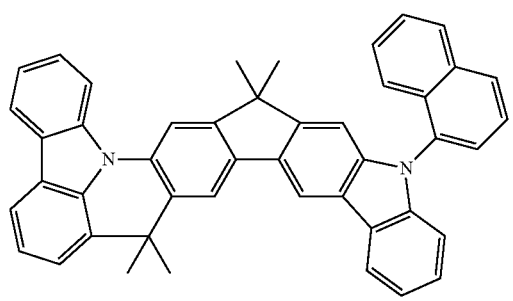
M7
(compound 10i of the synthesis examples)
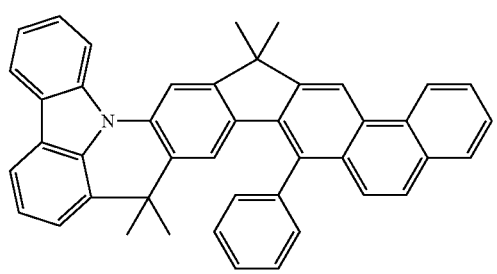
M8
(compound 10l of the synthesis examples)
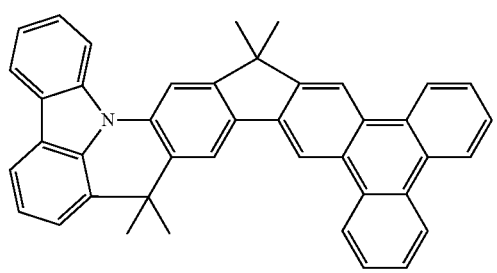
M9
(compound 10m of the synthesis examples)

TABLE 3-continued
Structural formulae of the materials for the OLEDs
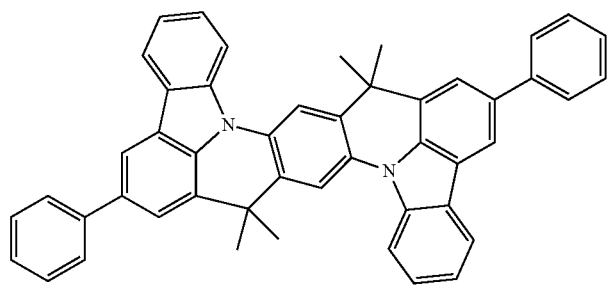
M10
(compound 5c of the synthesis examples)
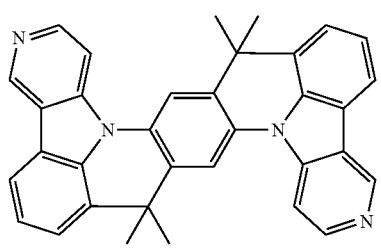
M11
(compound 5h of the synthesis examples)
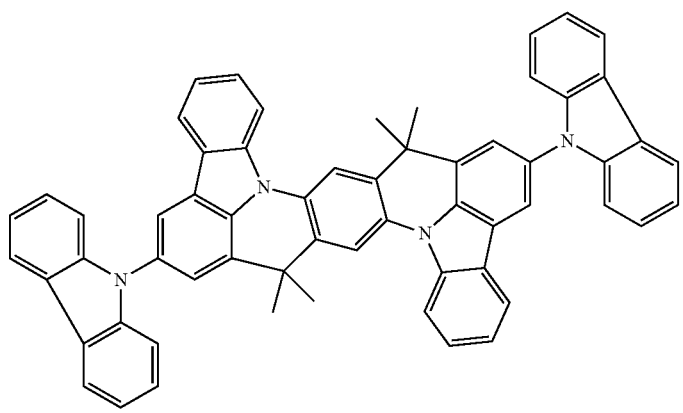
M12
(compound 5k of the synthesis examples)
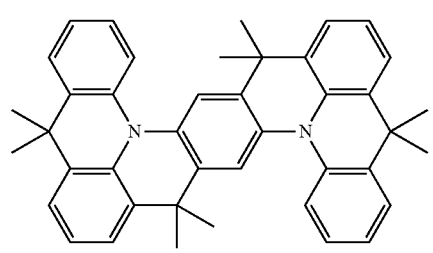
HTM5
(compound 5i of the synthesis examples)

TABLE 3-continued
Structural formulae of the materials for the OLEDs
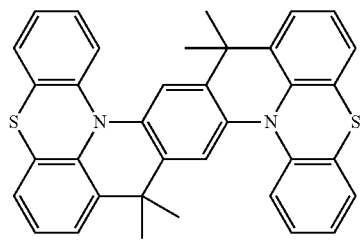
(compound 5j of the synthesis examples)
HTM6
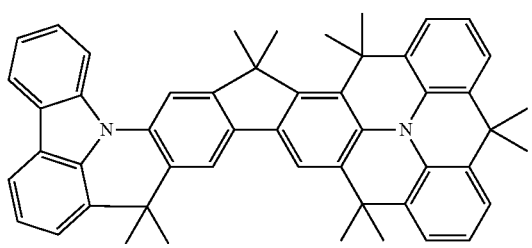
(compound 10g of the synthesis examples)
HTM7
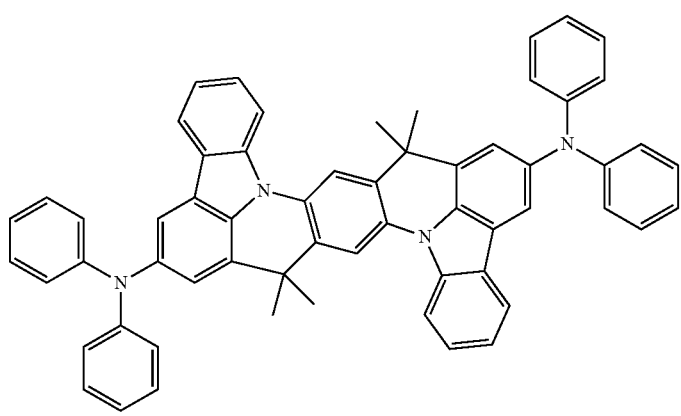
(compound 5d of the synthesis examples)
HTM8
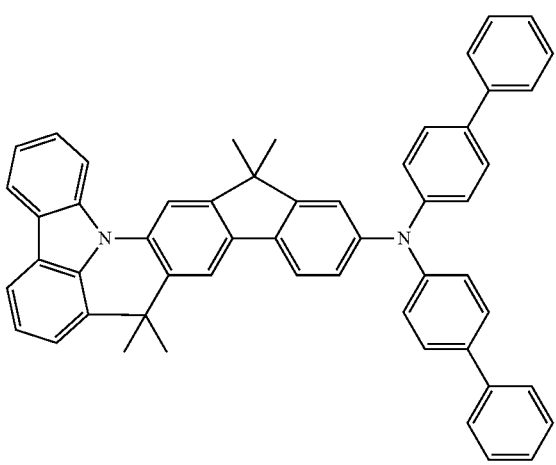
(compound 10a of the synthesis examples)
HTM9

TABLE 3-continued
Structural formulae of the materials for the OLEDs
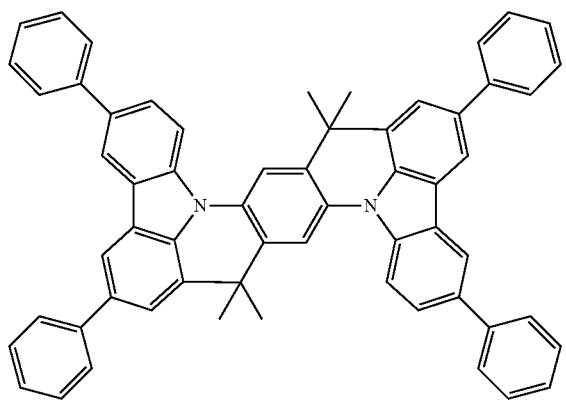
(compound 5e of the synthesis examples)
HTM10
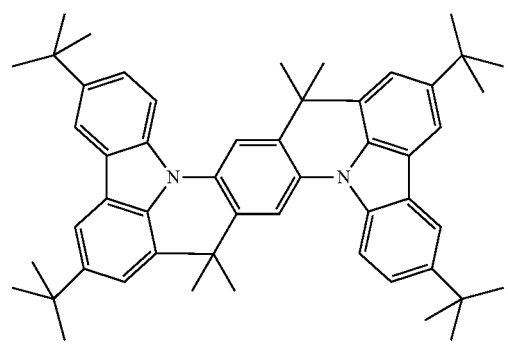
(compound 5g of the synthesis examples)
HTM11
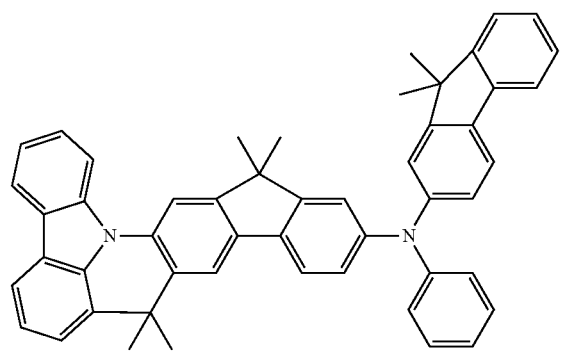
(compound 10b of the synthesis examples)
HTM12

TABLE 3-continued
Structural formulae of the materials for the OLEDs
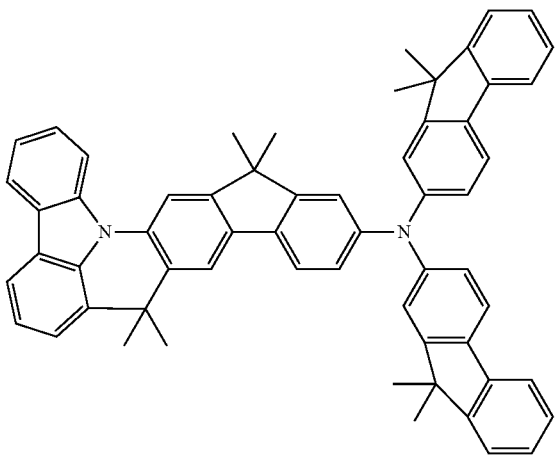
(compound 10j of the synthesis examples)
HTM13
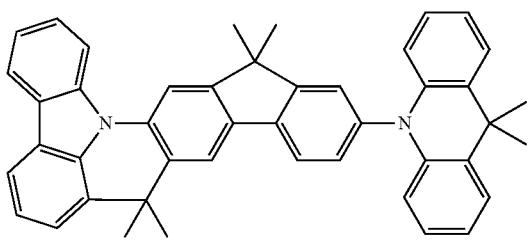
(compound 10e of the synthesis examples)
HTM14
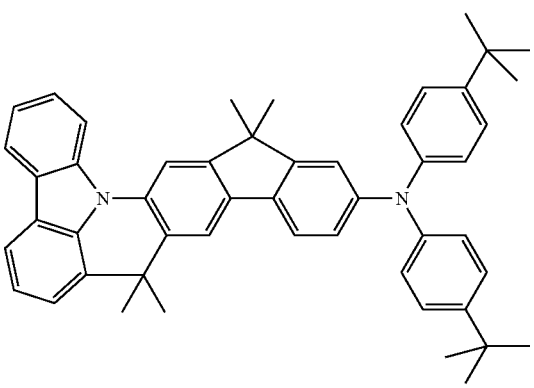
(compound 10k of the synthesis examples)
HTM15
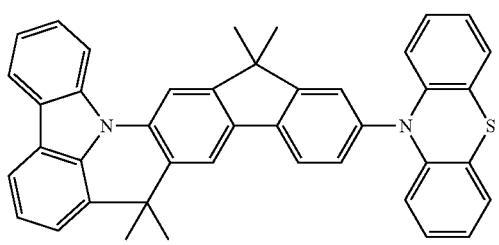
(compound 10d of the synthesis examples)
HTM16

TABLE 3-continued
Structural formulae of the materials for the OLEDs
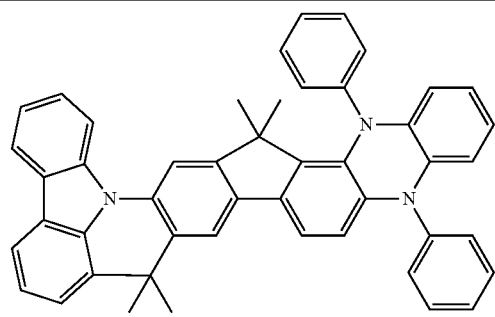
HTM17
(compound 10c of the synthesis examples)
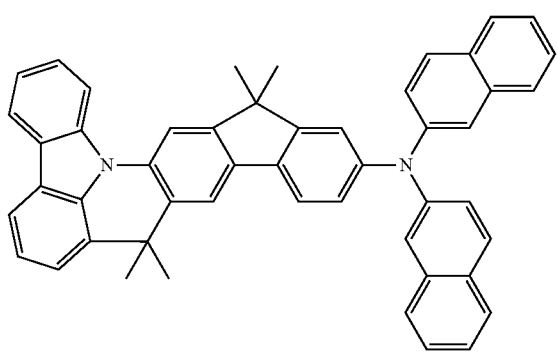
HTM18
(compound 10f of the synthesis examples)
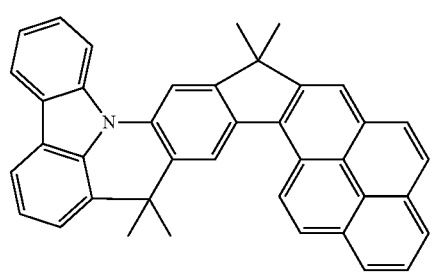
D4
(compound 10n of the synthesis examples)
The invention claimed is:
1. A compound of formulae (I-1) to (I-4)
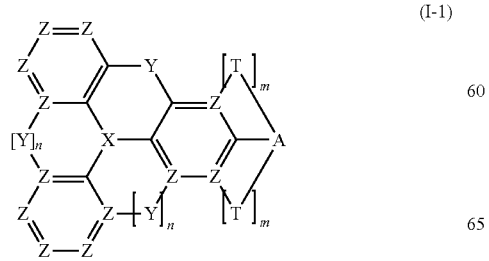
(I-1)
-continued
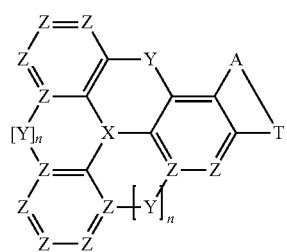
(I-2)

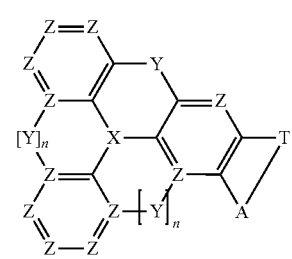

(I-3)

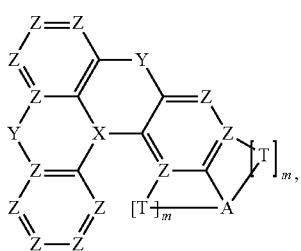

(I-4)

wherein
X is N, P, or P=O;
Y is, identically or differently on each occurrence, $C(R^1)_2$, C=O, C=NR$^1$, O, S, SO, SO$_2$, PR$^1$, POR$^1$, NAr, NR$^1$, or a single bond;
Z is identically or differently on each occurrence, CR$^2$, N, or C if a group Y or T is bonded to Z;
T is, identically or differently on each occurrence, $C(R^1)_2$, C=O, C=NR$^1$, O, S, SO, SO$_2$, PR$^1$, POR$^1$, NAr, NR$^1$, or a single bond;
A is Ar$^3$, which is an aryl group with 6 to 14 aromatic ring carbons, optionally substituted by one or more radicals R$^2$, wherein the bond to a group T starts from the aromatic ring of the group Ar$^3$;
Ar are, identically or differently on each occurrence, an aryl or heteroaryl group having 5 to 30 aromatic ring atoms optionally substituted by one or more radicals R$^2$;
R$^1$ and R$^2$ are, identically or differently on each occurrence, H, D, F, Cl, Br, I, CHO, NAr$_2$, N(R$^3$)$_2$, C(=O)R$^3$, P(=O)(R$^3$)$_2$, S(=O)R$^3$, CR$^3$=C(R$^3$)$_2$, CN, NO$_2$, Si(R$^3$)$_3$, B(OR$^3$)$_2$, OSO$_2$R$^3$, OH, a straight-chain alkyl, alkoxy or thioalkyl group having 1 to 40 C atoms, a branched or cyclic alkyl, alkoxy or thioalkyl group having 3 to 40 C atoms, or an alkenyl or alkynyl group having 2 to 40 C atoms, each of which is optionally substituted by one or more radicals R$_3$, wherein one or more non-adjacent CH$_2$ groups are optionally replaced by —R$^3$C=CR$^3$—, —C≡C—, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, —O—, —S—, —COO—, or —CONR$^3$—, and wherein one or more H atoms are optionally replaced by D, F, Cl, Br, I, CN, NO$_2$, an aromatic or heteroaromatic ring system having 5 to 60 aromatic ring atoms, which in each case is optionally substituted by one or more radicals R$^3$, an aryloxy or heteroaryloxy group having 5 to 60 aromatic ring atoms, optionally substituted by one or more radicals R$^3$, or a combination of these systems, wherein two or more radicals R$^1$ and R$^2$ optionally define a ring or ring system;
R$^3$ is, identically or differently on each occurrence, H, D, F, Cl, Br, I, CHO, NAr$_2$, N(R$^4$)$_2$, C(=O)R$^4$, P(=O)(R$^4$)$_2$, S(=O)R$^4$, S(=O)$_2$R$^4$, CR$^4$=C(R$^4$)$_2$, CN, NO$_2$, Si(R$^4$)$_3$, B(OR$^4$)$_2$, OSO$_2$R$^4$, OH, a straight-chain alkyl, alkoxy or thioalkyl group having 1 to 40 C atoms, a branched or cyclic alkyl, alkoxy or thioalkyl group having 3 to 40 C atoms, or an alkenyl or alkynyl group having 2 to 40 C atoms, each of which is optionally substituted by one or more radicals R$^4$,
wherein one or more non-adjacent CH$_2$ groups are optionally replaced by —R$^4$C=CR$^4$—, —C≡C—, Si(R$^4$)$_2$, Ge(R$^4$)$_2$, Sn(R$^4$)$_2$, C=O, C=S, C=Se, C=NR$^4$, P(=O)(R$^4$), SO, SO$_2$, NR$^4$, —O—, —S—, —COO—, or —CONR$^4$—, and wherein one or more H atoms are optionally replaced by D, F, Cl, Br, I, CN or NO$_2$, an aromatic or heteroaromatic ring system having 5 to 60 aromatic ring atoms, optionally substituted by one or more radicals R$^4$, an aryloxy or heteroaryloxy group having 5 to 60 aromatic ring atoms, optionally substituted by one or more radicals R$^4$, or a combination of these systems, wherein two or more radicals R$^3$ optionally define a ring or ring system;
R$^4$ is, identically or differently on each occurrence, H, D, F, or an aliphatic, aromatic and/or heteroaromatic organic radical having 1 to 20 C atoms, wherein one or more H atoms are optionally replaced by F, and wherein two or more identical or different substituents R$^4$ optionally define a ring or ring system;
n is, on each occurrence, independently of one another, 0 or 1, with the proviso that the sum of all values for n is greater than or equal to 1;
m is, on each occurrence, independently of one another, 0 or 1, with the proviso that the sum of all values for m is greater than or equal to 1;
and with the proviso that at least one group Y is a single bond.

2. The compound of claim 1, wherein X is N.

3. The compound of claim 1, wherein Y is, identically or differently on each occurrence, $C(R^1)_2$, S, O, C=O, NR$^1$, or a single bond, with the proviso that at least one group Y is a single bond.

4. The compound of claim 1, wherein the sum of the values of n and m is 2 or 3.

5. The compound of claim 1, of formula I-1.

6. The compound of claim 1, wherein said compound is of formulae (I5) to (I-10)

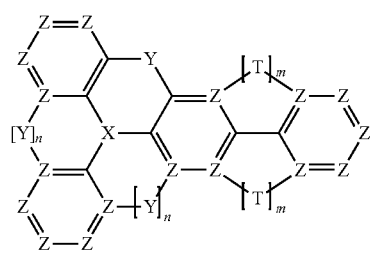

(I-5)

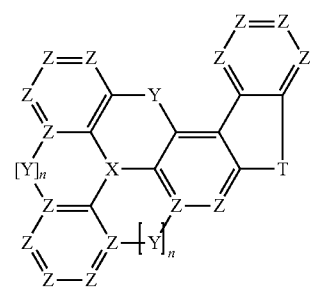

(I-6)

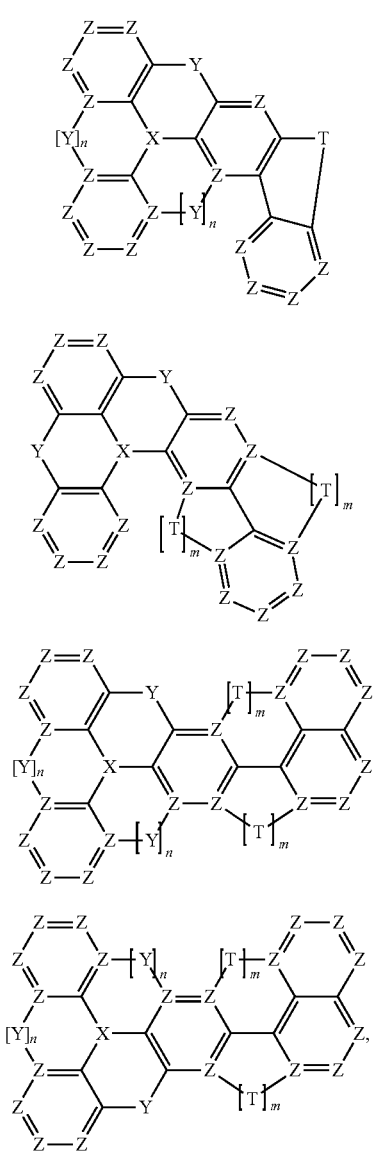

wherein
Z is, identically or differently on each occurrence, CR² or N if no group Y or T is bonded to the group Z, or is on each occurrence C if a group Y or T is bonded to the group Z.

7. An oligomer, polymer, or dendrimer comprising one or more compounds of claim 1, wherein one or more bonds to said oligomer, polymer or dendrimer replace one or more bonds to one or more substituents.

8. A formulation comprising at least one compound of claim 1 and at least one solvent.

9. A process for preparing the compound of claim 1, comprising
a) synthesizing a precursor molecule unbridged in the relevant position and carrying a group Y* and/or T*; and
b) performing the ring-closure reaction, introducing the bridge Y and/or T.

10. An electronic device comprising the compound of claim 1.

11. The electronic device of claim 10, wherein said compound is employed as matrix material in an emitting layer, optionally comprising one or more phosphorescent emitters, and/or is employed as hole-transport material in a hole-transport layer and/or in a hole-injection layer, and/or is employed as emitting material in an emitting layer.

12. A formulation comprising at least one oligomer, polymer, or dendrimer of claim 7 and at least one solvent.

13. An electronic device comprising the oligomer, polymer, or dendrimer of claim 7.

14. The electronic device of claim 10, wherein said electronic device is an organic integrated circuit, organic field-effect transistor, organic thin-film transistor, organic light-emitting transistor, organic solar cell, organic optical detector, organic photoreceptor, organic field-quench device, light-emitting electrochemical cell, organic laser diode, or organic electroluminescent device.

15. The electronic device of claim 13, wherein said electronic device is an organic integrated circuit, organic field-effect transistor, organic thin-film transistor, organic light-emitting transistor, organic solar cell, organic optical detector, organic photoreceptor, organic field-quench device, light-emitting electrochemical cell, organic laser diode, or organic electroluminescent device.

16. The compound of claim 1 of formula I-2.

17. The compound of claim 16, wherein X is N; Y is, identically or differently on each occurrence, $C(R^1)_2$, S, O, C=O, $NR^1$, or a single bond, with the proviso that at least one group Y is a single bond; and the sum of the values of n and m is 2 or 3.

18. The compound of claim 1 of formula I-3.

19. The compound of claim 18, wherein X is N; Y is, identically or differently on each occurrence, $C(R^1)_2$, S, O, C=O, $NR^1$, or a single bond, with the proviso that at least one group Y is a single bond; and the sum of the values of n and m is 2 or 3.

20. The compound of claim 1 of formula I-4.

21. The compound of claim 20, wherein X is N; Y is, identically or differently on each occurrence, $C(R^1)_2$, S, O, C=O, $NR^1$, or a single bond, with the proviso that at least one group Y is a single bond; and the sum of the values of n and m is 2 or 3.

22. The compound of claim 5, wherein X is N; Y is, identically or differently on each occurrence, $C(R^1)_2$, S, O, C=O, $NR^1$, or a single bond, with the proviso that at least one group Y is a single bond; and the sum of the values of n and m is 2 or 3.

23. The compound of claim 1, wherein T is, identically or differently on each occurrence, $C(R^1)_2$.

24. The compound of claim 1, wherein Y is, identically or differently on each occurrence, $C(R^1)_2$ or a single bond, with the proviso that at least one group Y is a single bond.

25. The compound of claim 1, wherein T is, identically or differently on each occurrence, $C(R^1)_2$; and Y is, identically or differently on each occurrence, $C(R^1)_2$ or a single bond, with the proviso that at least one group Y is a single bond.

26. The compound of claim 1, wherein Z is, identically or differently on each occurrence, $CR^2$, or if a group Y or T is bonded to the group Z, then Z is C.

* * * * *